(12) United States Patent
Lassen

(10) Patent No.: US 8,465,959 B2
(45) Date of Patent: Jun. 18, 2013

(54) PROTEASES AND METHODS FOR PRODUCING THEM

(75) Inventor: Soren Flensted Lassen, Farum (DK)

(73) Assignee: Novozymes A/S, Bagsvaerd (DK)

( * ) Notice: Subject to any disclaimer, the term of this patent is extended or adjusted under 35 U.S.C. 154(b) by 581 days.

(21) Appl. No.: 12/147,683

(22) Filed: Jun. 27, 2008

(65) Prior Publication Data

US 2008/0293104 A1 Nov. 27, 2008

Related U.S. Application Data

(62) Division of application No. 10/560,224, filed as application No. PCT/DK2004/000436 on Jun. 21, 2004, now abandoned.

(60) Provisional application No. 60/480,292, filed on Jun. 20, 2003, provisional application No. 60/531,067, filed on Dec. 18, 2003, provisional application No. 60/549,348, filed on Mar. 2, 2004.

(30) Foreign Application Priority Data

Jun. 19, 2003 (DK) .................................. 2003 00916
Dec. 12, 2003 (DK) .................................. 2003 01847
Mar. 1, 2004 (DK) .................................. 2004 00334

(51) Int. Cl.
   *C12N 9/12* (2006.01)

(52) U.S. Cl.
   USPC ........................................................ 435/212

(58) Field of Classification Search
   None
   See application file for complete search history.

(56) References Cited

U.S. PATENT DOCUMENTS

| 5,646,028 | A | 7/1997 | Leigh | |
|---|---|---|---|---|
| 6,511,371 | B2 * | 1/2003 | Outtrup et al. | 435/219 |
| 7,179,630 | B2 | 2/2007 | Lassen | |
| 7,208,310 | B2 | 4/2007 | Lassen et al. | |
| 7,485,447 | B2 * | 2/2009 | Lassen | 435/220 |
| 2002/0182672 | A1 | 12/2002 | Kolkman | |
| 2006/0236414 | A1 | 10/2006 | Lassen et al. | |
| 2008/0286415 | A1 * | 11/2008 | Lassen et al. | 426/63 |
| 2009/0047387 | A1 * | 2/2009 | De Maria et al. | 426/63 |

FOREIGN PATENT DOCUMENTS

| JP | 2003284571 A | | 10/2003 |
|---|---|---|---|
| WO | WO 97/33984 | * | 9/1997 |
| WO | WO 01/58276 | | 8/2001 |
| WO | WO 02/055717 | | 7/2002 |
| WO | WO 2004/072221 | | 8/2004 |
| WO | WO 2004/072279 | | 8/2004 |
| WO | WO 2004/111220 | | 12/2004 |
| WO | WO 2004/111221 | | 12/2004 |
| WO | WO 2004/111222 | | 12/2004 |
| WO | WO 2004/111223 | | 12/2004 |
| WO | WO 2004/111224 | | 12/2004 |

OTHER PUBLICATIONS

Galye et al, Identification of regions in interleukin-1 alpha important for activity. J Biol Chem. Oct. 15, 1993;268(29):22105-11.*
Whisstock et al, Prediction of protein function from protein sequence and structure. Q Rev Biophys. Aug. 2003;36(3):307-40. Review.*
Dixit et al., Biochimica et Biophysica. vol. 1523, pp. 261-268 (2000).
Mitsuiki et al., Enzyme and Microbial Technology, vol. 34, pp. 482-489 (2004).
Lao et al., Applied and Environmental Microbiology, vol. 62, No. 11, p. 4256-4259 (1996).
Tsuijibo et al., Agric. Biol Chem,, vol. 54, Part 8, pp. 2177-2179 (1990).
Mitsuiki et al., Biosci. Biotechnol., vol. 66, Part 1, pp. 164-167 (2002).
Yamashiro et al., Biochimica et Biophysica, vol. 1350, pp. 11-14 (1997).
Hayes et al., The Journal of Biological Chemistry, vol. 277. No. 37, pp. 33825-33832 (2002).
Tang et al., Biochemical and Biophysical Research, vol. 301, pp. 1093-1098 (2003).
Takahashi et al., The Japanese Biochemical Society, vol. 130, pp. 99-106 (2001).
Novo Nordisk, Derwent, Database Accession No. AAW92997 (1996).
Novo Nordisk, Derwent, Database Accession No. AAX22316 (1999).
Last office action in related case U.S. Appl. No. 10/560,414, (2008).

* cited by examiner

*Primary Examiner* — Sheridan Swope
(74) *Attorney, Agent, or Firm* — Michael W. Krenicky; Robert L. Starnes

(57) ABSTRACT

A secreted mature polypeptide derived from an S2A or S1E protease is described which after maturation has protease activity, which polypeptide when expressed and before maturation comprises a heterologous pro-region. Further, a method for producing polypeptide is described including the step of cultivating a recombinant host cell including a polynucleotide encoding a secreted mature polypeptide which after maturation has protease activity, which polypeptide when expressed and before maturation includes a heterologous pro-region derived from an S2A or S1E protease to produce a supermatant including the polypeptide. The polypeptide may also be recovered.

7 Claims, No Drawings

SEQUENCE LISTING

```
<160> NUMBER OF SEQ ID NOS: 58

<210> SEQ ID NO 1
<211> LENGTH: 1062
<212> TYPE: DNA
<213> ORGANISM: Nocardiopsis sp. NRRL 18262
<220> FEATURE:
<221> NAME/KEY: misc_feature
<222> LOCATION: (1)..(495)
<223> OTHER INFORMATION: Encodes the pro-region shown in positions -165
      to -1 of SEQ ID NO:43.
<220> FEATURE:
<221> NAME/KEY: misc_feature
<222> LOCATION: (496)..(1059)
<223> OTHER INFORMATION: Encodes the mature region shown in positions
      1-188 of SEQ ID NO:43.

<400> SEQUENCE: 1
gctactggag cattacctca gtctcctaca cctgaagcag atgcagtatc gatgcaagaa      60
gcattacaac gtgatcttga tcttacatca gctgaagctg aggaattact tgctgcacaa     120
gatacagcct ttgaagttga tgaagctgcc gctgaagcag ctggtgatgc atatggtggt     180
tcagtattcg atactgaatc actcgaactt actgtactag tgaccgatgc agcagctgtt     240
gaagctgttg aagccacagg tgcaggtaca gagctcgtat cttatggtat tgatggatta     300
gatgagatcg tacaagagct taatgcagct gatgccgttc caggtgtagt tggatggtat     360
cctgatgtag caggtgatac tgttgtctta gaagttcttg aaggctctgg agctgatgtt     420
tctggacttt tagcagacgc aggagtcgat gcatccgcgg ttgaagtgac cacgtcagat     480
cagcctgaac tctatgccga tatcattgga ggcctagcgt acacaatggg tggtcgctgc     540
agcgtaggat ttgcagccac aaatgcagct ggacaacctg gcttcgtgac agctggacat     600
tgcggccgcg tcggtacaca ggttactatc ggcaatggaa gaggtgtctt tgagcaaagc     660
gtatttcccg ggaatgatgc tgccttcgtt agaggtacgt ccaactttac gcttactaac     720
ttagtatcta gatacaacac tggcggatat gcaactgtag caggtcacaa tcaagcacct     780
attggctcta gcgtctgccg ctcagggtcg actacaggat ggcattgtgg aaccattcaa     840
gctagaggtc agagcgtgag ctatcctgaa ggtaccgtaa cgaacatgac tcgtacgact     900
```

```
gtatgtgcag aaccaggtga ctctggaggt tcatatatca gcggtacgca agcgcaaggc    960
gttacctcag gtggatccgg taactgtagg acaggtggca caacgttcta ccaggaagtg   1020
acaccgatgg tgaactcttg gggagttaga ctccgtacat aa                      1062
```

<210> SEQ ID NO 2
<211> LENGTH: 1143
<212> TYPE: DNA
<213> ORGANISM: Artificial sequence
<220> FEATURE:
<223> OTHER INFORMATION: A synthetic 10R gene (10Rsynt-15) encoding a
      S2A protease denoted "10R" fused by PCR in frame to the signal
      peptide encoding sequence of a heterologous protease, Savinase.

<400> SEQUENCE: 2

```
atgaagaaac cgttggggaa aattgtcgca agcaccgcac tactcatttc tgttgctttt     60
agttcatcga tcgcatcggc tgctactgga gcattacctc agtctcctac acctgaagca    120
gatgcagtat cgatgcaaga agcattacaa cgtgatcttg atcttacatc agctgaagct    180
gaggaattac ttgctgcaca agatacagcc tttgaagttg atgaagctgc cgctgaagca    240
gctggtgatg catatggtgg ttcagtattc gatactgaat cactcgaact tactgtacta    300
gtgaccgatg cagcagctgt tgaagctgtt gaagccacag gtgcaggtac agagctcgta    360
tcttatggta ttgatggatt agatgagatc gtacaagagc ttaatgcagc tgatgccgtt    420
ccaggtgtag ttggatggta tcctgatgta gcaggtgata ctgttgtctt agaagttctt    480
gaaggctctg gagctgatgt ttctggactt ttagcagacg caggagtcga tgcatccgcg    540
gttgaagtga ccacgtcaga tcagcctgaa ctctatgccg atatcattgg aggcctagcg    600
tacacaatgg gtggtcgctg cagcgtagga tttcagccca aaatgcagc tggacaacct    660 ggcttcgtga cagctggaca ttgcggccgc gtcggtacac aggttactat cggcaatgga    720
agaggtgtct ttgagcaaag cgtatttccc gggaatgatg ctgccttcgt tagaggtacg    780
tccaacttta cgcttactaa cttagtatct agatacaaca ctggcggata tgcaactgta    840
gcaggtcaca tcaagcacc tattggctct agcgtctgcc gctcagggtc gactacagga    900
tggcattgtg gaaccattca agctagaggt cagagcgtga gctatcctga aggtaccgta    960
acgaacatga ctcgtacgac tgtatgtgca gaaccaggtg actctggagg ttcatatatc   1020
agcggtacgc aagcgcaagg cgttacctca ggtggatccg gtaactgtag gacaggtggc   1080
acaacgttct accaggaagt gacaccgatg gtgaactctt ggggagttag actccgtaca   1140
taa                                                                 1143
```

<210> SEQ ID NO 3
<211> LENGTH: 8
<212> TYPE: PRT
<213> ORGANISM: Artificial sequence
<220> FEATURE:
<223> OTHER INFORMATION: C-terminal amino acid tail expressed as fusion
      to protease of the invention.

<400> SEQUENCE: 3

```
Gln Ser His Val Gln Ser Ala Pro
1               5
```

<210> SEQ ID NO 4
<211> LENGTH: 24
<212> TYPE: DNA
<213> ORGANISM: Artificial sequence
<220> FEATURE:
<223> OTHER INFORMATION: Polynucleotide encoding a C-terminal amino acid -continued tail expressed as fusion to protease of the invention.

<400> SEQUENCE: 4
caatcgcatg ttcaatccgc tcca                                        24

<210> SEQ ID NO 5
<211> LENGTH: 4
<212> TYPE: PRT
<213> ORGANISM: Artificial sequence
<220> FEATURE:
<223> OTHER INFORMATION: C-terminal amino acid tail expressed as fusion
      to protease of the invention.

<400> SEQUENCE: 5

Gln Ser Ala Pro
1

<210> SEQ ID NO 6
<211> LENGTH: 12
<212> TYPE: DNA
<213> ORGANISM: Artificial sequence
<220> FEATURE:
<223> OTHER INFORMATION: Polynucleotide encoding a C-terminal amino acid
      tail expressed as fusion to protease of the invention.

<400> SEQUENCE: 6
caatcggctc ct                                                     12

<210> SEQ ID NO 7
<211> LENGTH: 2
<212> TYPE: PRT
<213> ORGANISM: Artificial sequence
<220> FEATURE:
<223> OTHER INFORMATION: C-terminal amino acid tail expressed as fusion
      to protease of the invention.

<400> SEQUENCE: 7

Gln Pro
1

<210> SEQ ID NO 8
<211> LENGTH: 6
<212> TYPE: DNA
<213> ORGANISM: Artificial sequence
<220> FEATURE:
<223> OTHER INFORMATION: Polynucleotide encoding a C-terminal amino acid
      tail expressed as fusion to protease of the invention.

<400> SEQUENCE: 8 caacca                                                             6

<210> SEQ ID NO 9
<211> LENGTH: 1
<212> TYPE: PRT
<213> ORGANISM: Artificial sequence
<220> FEATURE:
<223> OTHER INFORMATION: C-terminal amino acid tail expressed as fusion
      to protease of the invention.

<400> SEQUENCE: 9

Pro
1

<210> SEQ ID NO 10
<211> LENGTH: 3
<212> TYPE: DNA
<213> ORGANISM: Artificial sequence
<220> FEATURE:

<223> OTHER INFORMATION: Polynucleotide encoding a C-terminal amino acid
      tail expressed as fusion to protease of the invention.

<400> SEQUENCE: 10 cca                                                                       3

<210> SEQ ID NO 11
<211> LENGTH: 45
<212> TYPE: DNA
<213> ORGANISM: Artificial sequence
<220> FEATURE:
<223> OTHER INFORMATION: Primer #252639

<400> SEQUENCE: 11
catgtgcatg tgggtaccgc aacgttcgca gatgctgctg aagag                        45

<210> SEQ ID NO 12
<211> LENGTH: 44
<212> TYPE: DNA
<213> ORGANISM: Artificial sequence
<220> FEATURE:
<223> OTHER INFORMATION: Primer #251992

<400> SEQUENCE: 12
catgtgcatg tggtcgaccg attatggagc ggattgaaca tgcg                         44

<210> SEQ ID NO 13
<211> LENGTH: 44
<212> TYPE: DNA
<213> ORGANISM: Artificial sequence
<220> FEATURE:
<223> OTHER INFORMATION: Primer #179541

<400> SEQUENCE: 13
gcgttgagac gcgcggccgc gagcgccgtt tggctgaatg atac                         44

<210> SEQ ID NO 14
<211> LENGTH: 43
<212> TYPE: DNA
<213> ORGANISM: Artificial sequence
<220> FEATURE:
<223> OTHER INFORMATION: Primer #179542

<400> SEQUENCE: 14
gcgttgagac agctcgagca gggaaaaatg gaaccgcttt ttc                          43

<210> SEQ ID NO 15
<211> LENGTH: 64
<212> TYPE: DNA
<213> ORGANISM: Artificial sequence
<220> FEATURE:
<223> OTHER INFORMATION: Primer #179539

<400> SEQUENCE: 15
ccatttgatc agaattcact ggccgtcgtt ttacaaccat tgcggaaaat agtcataggc        60
atcc                                                                     64

<210> SEQ ID NO 16
<211> LENGTH: 60
<212> TYPE: DNA
<213> ORGANISM: Artificial sequence
<220> FEATURE:
<223> OTHER INFORMATION: Primer #179540

<400> SEQUENCE: 16
ggatccagat ctggtacccg ggtctagagt cgacgcggcg gttcgcgtcc ggacagcaca        60

<210> SEQ ID NO 17
<211> LENGTH: 37
<212> TYPE: DNA
<213> ORGANISM: Artificial sequence
<220> FEATURE:
<223> OTHER INFORMATION: Primer #179154

<400> SEQUENCE: 17
gttgtaaaac gacggccagt gaattctgat caaatgg                              37

<210> SEQ ID NO 18
<211> LENGTH: 37
<212> TYPE: DNA
<213> ORGANISM: Artificial sequence
<220> FEATURE:
<223> OTHER INFORMATION: Primer #179153

<400> SEQUENCE: 18
ccgcgtcgac actagacacg ggtacctgat ctagatc                              37

<210> SEQ ID NO 19
<211> LENGTH: 22
<212> TYPE: DNA
<213> ORGANISM: Artificial sequence
<220> FEATURE:
<223> OTHER INFORMATION: Primer #317

<400> SEQUENCE: 19
tggcgcaatc ggtaccatgg gg                                              22

<210> SEQ ID NO 20
<211> LENGTH: 40
<212> TYPE: DNA
<213> ORGANISM: Artificial sequence
<220> FEATURE:
<223> OTHER INFORMATION: Primer #139 NotI

<400> SEQUENCE: 20
catgtgcatg cggccgcatt aacgcgttgc cgcttctgcg                           40

<210> SEQ ID NO 21
<211> LENGTH: 7443
<212> TYPE: DNA
<213> ORGANISM: Artificial sequence
<220> FEATURE:
<223> OTHER INFORMATION: Sequence of plasmid pMB1508

<400> SEQUENCE: 21
tcgcgcgttt cggtgatgac ggtgaaaacc tctgacacat gcagctcccg gagacggtca      60
cagcttgtct gtaagcggat gccggagcaa gacaagcccg tcagggcgcg tcagcgggtg     120
ttggcgggtg tcggggctgg cttaactatg cggcatcaga gcagattgta ctgagagtgc     180
accatatgcg gtgtgaaata ccgcacagat gcgtaaggag aaaataccgc atcaggcgcc     240
attcgccatt caggctgcgc aactgttggg aagggcgatc ggtgcgggcc tcttcgctat     300
tacgccagct ggcgaaaggg ggatgtgctg caaggcgatt aagttgggta acgccagggt     360
tttcccagtc acgacgttgt aaaacgacgg ccagtgaatt cgataaaagt gcttttttg      420 ttgcaattga agaattatta atgttaagct taattaaaga taatatcttt gaattgtaac     480
gcccctcaaa gtaagaact acaaaaaaag aatacgttat atagaaatat gtttgaacct     540
tcttcagatt acaaatatat tcggacggac tctacctcaa atgcttatct aactatagaa     600
tgacatacaa gcacaacctt gaaaatttga aaatataact accaatgaac ttgttcatgt     660

```
gaattatcgc tgtatttaat tttctcaatt caatatataa tatgccaata cattgttaca    720
agtagaaatt aagacaccct tgatagcctt actataccta acatgatgta gtattaaatg    780
aatatgtaaa tatatttatg ataagaagcg acttatttat aatcattaca tattttcta    840
ttggaatgat taagattcca atagaatagt gtataaatta tttatcttga aaggagggat    900
gcctaaaaac gaagaacatt aaaaacatat atttgcaccg tctaatggat ttatgaaaaa    960
tcatttatc agtttgaaaa ttatgtatta tggagctctg aaaaaaagga gaggataaag   1020
aatgaagaaa ccgttgggga aaattgtcgc aagcaccgca ctactcattt ctgttgcttt   1080
tagttcatcg atcgcatcgg ctgctgaaga agcaaaagaa aaatatttaa ttggctttaa   1140
tgagcaggaa gctgtcagtg agtttgtaga acaagtagag gcaaatgacg aggtcgccat   1200
tctctctgag gaagaggaag tcgaaattga attgcttcat gaatttgaaa cgattcctgt   1260
tttatccgtt gagttaagcc cagaagatgt ggacgcgctt gaactcgatc cagcgatttc   1320
ttatattgaa gaggatgcag aagtaacgac aatggcgcaa tcggtaccat ggggtatatc   1380
aacgcgttaa tccgcggata tatagcggcc gcagatctgg gaccaataat aatgactaga   1440
gaagaaagaa tgaagattgt tcatgaaatt aaggaacgaa tattggataa agtgggatat   1500
ttttaaaata tatatttatg ttacagtaat attgactttt aaaaaaggat tgattctaat   1560
gaagaaagca gacaagtaag cctcctaaat tcactttaga taaaaattta ggaggcatat   1620
caaatgaact ttaataaaat tgatttagac aattggaaga gaaagagat atttaatcat   1680
tatttgaacc aacaaacgac ttttagtata accacagaaa ttgatattag tgttttatac   1740
cgaaacataa acaagaagg atataaattt taccctgcat ttatttttctt agtgacaagg   1800
gtgataaact caaatacagc ttttagaact ggttacaata gcgacggaga gttaggttat   1860
tgggataagt tagagccact ttatacaatt tttgatggtg tatctaaaac attctctggt   1920
atttggactc ctgtaaagaa tgacttcaaa gagttttatg attatacct ttctgatgta   1980
gagaaatata atggttcggg gaaattgttt cccaaaacac ctatacctga aaatgcttt   2040
tctcttctta ttattccatg gactcatttt actgggttta acttaaatat caataataat   2100
agtaattacc ttctacccat tattacagca ggaaaattca ttaataagg taattcaata   2160
tatttaccgc tatctttaca ggtacatcat tctgtttgtg atggttatca tgcaggattg   2220
tttatgaact ctattcagga attgtcagat aggcctaatg actggctttt ataatatgag   2280
ataatgccga ctgtactttt tacagtcggt tttctaacga tacattaata ggtacgaaaa   2340
agcaacttt tttgcgctta aaaccagtca taccaataac ttaagggtaa ctagcctcgc   2400
cggaaagagc gaaaatgcct cacatttgtg ccacctaaaa aggagcgatt tacatatgag   2460
ttatgcagtt tgtagaatgc aaaaagtgaa atcagctgga ctaaagggg ccgcagagta   2520
gaatggaaaa ggggatcgga aaacaagtat ataggaggag acctatttat ggcttcagaa   2580
aaagacgcag gaaaacagtc agcagtaaag cttgttccat tgcttattac tgtcgctgtg   2640
ggactaatca tctggtttat tcccgctccg tccggacttg aacctaaagc ttggcatttg   2700
tttgcgattt ttgtcgcaac aattatcggc tttatctcca gcccttgcc aatgggtgca   2760
attgcaattt ttgcattggc ggttactgca ctaactggaa cactatcaat tgaggataca   2820
ttaagcggat tcgggaataa gaccatttgg cttatcgtta tcgcattctt tatttcccgg   2880
ggatttatca aaaccggtct cggtgcgaga atttcgtatg tattcgttca gaaattcgga   2940
aaaaaaccc ttggacttc ttattcactg ctatcagtg atttaatact ttcacctgct   3000
attccaagta atacggcgcg tgcaggaggc attatatttc ctattatcag atcattatcc   3060
```

```
gaaacattcg gatcaagccc ggcaaatgga acagagagaa aaatcggtgc attcttatta    3120
aaaaccggtt ttcaggggaa tctgatcaca tctgctatgt tcctgacagc gatggcggcg    3180
aacccgctga ttgccaagct ggcccatgat gtcgcagggg tggacttaac atggacaagc    3240
tgggcaattg ccgcgattgt accgggactt gtaagcttaa tcatcacgcc gcttgtgatt    3300
tacaaactgt atccgccgga aatcaaagaa acaccggatg cggcgaaaat cgcaacagaa    3360
aaactgaaag aaatgggacc gttcaaaaaa tcggagcttt ccatggttat cgtgtttctt    3420
ttggtgcttg tgctgtggat ttttggcggc agcttcaaca tcgacgctac cacaaccgca    3480
ttgatcggtt tggccgttct cttattatca caagttctga cttgggatga tatcaagaaa    3540
gaacagggcg cttgggatac gctcacttgg tttgcggcgc ttgtcatgct cgccaacttc    3600
ttgaatgaat taggcatggt gtcttggttc agtaatgcca tgaaatcatc cgtatcaggg    3660
ttctcttgga ttgtggcatt catcattttta attgttgtgt attattactc tcactatttc    3720
tttgcaagtg cgacagccca catcagtgcg atgtattcag cattttttggc tgtcgtcgtg    3780 gcagcgggcg caccgccgct tttagcagcg ctgagcctcg cgttcatcag caacctgttc    3840
gggtcaacga ctcactacgg ttctggagcg gctccggtct tcttcggagc aggctacatc    3900
ccgcaaggca atggtggtc catcggattt atcctgtcga ttgttcatat catcgtatgg    3960
cttgtgatcg gcggattatg gtggaaagta ctaggaatat ggtagaaaga aaaaggcaga    4020
cgcggtctgc cttttttttat tttcactcct tcgtaagaaa atggattttg aaaaatgaga    4080
aaattccctg tgaaaaatgg tatgatctag gtagaaagga cggctggtgc tgtggtgaaa    4140
aagcggttcc attttttccct gcaaacaaaa ataatggggc tgattgcggc tctgctggtc    4200
tttgtcattg gtgtgctgac cattacgtta gccgttcagc atacacaggg agaacggaga    4260
caggcagagc agctggcggt tcaaacggcg agaaccattt cctatatgcc gccggttaaa    4320
gagctcattg agagaaaaga cggacatgcg gctcagacgc aagaggtcat tgaacaaatg    4380
aaagaacaga ctggtgcgtt tgccatttat gttttgaacg aaaaaggaga cattcgcagc    4440
gcctctggaa aaagcggatt aaagaaactg gagcgcagca gagaaatttt gtttggcggt    4500
tcgcatgttt ctgaaacaaa agcggatgga cgaagagtga tcagagggag cgcgccgatt    4560
ataaagaaac agaagggata cagccaagtg atcggcagcg tgtctgttga ttttctgcaa    4620
acggagacag agcaaagcat caaaaagcat ttgagaaatt tgagtgtgat tgctgtgctt    4680
gtactgctgc tcggatttat tggcgccgcc gtgctggcga aaagcatcag aaaggatacg    4740
ctcgggcttg aaccgcatga atcgcggct ctatatcgtg agaggaacgc aatgctttc    4800 gcgattcgag aagggattat tgccaccaat cgtgaaggcg tcgtcaccat gatgaacgta    4860
tcggcggccg agatgctgaa gctgcccgag cctgtgatcc atcttcctat agatgacgtc    4920
atgccgggag cagggctgat gtctgtgctt gaaaaaggag aaatgctgcc gaaccaggaa    4980
gtaagcgtca acgatcaagt gtttattatc aatacgaaag tgatgaatca aggcgggcag    5040
gcgtatggga ttgtcgtcag cttcaggag aaaacagagc tgaagaagct gatcgacaca    5100
ttgacagagg ttcgcaaata ttcagaggat ctcaggcgc agactcatga attttcaaat    5160
aagctttatg cgattttagg gctgcgtcga cctgcaggca tgcaagcttg gcgtaatcat    5220
ggtcatagct gtttcctgtg tgaaattgtt atccgctcac aattccacac aacatacgag    5280
ccggaagcat aaagtgtaaa gcctggggtg cctaatgagt gagctaactc acattaattg    5340
cgttgcgctc actgcccgct ttccagtcgg gaaacctgtc gtgccagctg cattaatgaa    5400
tcggccaacg cgcggggaga ggcggtttgc gtattgggcg ctcttccgct tcctcgctca    5460
```

```
ctgactcgct gcgctcggtc gttcggctgc ggcgagcggt atcagctcac tcaaaggcgg    5520
taatacggtt atccacagaa tcagggdata acgcaggaaa gaacatgtga gcaaaaggcc    5580
agcaaaaggc caggaaccgt aaaaaggccg cgttgctggc gttttttccat aggctccgcc    5640 cccctgacga gcatcacaaa aatcgacgct caagtcagag gtggcgaaac ccgacaggac    5700
tataaagata ccaggcgttt ccccctggaa gctccctcgt gcgctctcct gttccgaccc    5760
tgccgcttac cggatacctg tccgcctttc tcccttcggg aagcgtggcg ctttctcata    5820
gctcacgctg taggtatctc agttcggtgt aggtcgttcg ctccaagctg gctgtgtgc    5880 acgaaccccc cgttcagccc gaccgctgcg ccttatccgg taactatcgt cttgagtcca    5940
acccggtaag acacgactta tcgccactgg cagcagccac tggtaacagg attagcagag    6000
cgaggtatgt aggcggtgct acagagttct tgaagtggtg gcctaactac ggctacacta    6060
gaaggacagt atttggtatc tgcgctctgc tgaagccagt taccttcgga aaaagagttg    6120
gtagctcttg atccggcaaa caaaccaccg ctggtagcgg tggtttttttt gtttgcaagc    6180 agcagattac gcgcagaaaa aaaggatctc aagaagatcc tttgatcttt tctacggggt    6240
ctgacgctca gtggaacgaa aactcacgtt aagggatttt ggtcatgaga ttatcaaaaa    6300
ggatcttcac ctagatcctt ttaaattaaa aatgaagttt taaatcaatc taaagtatat    6360
atgagtaaac ttggtctgac agttaccaat gcttaatcag tgaggcacct atctcagcga    6420
tctgtctatt tcgttcatcc atagttgcct gactccccgt cgtgtagata actacgatac    6480
gggagggctt accatctggc cccagtgctg caatgatacc gcgagaccca cgctcaccgg    6540
caccggattt atcagcaata aaccagccag ccggaagggc cgagcgcaga agtggtcctg    6600
caactttatc cgcctccatc cagtctatta attgttgccg ggaagctaga gtaagtagtt    6660
cgccagttaa tagtttgcgc aacgttgttg ccattgctac aggcatcgtg gtgtcacgct    6720
cgtcgtttgg tatggcttca ttcagctccg gttcccaacg atcaaggcga gttacatgat    6780
cccccatgtt gtgcaaaaaa gcggttagct ccttcggtcc tccgatcgtt gtcagaagta    6840
agttggccgc agtgttatca ctcatggtta tggcagcact gcataattct cttactgtca    6900
tgccatccgt aagatgcttt tctgtgactg gtgagtactc aaccaagtca ttctgagaat    6960
agtgtatgcg gcgaccgagt tgctcttgcc cggcgtcaat acgggataat accgcgccac    7020
atagcagaac tttaaaagtg ctcatcattg gaaaacgttc ttcggggcga aaactctcaa    7080
ggatcttacc gctgttgaga tccagttcga tgtaacccac tcgtgcaccc aactgatctt    7140
cagcatcttt tactttcacc agcgtttctg ggtgagcaaa aacaggaagg caaaatgccg    7200
caaaaaaggg aataagggcg acacggaaat gttgaatact catactcttc cttttttcaat    7260 attattgaag catttatcag ggttattgtc tcatgagcgg atacatattt gaatgtattt    7320
agaaaaataa acaaataggg gttccgcgca catttccccg aaaagtgcca cctgacgtct    7380
aagaaaccat tattatcatg acattaacct ataaaaatag gcgtatcacg aggccctttc    7440
gtc                                                                  7443
```

<210> SEQ ID NO 22
<211> LENGTH: 5718
<212> TYPE: DNA
<213> ORGANISM: Artificial sequence
<220> FEATURE:
<223> OTHER INFORMATION: Sequence of MB1510 genomic integration region

<400> SEQUENCE: 22

```
gagcgccgtt tggctgaatg atacaacagt ctcacttcct tactgcgtct ggttgcaaaa      60
```

-continued

| | |
|---|---|
| acgaagaagc aaggattccc ctcgcttctc atttgtccta tttattatac acttttttaa | 120 |
| gcacatcttt ggcgcttgtt tcactagact tgatgcctct gaatcttgtc caagtgtcac | 180 |
| ggtccgcatc atagacttgt ccattttca ccgctttgag attttccag agcgggttcg | 240 |
| ttttccactc atctacaatg gttttgcctt cgttggctga gatgaacaaa atatcaggat | 300 |
| cgattttgct caattgctca aggctgacct cttgataggc gttatctgac ttcacagcgt | 360 |
| gtgtaaagcc tagcatttta aagatttctc cgtcatagga tgatgatgta tgaagctgga | 420 |
| aggaatccgc tcttgcaacg ccgagaacga tgttgcggtt ttcatctttc ggaagttcgg | 480 |
| cttttagatc gttgatgact ttttgtgct cggcaagctt ttcttttcct tcatcttctt | 540 |
| tatttaatgc tttagcaatg gtcgtaaagc tgtcgatcgt ttcgtcatat gtcgcttcac | 600 |
| ggcttttaa ttcaatcgtc ggggcgattt ttttcagctg tttataaatg tttttatggc | 660 |
| gctcagcgtc agcgatgatt aaatcaggct tcaaggaact gatgacctca agattgggtt | 720 |
| cgctgcgtgt gcctacagat gtgtaatcaa tggagctgcc gacaagcttt ttaatcatat | 780 |
| cttttttgtt gtcatctgcg atgcccaccg gcgtaatgcc gagattgtga acggcatcca | 840 |
| agaatgaaag ctcaagcaca accacccgct taggtgtgcc gcttactgtc gttttcctt | 900 |
| cttcgtcatg gatcactctg gaatccttag actcgctttt gccgcttccg ttgttattct | 960 |
| ggcttgatga acagccggat acaatgaggc aggcagcaa taaaacactc atgatggcaa | 1020 |
| tcaacttgtt agataggtg cgcatgtcat tcttccttt tcagattta gtaatgagaa | 1080 |
| tcattatcac atgtaacact ataatagcat ggcttatcat gtcaatattt ttttagtaaa | 1140 |
| gaaagctgcg tttttactgc tttctcatga agcatcatc agacacaaat aagtggtatg | 1200 |
| cagcgttacc gtgtcttcga gacaaaaacg catgggcgtt ggctttagag gtttcgaaca | 1260 |
| tatcagcagt gacataagga aggagagtgc tgagataacc ggacaattc ttttctattt | 1320 |
| catctgttag tgcaaattca atgtcgccga tattcatgat aatcgagaaa acaaagtcga | 1380 |
| tatcgatatg aaaatgttcc tcggcaaaaa ccgcaagctc gtgaattcct ggtgaacatc | 1440 |
| cggcacgctt atggaaaatc tgtttgacta aatcactcac aatccaagca ttgtattgct | 1500 |
| gttctggtga aaagtattgc attagacata cctcctgctc gtacggataa aggcagcgtt | 1560 |
| tcatggtcgt gtgctccgtg cagcggcttc tccttaattt tgattttct gaaataggt | 1620 |
| cccgttccta tcactttacc atggacggaa acaaatagc tactaccatt cctcctgttt | 1680 |
| ttctcttcaa tgttctggaa tctgtttcag gtacagacga tcgggtatga agaaatata | 1740 |
| gaaaacatga aggaggaata tcgacatgaa accagttgta aaagagtata caaatgacga | 1800 |
| acagctcatg aaagatgtag aggaattgca gaaaatgggt gttgcgaaag aggatgtata | 1860 |
| cgtcttagct cacgacgatg acagaacgga acgcctggct gacaacacga acgccaacac | 1920 |
| gatcggagcc aaagaaacag gtttcaagca cgcggtggga aatatcttca ataaaaaagg | 1980 |
| agacgagctc cgcaataaaa ttcacgaaat cggttttct gaagatgaag ccgctcaatt | 2040 |
| tgaaaaacgc ttagatgaag gaaaagtgct tctctttgtg acagataacg aaaaagtgaa | 2100 |
| agcttgggca taaagcaagg aaaaaaccaa aaggccaatg tcggccttt ggttttttg | 2160 |
| cggtctttgc ggtgggattt tgcagaatgc cgcaatagga tagcggaaca ttttcggttc | 2220 |
| tgaatgtccc tcaatttgct attatatttt tgtgataaat tggaataaaa tctcacaaaa | 2280 |
| tagaaaatgg gggtacatag tggatgaaaa aagtgatgtt agctacggct ttgtttttag | 2340 |
| gattgactcc agctggcgcg aacgcagctg atttaggcca ccagacgttg ggatccaatg | 2400 |
| atggctgggg cgcgtactcg accggcacga caggcggatc aaaagcatcc tcctcaaatg | 2460 |

```
tgtataccgt cagcaacaga aaccagcttg tctcggcatt agggaaggaa acgaacacaa    2520
cgccaaaaat catttatatc aagggaacga ttgacatgaa cgtggatgac aatctgaagc    2580
cgcttggcct aaatgactat aaagatccgg agtatgattt ggacaaatat ttgaaagcct    2640
atgatcctag cacatggggc aaaaaagagc cgtcgggaac acaagaagaa gcgagagcac    2700
gctctcagaa aaaccaaaaa gcacgggtca tggtggatat ccctgcaaac acgacgatcg    2760
tcggttcagg gactaacgct aaagtcgtgg aggaaacttc caaatcaag agtgataacg     2820 tcattattcg caacattgaa ttccaggatg cctatgacta ttttccgcaa tggttgtaaa    2880
acgacggcca gtgaattctg atcaaatggt tcagtgagag cgaagcgaac acttgatttt    2940
ttaattttct atcttttata ggtcattaga gtatacttat ttgtcctata aactatttag    3000
cagcataata gatttattga ataggtcatt taagttgagc atattagagg aggaaaatct    3060
tggagaaata tttgaagaac ccgagatcta gatcaggtac cgcaacgttc gcagatgctg    3120
ctgaagagat tattaaaaag ctgaaagcaa aaggctatca attggtaact gtatctcagc    3180
ttgaagaagt gaagaagcag agaggctatt gaataaatga gtagaaagcg ccatatcggc    3240
gcttttcttt tggaagaaaa tagggaaa tggtacttg ttaaaaattc ggaatattta       3300
tacaatatca tatgtatcac attgaaagga ggggcctgct gtccagactg tccgctgtgt    3360
aaaaataagg aataaagggg ggttgacatt attttactga tatgtataat ataatttgta    3420
taagaaaatg gaggggccct cgaaacgtaa gatgaaacct tagataaaag tgcttttttt    3480
gttgcaattg aagaattatt aatgttaagc ttaattaaag ataatatctt tgaattgtaa    3540
cgcccctcaa aagtaagaac tacaaaaaaa gaatacgtta tatagaaata tgtttgaacc    3600
ttcttcagat tacaaatata ttcggacgga ctctacctca aatgcttatc taactataga    3660
atgacataca agcacaacct tgaaaatttg aaaatataac taccaatgaa cttgttcatg    3720
tgaattatcg ctgtatttaa ttttctcaat tcaatatata atatgccaat acattgttac    3780
aagtagaaat taagacaccc ttgatagcct tactatacct aacatgatgt agtattaaat    3840
gaatatgtaa atatatttat gataagaagc gacttattta taatcattac atattttct    3900 attggaatga ttaagattcc aatagaatag tgtataaatt atttatcttg aaaggaggga    3960
tgcctaaaaa cgaagaacat taaaaacata tatttgcacc gtctaatgga tttatgaaaa    4020 atcatttat cagtttgaaa attatgtatt atggagctct gaaaaaaagg agaggataaa     4080
gagaaagggg gatcggaaaa caagtatata ggaggagacc tatttatggc ttcagaaaaa    4140
gacgcaggaa aacagtcagc agtaaagctt gttccattgc ttattactgt cgctgtggga    4200
ctaatcatct ggtttattcc cgctccgtcc ggacttgaac ctaaagcttg gcatttgttt    4260 gcgattttg tcgcaacaat tatcggcttt atctccaagc ccttgccaat gggtgcaatt    4320 gcaattttg cattggcggt tactgcacta actggaacac tatcaattga ggatacatta    4380
agcggattcg ggaataagac catttggctt atcgttatcg cattctttat ttcccggga    4440 tttatcaaaa ccggtctcgg tgcgagaatt tcgtatgtat tcgttcagaa attcggaaaa    4500 aaaaccctg gactttctta ttcactgcta ttcagtgatt taatactttc acctgctatt    4560
ccaagtaata cggcgcgtgc aggaggcatt atatttccta ttatcagatc attatccgaa    4620
acattcggat caagcccggc aaatggaaca gagagaaaaa tcgtgcatt cttattaaaa    4680 accggttttc aggggaatct gatcacatct gctatgttcc tgacagcgat ggcggcgaac    4740
ccgctgattg ccaagctggc ccatgatgtc gcaggggtgg acttaacatg acaagctgg    4800 gcaattgccg cgattgtacc gggacttgta agcttaatca tcacgccgct tgtgatttac    4860
```

```
aaactgtatc cgccggaaat caaagaaaca ccggatgcgg cgaaaatcgc aacagaaaaa    4920
ctgaaagaaa tgggaccgtt caaaaaatcg gagctttcca tggttatcgt gtttcttttg    4980
gtgcttgtgc tgtggatttt tggcggcagc ttcaacatcg acgctaccac aaccgcattg    5040
atcggtttgg ccgttctctt attatcacaa gttctgactt gggatgatat caagaaagaa    5100
cagggcgctt gggatacgct cacttggttt gcggcgcttg tcatgctcgc caacttcttg    5160
aatgaattag gcatggtgtc ttggttcagt aatgccatga aatcatccgt atcagggttc    5220
tcttggattg tggcattcat cattttaatt gttgtgtatt attactctca ctatttcttt    5280
gcaagtgcga cagcccacat cagtgcgatg tattcagcat ttttggctgt cgtcgtggca    5340
gcgggcgcac cgccgctttt agcagcgctg agcctcgcgt tcatcagcaa cctgttcggg    5400
tcaacgactc actacggttc tggagcggct ccggtcttct tcggagcagg ctacatcccg    5460
caaggcaaat ggtggtccat cggatttatc ctgtcgattg ttcatatcat cgtatggctt    5520
gtgatcggcg gattatggtg gaaagtacta ggaatatggt agaaagaaaa aggcagacgc    5580
ggtctgcctt ttttattttt cactccttcg taagaaaatg gattttgaaa aatgagaaaa    5640
ttccctgtga aaaatggtat gatctaggta gaaaggacgg ctggtgctgt ggtgaaaaag    5700
cggttccatt tttccctg                                                  5718

<210> SEQ ID NO 23
<211> LENGTH: 27
<212> TYPE: DNA
<213> ORGANISM: Artificial sequence
<220> FEATURE:
<223> OTHER INFORMATION: Primer 1605

<400> SEQUENCE: 23
gacggccagt gaattcgata aaagtgc                                          27

<210> SEQ ID NO 24
<211> LENGTH: 42
<212> TYPE: DNA
<213> ORGANISM: Artificial sequence
<220> FEATURE:
<223> OTHER INFORMATION: Primer 1606
<220> FEATURE:
<221> NAME/KEY: misc_feature
<222> LOCATION: (13)..(13)
<223> OTHER INFORMATION: n is a, c, g, or t
<220> FEATURE:
<221> NAME/KEY: misc_feature
<222> LOCATION: (16)..(16)
<223> OTHER INFORMATION: n is a, c, g, or t

<400> SEQUENCE: 24
ccagatctct atnktnktgt acggagtcta actccccaag ag                         42

<210> SEQ ID NO 25
<211> LENGTH: 1112
<212> TYPE: DNA
<213> ORGANISM: Nocardiopsis dassonvillei DSM 43235

<400> SEQUENCE: 25
gcttttagtt catcgatcgc atcggctgct ccggcccccg tcccccagac ccccgtcgcc     60
gacgacagcg ccgccagcat gaccgaggcg ctcaagcgcg acctcgacct cacctcggcc    120
gaggccgagg agcttctctc ggcgcaggaa gccgccatcg agaccgacgc cgaggccacc    180
gaggccgcgg gcgaggccta cggcggctca ctgttcgaca ccgagaccct cgaactcacc    240
gtgctggtca ccgacgcctc cgccgtcgag gcggtcgagg ccaccggagc ccaggccacc    300
```

-continued

```
gtcgtctccc acggcaccga gggcctgacc gaggtcgtgg aggacctcaa cggcgccgag    360
gttcccgaga gcgtcctcgg ctggtacccg gacgtggaga gcgacaccgt cgtggtcgag    420
gtgctggagg ctccgacgc cgacgtcgcc gccctgctcg ccgacgccgg tgtggactcc    480
tcctcggtcc gggtggagga ggccgaggag gccccgcagg tctacgccga catcatcggc    540
ggcctggcct actacatggg cggccgctgc tccgtcggct cgccgcgac caacagcgcc    600 ggtcagcccg gtttcgtcac cgccggccac tgcggcaccg tcggcaccgg cgtgaccatc    660
ggcaacggca ccggcacctt ccagaactcg gtcttcccg gcaacgacgc cgccttcgtc    720
cgcggcacct ccaacttcac cctgaccaac ctggtctcgc gctacaactc cggcggctac    780
cagtcggtga ccggtaccag ccaggccccg gccggctcgg ccgtgtgccg ctccggctcc    840
accaccggct ggcactgcgg caccatccag gcccgcaacc agaccgtgcg ctacccgcag    900
ggcaccgtct actcgctcac ccgcaccaac gtgtgcgccg agcccggcga ctccggcggt    960
tcgttcatct ccggctcgca ggcccagggc gtcacctccg cgggctccgg caactgctcc   1020
gtcggcggca cgacctacta ccaggaggtc accccgatga tcaactcctg gggtgtcagg   1080
atccggacct aatcgcatgt tcaatccgct cc                                 1112
```

<210> SEQ ID NO 26
<211> LENGTH: 48
<212> TYPE: DNA
<213> ORGANISM: Artificial sequence
<220> FEATURE:
<223> OTHER INFORMATION: Primer 1423

<400> SEQUENCE: 26

```
gcttttagtt catcgatcgc atcggctgct ccggcccccg tcccccag                  48
```

<210> SEQ ID NO 27
<211> LENGTH: 45
<212> TYPE: DNA
<213> ORGANISM: Artificial sequence
<220> FEATURE:
<223> OTHER INFORMATION: Primer 1475

<400> SEQUENCE: 27

```
ggagcggatt gaacatgcga ttaggtccgg atcctgacac cccag                     45
```

<210> SEQ ID NO 28
<211> LENGTH: 354
<212> TYPE: PRT
<213> ORGANISM: Nocardiopsis dassonvillei DSM 43235
<220> FEATURE:
<221> NAME/KEY: PROPEP
<222> LOCATION: (1)..(166)
<220> FEATURE:
<221> NAME/KEY: mat_peptide
<222> LOCATION: (167)..(354)

<400> SEQUENCE: 28

```
Ala Pro  Ala Pro Val Pro Gln  Thr Pro Val Ala Asp  Asp Ser Ala
    -165                -160                -155

Ala Ser  Met Thr Glu Ala Leu  Lys Arg Asp Leu Asp  Leu Thr Ser
    -150                -145                -140

Ala Glu  Ala Glu Glu Leu Leu  Ser Ala Gln Glu Ala  Ala Ile Glu
    -135                -130                -125

Thr Asp  Ala Glu Ala Thr Glu  Ala Ala Gly Glu Ala  Tyr Gly Gly
    -120                -115                -110

Ser Leu  Phe Asp Thr Glu Thr  Leu Glu Leu Thr Val  Leu Val Thr Asp
```

```
              -105              -100               -95
Ala Ser Ala Val Glu Ala Val Glu Ala Thr Gly Ala Gln Ala Thr Val
-90              -85                   -80                  -75

Val Ser His Gly Thr Glu Gly Leu Thr Glu Val Val Glu Asp Leu Asn
                -70                   -65                  -60

Gly Ala Glu Val Pro Glu Ser Val Leu Gly Trp Tyr Pro Asp Val Glu
                -55                   -50                  -45

Ser Asp Thr Val Val Val Glu Val Leu Glu Gly Ser Asp Ala Asp Val
        -40                   -35                  -30

Ala Ala Leu Leu Ala Asp Ala Gly Val Asp Ser Ser Val Arg Val
    -25                  -20                  -15

Glu Glu Ala Glu Ala Pro Gln Val Tyr Ala Asp Ile Ile Gly Gly
-10              -5                  -1   1               5

Leu Ala Tyr Tyr Met Gly Gly Arg Cys Ser Val Gly Phe Ala Ala Thr
            10                  15                  20

Asn Ser Ala Gly Gln Pro Gly Phe Val Thr Ala Gly His Cys Gly Thr
            25                  30                  35

Val Gly Thr Gly Val Thr Ile Gly Asn Gly Thr Gly Thr Phe Gln Asn
    40                  45                  50

Ser Val Phe Pro Gly Asn Asp Ala Ala Phe Val Arg Gly Thr Ser Asn
55              60                  65                  70

Phe Thr Leu Thr Asn Leu Val Ser Arg Tyr Asn Ser Gly Gly Tyr Gln
                75                  80                  85

Ser Val Thr Gly Thr Ser Gln Ala Pro Ala Gly Ser Ala Val Cys Arg
                90                  95                  100

Ser Gly Ser Thr Thr Gly Trp His Cys Gly Thr Ile Gln Ala Arg Asn
            105                 110                 115

Gln Thr Val Arg Tyr Pro Gln Gly Thr Val Tyr Ser Leu Thr Arg Thr
    120                 125                 130

Asn Val Cys Ala Glu Pro Gly Asp Ser Gly Gly Ser Phe Ile Ser Gly
135             140                 145                 150

Ser Gln Ala Gln Gly Val Thr Ser Gly Gly Ser Gly Asn Cys Ser Val
            155                 160                 165

Gly Gly Thr Thr Tyr Tyr Gln Glu Val Thr Pro Met Ile Asn Ser Trp
            170                 175                 180

Gly Val Arg Ile Arg Thr
            185

<210> SEQ ID NO 29
<211> LENGTH: 498
<212> TYPE: DNA
<213> ORGANISM: Nocardiopsis dassonvillei DSM 43235

<400> SEQUENCE: 29
gctccggccc ccgtccccca gaccccgtc gccgacgaca cgccgccag catgaccgag      60 gcgctcaagc gcgacctcga cctcacctcg gccgaggccg aggagcttct ctcggcgcag    120
gaagccgcca tcgagaccga cgccgaggcc accgaggccg cggcgaggc ctacggcggc    180 tcactgttcg acaccgagac cctcgaactc accgtgctgg tcaccgacgc ctccgccgtc    240
gaggcggtcg aggccaccgg agcccaggcc accgtcgtct cccacggcac cgagggcctg    300
accgaggtcg tggaggacct caacggcgcc gaggttcccg agagcgtcct cggctggtac    360
ccggacgtgg agagcgacac cgtcgtggtc gaggtgctgg agggctccga cgccgacgtc    420
gccgccctgc tcgccgacgc cggtgtggac tcctcctcgg tccgggtgga ggaggccgag    480
```

```
gaggccccgc aggtctac                                                  498
```

<210> SEQ ID NO 30
<211> LENGTH: 166
<212> TYPE: PRT
<213> ORGANISM: Nocardiopsis dassonvillei DSM 43235

<400> SEQUENCE: 30

```
Ala Pro Ala Pro Val Pro Gln Thr Pro Val Ala Asp Asp Ser Ala Ala
1               5                   10                  15

Ser Met Thr Glu Ala Leu Lys Arg Asp Leu Asp Leu Thr Ser Ala Glu
            20                  25                  30

Ala Glu Glu Leu Leu Ser Ala Gln Glu Ala Ala Ile Glu Thr Asp Ala
        35                  40                  45

Glu Ala Thr Glu Ala Ala Gly Glu Ala Tyr Gly Gly Ser Leu Phe Asp
    50                  55                  60

Thr Glu Thr Leu Glu Leu Thr Val Leu Val Thr Asp Ala Ser Ala Val
65                  70                  75                  80

Glu Ala Val Glu Ala Thr Gly Ala Gln Ala Thr Val Val Ser His Gly
                85                  90                  95

Thr Glu Gly Leu Thr Glu Val Val Glu Asp Leu Asn Gly Ala Glu Val
            100                 105                 110

Pro Glu Ser Val Leu Gly Trp Tyr Pro Asp Val Glu Ser Asp Thr Val
        115                 120                 125

Val Val Glu Val Leu Glu Gly Ser Asp Ala Asp Val Ala Ala Leu Leu
    130                 135                 140

Ala Asp Ala Gly Val Asp Ser Ser Ser Val Arg Val Glu Glu Ala Glu
145                 150                 155                 160

Glu Ala Pro Gln Val Tyr
                165
```

<210> SEQ ID NO 31
<211> LENGTH: 1146
<212> TYPE: DNA
<213> ORGANISM: Artificial sequence
<220> FEATURE:
<223> OTHER INFORMATION: The DNA sequence coding for the pro-region of
      SEQ ID NO: 29 fused in frame to A1918L2 protease tail-variant
      encoding gene; whole construct: 10R(proA1918L2).

<400> SEQUENCE: 31

```
atgaagaaac cgttggggaa aattgtcgca agcaccgcac tactcatttc tgttgctttt    60
agttcatcga tcgcatcggc tgctccggcc cccgtccccc agaccccgt cgccgacgac    120 agcgccgcca gcatgaccga ggcgctcaag cgcgacctcg acctcacctc ggccgaggcc    180
gaggagcttc tctcggcgca ggaagccgcc atcgagaccg acgccgaggc caccgaggcc    240
gcgggcgagg cctacggcgg ctcactgttc gacaccgaga ccctcgaact caccgtgctg    300
gtcaccgacg cctccgccgt cgaggcgtc gaggccaccg gagcccaggc caccgtcgtc    360
tcccacggca ccgagggcct gaccgaggtc gtggaggacc tcaacggcgc cgaggttccc    420
gagagcgtcc tcggctggta cccggacgtg gagagcgaca ccgtcgtggt cgaggtgctg    480
gagggctccg acgccgacgt cgccgccctg ctcgccgacg ccggtgtgga ctcctcctcg    540
gtccgggtgg aggaggccga ggaggccccg caggtctatg ccgatatcat ggaggccta    600 gcgtacacaa tgggtggtcg ctgcagcgta ggatttgcag ccacaaatgc agctggacaa    660
cctggcttcg tgacagctgg acattgcggc gcgtcggta cacaggttac tatcggcaat    720
ggaagaggtg tctttgagca aagcgtattt cccgggaatg atgctgcctt cgttagaggt    780
```

```
acgtccaact ttacgcttac taacttagta tctagataca acactggcgg atatgcaact      840
gtagcaggtc acaatcaagc acctattggc tctagcgtct gccgctcagg gtcgactaca      900
ggatggcatt gtggaaccat tcaagctaga ggtcagagcg tgagctatcc tgaaggtacc      960
gtaacgaaca tgactcgtac gactgtatgt gcagaaccag gtgactctgg aggttcatat     1020
atcagcggta cgcaagcgca aggcgttacc tcaggtggat ccggtaactg taggacaggt     1080
ggcacaacgt tctaccagga agtgacaccg atggtgaact cttggggagt tagactccgt     1140
acataa                                                                1146
```

<210> SEQ ID NO 32
<211> LENGTH: 1068
<212> TYPE: DNA
<213> ORGANISM: Nocardiopsis Alba DSM 15647

<400> SEQUENCE: 32

```
gcgaccggcc ccctccccca gtcccccacc ccggatgaag ccgaggccac caccatggtc       60
gaggccctcc agcgcgacct cggcctgtcc cctctcagg ccgacgagct cctcgaggcg      120
caggccgagt ccttcgagat cgacgaggcc gccaccgcgg ccgcagccga ctcctacggc      180
ggctccatct tcgacaccga cagcctcacc ctgaccgtcc tggtcaccga cgcctccgcc      240
gtcgaggcgg tcgaggccgc cggcgccgag gccaaggtgg tctcgcacgg catggagggc      300
ctggaggaga tcgtcgccga cctgaacgcg gccgacgctc agcccggcgt cgtgggctgg      360
taccccgaca tccactccga cacggtcgtc ctcgaggtcc tcgagggctc cggtgccgac      420
gtggactccc tgctcgccga cgccggtgtg gacaccgccg acgtcaaggt ggagagcacc      480
accgagcagc ccgagctgta cgccgacatc atcggcggtc tcgcctacac catgggtggg      540
cgctgctcgg tcggcttcgc ggccaccaac gcctccggcc agcccgggtt cgtcaccgcc      600
ggccactgcg gcaccgtcgg caccccggtc agcatcggca acggccaggg cgtcttcgag      660
cgttccgtct tccccggcaa cgactccgcc ttcgtccgcg gcacctcgaa cttcacccctg     720 accaacctgg tcagccgcta caacaccggt ggttacgcga ccgtctccgg ctcctcgcag      780
gcggcgatcg gctcgcagat ctgccgttcc ggctccacca ccggctggca ctgcggcacc      840
gtccaggccc gcggccagac ggtgagctac ccccagggca ccgtgcagaa cctgacccgc      900
accaacgtct gcgccgagcc cggtgactcc ggcggctcct tcatctccgg cagccaggcc      960
cagggcgtca cctccggtgg ctccggcaac tgctccttcg gtggcaccac ctactaccag     1020
gaggtcaacc cgatgctgag cagctggggt ctgaccctgc gcacctga                  1068
```

<210> SEQ ID NO 33
<211> LENGTH: 355
<212> TYPE: PRT
<213> ORGANISM: Nocardiopsis Alba DSM 15647
<220> FEATURE:
<221> NAME/KEY: PROPEP
<222> LOCATION: (1)..(167)
<220> FEATURE:
<221> NAME/KEY: mat_peptide
<222> LOCATION: (168)..(355)

<400> SEQUENCE: 33

Ala Thr Gly  Pro Leu Pro Gln Ser  Pro Thr Pro Asp Glu  Ala Glu
         -165                -160               -155

Ala Thr Thr  Met Val Glu Ala Leu  Gln Arg Asp Leu Gly  Leu Ser
         -150                -145               -140

Pro Ser Gln  Ala Asp Glu Leu Leu  Glu Ala Gln Ala Glu  Ser Phe

```
                -135            -130             -125
Glu Ile Asp Glu Ala Ala Thr Ala Ala Ala Ala Asp Ser Tyr Gly
        -120            -115            -110

Gly Ser Ile Phe Asp Thr Asp Ser Leu Thr Leu Thr Val Leu Val Thr
        -105            -100             -95

Asp Ala Ser Ala Val Glu Ala Val Glu Ala Ala Gly Ala Glu Ala Lys
    -90             -85             -80

Val Val Ser His Gly Met Glu Gly Leu Glu Glu Ile Val Ala Asp Leu
-75              -70              -65              -60

Asn Ala Ala Asp Ala Gln Pro Gly Val Val Gly Trp Tyr Pro Asp Ile
            -55             -50             -45

His Ser Asp Thr Val Val Leu Glu Val Leu Glu Gly Ser Gly Ala Asp
            -40             -35             -30

Val Asp Ser Leu Leu Ala Asp Ala Gly Val Asp Thr Ala Asp Val Lys
        -25             -20             -15

Val Glu Ser Thr Thr Glu Gln Pro Glu Leu Tyr Ala Asp Ile Ile Gly
    -10              -5              -1   1               5

Gly Leu Ala Tyr Thr Met Gly Gly Arg Cys Ser Val Gly Phe Ala Ala
                10               15               20

Thr Asn Ala Ser Gly Gln Pro Gly Phe Val Thr Ala Gly His Cys Gly
            25              30              35

Thr Val Gly Thr Pro Val Ser Ile Gly Asn Gly Gln Gly Val Phe Glu
        40              45              50

Arg Ser Val Phe Pro Gly Asn Asp Ser Ala Phe Val Arg Gly Thr Ser
    55              60              65

Asn Phe Thr Leu Thr Asn Leu Val Ser Arg Tyr Asn Thr Gly Tyr
70              75              80              85

Ala Thr Val Ser Gly Ser Ser Gln Ala Ala Ile Gly Ser Gln Ile Cys
            90              95              100

Arg Ser Gly Ser Thr Thr Gly Trp His Cys Gly Thr Val Gln Ala Arg
            105             110             115

Gly Gln Thr Val Ser Tyr Pro Gln Gly Thr Val Gln Asn Leu Thr Arg
            120             125             130

Thr Asn Val Cys Ala Glu Pro Gly Asp Ser Gly Gly Ser Phe Ile Ser
    135             140             145

Gly Ser Gln Ala Gln Gly Val Thr Ser Gly Gly Ser Gly Asn Cys Ser
150             155             160             165

Phe Gly Gly Thr Thr Tyr Tyr Gln Glu Val Asn Pro Met Leu Ser Ser
            170             175             180

Trp Gly Leu Thr Leu Arg Thr
            185

<210> SEQ ID NO 34
<211> LENGTH: 43
<212> TYPE: DNA
<213> ORGANISM: Artificial sequence
<220> FEATURE:
<223> OTHER INFORMATION: Primer 1421

<400> SEQUENCE: 34
gttcatcgat cgcatcggct gcgaccggcc ccctccccca gtc                    43

<210> SEQ ID NO 35
<211> LENGTH: 31
<212> TYPE: DNA
<213> ORGANISM: Artificial sequence
<220> FEATURE:
```

-continued

<223> OTHER INFORMATION: Primer 1604

<400> SEQUENCE: 35
gcggatccta tcaggtgcgc agggtcagac c                31

<210> SEQ ID NO 36
<211> LENGTH: 1062
<212> TYPE: DNA
<213> ORGANISM: Nocardiopsis prasina DSM 15648

<400> SEQUENCE: 36

```
gccaccggac cgctccccca gtcacccacc ccggaggccg acgccgtctc catgcaggag      60
gcgctccagc gcgacctcgg cctgaccccg cttgaggccg atgaactgct ggccgcccag     120
gacaccgcct tcgaggtcga cgaggccgcg gccgcggccg ccggggacgc ctacggcggc     180
tccgtcttcg acaccgagac cctggaactg accgtcctgg tcaccgacgc cgcctcggtc     240
gaggctgtgg aggccaccgg cgcgggtacc gaactcgtct cctacggcat cgagggcctc     300
gacgagatca tccaggatct caacgccgcc gacgccgtcc ccggcgtggt cggctggtac     360
ccggacgtgg cgggtgacac cgtcgtcctg gaggtcctgg agggttccgg agccgacgtg     420
agcggcctgc tcgccgacgc cggcgtggac gcctcggccg tcgaggtgac cagcagtgcg     480
cagcccgagc tctacgccga catcatcggc ggtctggcct acaccatggg cggccgctgt     540
tcggtcggat tcgcggccac caacgccgcc ggtcagcccg gattcgtcac cgccggtcac     600
tgtggccgcg tgggcaccca ggtgagcatc ggcaacggcc agggcgtctt cgagcagtcc     660
atcttcccgg gcaacgacgc cgccttcgtc cgcggcacgt ccaacttcac gctgaccaac     720
ctggtcagcc gctacaacac cggcggttac gccaccgtcg ccggccacaa ccaggcgccc     780
atcggctcct ccgtctgccg ctccggctcc accaccggct ggcactgcgg caccatccag     840
gcccgcggcc agtcggtgag ctaccccgag ggcaccgtca ccaacatgac ccggaccacc     900
gtgtgcgccg agcccggcga ctccggcggc tcctacatct ccggcaacca ggcccagggc     960
gtcacctccg gcggctccgg caactgccgc accggcggga ccaccttcta ccaggaggtc    1020
accccccatgg tgaactcctg gggcgtccgt ctccggacct aa                      1062
```

<210> SEQ ID NO 37
<211> LENGTH: 353
<212> TYPE: PRT
<213> ORGANISM: Nocardiopsis prasina DSM 15648
<220> FEATURE:
<221> NAME/KEY: PROPEP
<222> LOCATION: (1)..(165)
<220> FEATURE:
<221> NAME/KEY: mat_peptide
<222> LOCATION: (166)..(353)

<400> SEQUENCE: 37

```
Ala Thr Gly Pro Leu Pro Gln Ser Pro Thr Pro Glu Ala Asp Ala
-165                -160                -155

Val Ser Met Gln Glu Ala Leu Gln Arg Asp Leu Gly Leu Thr Pro
-150                -145                -140

Leu Glu Ala Asp Glu Leu Leu Ala Ala Gln Asp Thr Ala Phe Glu
-135                -130                -125

Val Asp Glu Ala Ala Ala Ala Ala Ala Gly Asp Ala Tyr Gly Gly
-120                -115                -110

Ser Val Phe Asp Thr Glu Thr Leu Glu Leu Thr Val Leu Val Thr Asp
-105                -100                -95                 -90

Ala Ala Ser Val Glu Ala Val Glu Ala Thr Gly Ala Gly Thr Glu Leu
```

```
                    -85              -80                  -75
Val Ser Tyr Gly Ile Glu Gly Leu Asp Glu Ile Ile Gln Asp Leu Asn
            -70              -65                  -60

Ala Ala Asp Ala Val Pro Gly Val Gly Trp Tyr Pro Asp Val Ala
        -55              -50                  -45

Gly Asp Thr Val Val Leu Glu Val Leu Glu Gly Ser Gly Ala Asp Val
    -40              -35                  -30

Ser Gly Leu Leu Ala Asp Ala Gly Val Asp Ala Ser Ala Val Glu Val
-25              -20                  -15                  -10

Thr Ser Ser Ala Gln Pro Glu Leu Tyr Ala Asp Ile Ile Gly Gly Leu
             -5               -1  1                 5

Ala Tyr Thr Met Gly Gly Arg Cys Ser Val Gly Phe Ala Ala Thr Asn
             10              15                 20

Ala Ala Gly Gln Pro Gly Phe Val Thr Ala Gly His Cys Gly Arg Val
             25              30                 35

Gly Thr Gln Val Ser Ile Gly Asn Gly Gln Gly Val Phe Glu Gln Ser
40               45              50                 55

Ile Phe Pro Gly Asn Asp Ala Ala Phe Val Arg Gly Thr Ser Asn Phe
             60              65                 70

Thr Leu Thr Asn Leu Val Ser Arg Tyr Asn Thr Gly Gly Tyr Ala Thr
             75              80                 85

Val Ala Gly His Asn Gln Ala Pro Ile Gly Ser Ser Val Cys Arg Ser
             90              95                100

Gly Ser Thr Thr Gly Trp His Cys Gly Thr Ile Gln Ala Arg Gly Gln
105              110             115

Ser Val Ser Tyr Pro Glu Gly Thr Val Thr Asn Met Thr Arg Thr Thr
120              125             130                135

Val Cys Ala Glu Pro Gly Asp Ser Gly Gly Ser Tyr Ile Ser Gly Asn
                 140             145                150

Gln Ala Gln Gly Val Thr Ser Gly Gly Ser Gly Asn Cys Arg Thr Gly
                 155             160                165

Gly Thr Thr Phe Tyr Gln Glu Val Thr Pro Met Val Asn Ser Trp Gly
                 170             175                180

Val Arg Leu Arg Thr
        185

<210> SEQ ID NO 38
<211> LENGTH: 43
<212> TYPE: DNA
<213> ORGANISM: Artificial sequence
<220> FEATURE:
<223> OTHER INFORMATION: Primer 1346

<400> SEQUENCE: 38
gttcatcgat cgcatcggct gccaccggac cgctccccca gtc                    43

<210> SEQ ID NO 39
<211> LENGTH: 38
<212> TYPE: DNA
<213> ORGANISM: Artificial sequence
<220> FEATURE:
<223> OTHER INFORMATION: Primer 1602

<400> SEQUENCE: 39
gcggatccta ttaggtccgg agacggacgc cccaggag                          38

<210> SEQ ID NO 40
<211> LENGTH: 1062
```

```
<212> TYPE: DNA
<213> ORGANISM: Nocardiopsis prasina DSM 15649

<400> SEQUENCE: 40
gccaccggac cactccccca gtcacccacc ccggaggccg acgccgtctc catgcaggag      60
gcgctccagc gcgacctcgg cctgaccccg cttgaggccg atgaactgct ggccgcccag     120
gacaccgcct tcgaggtcga cgaggccgcg gccgaggccg ccggtgacgc ctacggcggc     180
tccgtcttcg acaccgagac cctggaactg accgtcctgg tcaccgactc cgccgcggtc     240
gaggcggtgg aggccaccgg cgccgggacc gaactggtct cctacggcat cacgggcctc     300
gacgagatcg tcgaggagct caacgccgcc gacgccgttc ccggcgtggt cggctggtac     360
ccggacgtcg cgggtgacac cgtcgtgctg gaggtcctgg agggttccgg cgccgacgtg     420
ggcggcctgc tcgccgacgc cggcgtggac gcctcggcgg tcgaggtgac caccaccgag     480
cagcccgagc tgtacgccga catcatcggc ggtctggcct acaccatggg cggccgctgt     540
tcggtcggct tcgcggccac caacgccgcc ggtcagcccg ggttcgtcac cgccggtcac     600
tgtggccgcg tgggcaccca ggtgaccatc ggcaacggcc ggggcgtctt cgagcagtcc     660
atcttcccgg gcaacgacgc cgccttcgtc cgcggaacgt ccaacttcac gctgaccaac     720
ctggtcagcc gctacaacac cggcggctac gccaccgtcg ccggtcacaa ccaggcgccc     780
atcggctcct ccgtctgccg ctccggctcc accaccggtt ggcactgcgg caccatccag     840
gcccgcggcc agtcggtgag ctaccccgag ggcaccgtca ccaacatgac gcggaccacc     900
gtgtgcgccg agcccggcga ctccggcggc tcctacatct ccggcaacca ggcccagggc     960
gtcacctccg gcggctccgg caactgccgc accggcggga ccaccttcta ccaggaggtc    1020 accccccatgg tgaactcctg gggcgtccgt ctccggacct aa                      1062

<210> SEQ ID NO 41
<211> LENGTH: 353
<212> TYPE: PRT
<213> ORGANISM: Nocardiopsis prasina DSM 15649
<220> FEATURE:
<221> NAME/KEY: PROPEP
<222> LOCATION: (1)..(165)
<220> FEATURE:
<221> NAME/KEY: mat_peptide
<222> LOCATION: (166)..(353)

<400> SEQUENCE: 41

Ala  Thr  Gly  Pro  Leu  Pro  Gln  Ser  Pro  Thr  Pro  Glu  Ala  Asp  Ala
-165                 -160                 -155

Val  Ser  Met  Gln  Glu  Ala  Leu  Gln  Arg  Asp  Leu  Gly  Leu  Thr  Pro
-150                 -145                 -140

Leu  Glu  Ala  Asp  Glu  Leu  Leu  Ala  Ala  Gln  Asp  Thr  Ala  Phe  Glu
-135                 -130                 -125

Val  Asp  Glu  Ala  Ala  Ala  Glu  Ala  Ala  Gly  Asp  Ala  Tyr  Gly  Gly
-120                 -115                 -110

Ser  Val  Phe  Asp  Thr  Glu  Thr  Leu  Glu  Leu  Thr  Val  Leu  Val  Thr  Asp
-105                 -100                 -95                        -90

Ser  Ala  Ala  Val  Glu  Ala  Val  Glu  Ala  Thr  Gly  Ala  Gly  Thr  Glu  Leu
                -85                  -80                  -75

Val  Ser  Tyr  Gly  Ile  Thr  Gly  Leu  Asp  Glu  Ile  Val  Glu  Glu  Leu  Asn
                -70                  -65                  -60

Ala  Ala  Asp  Ala  Val  Pro  Gly  Val  Val  Gly  Trp  Tyr  Pro  Asp  Val  Ala
                -55                  -50                  -45

Gly  Asp  Thr  Val  Val  Leu  Glu  Val  Leu  Glu  Gly  Ser  Gly  Ala  Asp  Val
```

```
                -40                 -35                 -30
Gly Gly Leu Leu Ala Asp Ala Gly Val Asp Ala Ser Ala Val Glu Val
    -25                 -20                 -15                 -10

Thr Thr Thr Glu Gln Pro Glu Leu Tyr Ala Asp Ile Ile Gly Gly Leu
                -5                  -1  1                   5

Ala Tyr Thr Met Gly Gly Arg Cys Ser Val Gly Phe Ala Ala Thr Asn
            10                  15                  20

Ala Ala Gly Gln Pro Gly Phe Val Thr Ala Gly His Cys Gly Arg Val
            25                  30                  35

Gly Thr Gln Val Thr Ile Gly Asn Gly Arg Gly Val Phe Glu Gln Ser
40                  45                  50                  55

Ile Phe Pro Gly Asn Asp Ala Ala Phe Val Arg Gly Thr Ser Asn Phe
                60                  65                  70

Thr Leu Thr Asn Leu Val Ser Arg Tyr Asn Thr Gly Gly Tyr Ala Thr
                75                  80                  85

Val Ala Gly His Asn Gln Ala Pro Ile Gly Ser Ser Val Cys Arg Ser
                90                  95                  100

Gly Ser Thr Thr Gly Trp His Cys Gly Thr Ile Gln Ala Arg Gly Gln
    105                 110                 115

Ser Val Ser Tyr Pro Glu Gly Thr Val Thr Asn Met Thr Arg Thr Thr
120                 125                 130                 135

Val Cys Ala Glu Pro Gly Asp Ser Gly Ser Tyr Ile Ser Gly Asn
                140                 145                 150

Gln Ala Gln Gly Val Thr Ser Gly Gly Ser Asn Cys Arg Thr Gly
            155                 160                 165

Gly Thr Thr Phe Tyr Gln Glu Val Thr Pro Met Val Asn Ser Trp Gly
            170                 175                 180

Val Arg Leu Arg Thr
    185

<210> SEQ ID NO 42
<211> LENGTH: 43
<212> TYPE: DNA
<213> ORGANISM: Artificial sequence
<220> FEATURE:
<223> OTHER INFORMATION: Primer 1603

<400> SEQUENCE: 42
gttcatcgat cgcatcggct gccaccggac cactccccca gtc                    43

<210> SEQ ID NO 43
<211> LENGTH: 353
<212> TYPE: PRT
<213> ORGANISM: Nocardiopsis sp. NRRL 18262
<220> FEATURE:
<221> NAME/KEY: PROPEP
<222> LOCATION: (1)..(165)
<220> FEATURE:
<221> NAME/KEY: mat_peptide
<222> LOCATION: (166)..(1059)

<400> SEQUENCE: 43

Ala  Thr Gly Ala Leu Pro  Gln Ser Pro Thr Pro  Glu Ala Asp Ala
-165             -160                -155

Val  Ser Met Gln Glu Ala  Leu Gln Arg Asp Leu  Asp Leu Thr Ser
-150             -145                -140

Ala  Glu Ala Glu Glu Leu  Leu Ala Ala Gln Asp  Thr Ala Phe Glu
-135             -130                -125

Val  Asp Glu Ala Ala Ala  Glu Ala Ala Gly Asp  Ala Tyr Gly Gly
```

```
                -120              -115              -110
Ser   Val Phe Asp Thr Glu   Ser Leu Glu Leu Thr Val Leu Val Thr Asp
-105              -100               -95              -90

Ala Ala Ala Val Glu Ala Val Glu Ala Thr Gly Ala Gly Thr Glu Leu
            -85              -80              -75

Val Ser Tyr Gly Ile Asp Gly Leu Asp Glu Ile Val Gln Glu Leu Asn
            -70              -65              -60

Ala Ala Asp Ala Val Pro Gly Val Val Gly Trp Tyr Pro Asp Val Ala
            -55              -50              -45

Gly Asp Thr Val Val Leu Glu Val Leu Glu Ser Gly Ala Asp Val
        -40              -35              -30

Ser Gly Leu Leu Ala Asp Ala Gly Val Asp Ala Ser Ala Val Glu Val
-25              -20              -15              -10

Thr Thr Ser Asp Gln Pro Glu Leu Tyr Ala Asp Ile Ile Gly Gly Leu
             -5              -1   1               5

Ala Tyr Thr Met Gly Gly Arg Cys Ser Val Gly Phe Ala Ala Thr Asn
            10               15              20

Ala Ala Gly Gln Pro Gly Phe Val Thr Ala Gly His Cys Gly Arg Val
        25               30              35

Gly Thr Gln Val Thr Ile Gly Asn Gly Arg Gly Val Phe Glu Gln Ser
40              45               50              55

Val Phe Pro Gly Asn Asp Ala Ala Phe Val Arg Gly Thr Ser Asn Phe
            60              65              70

Thr Leu Thr Asn Leu Val Ser Arg Tyr Asn Thr Gly Gly Tyr Ala Thr
            75              80              85

Val Ala Gly His Asn Gln Ala Pro Ile Gly Ser Ser Val Cys Arg Ser
            90              95              100

Gly Ser Thr Thr Gly Trp His Cys Gly Thr Ile Gln Ala Arg Gly Gln
105              110              115

Ser Val Ser Tyr Pro Glu Gly Thr Val Thr Asn Met Thr Arg Thr Thr
120              125              130              135

Val Cys Ala Glu Pro Gly Asp Ser Gly Gly Ser Tyr Ile Ser Gly Thr
            140              145              150

Gln Ala Gln Gly Val Thr Ser Gly Gly Ser Gly Asn Cys Arg Thr Gly
            155              160              165

Gly Thr Thr Phe Tyr Gln Glu Val Thr Pro Met Val Asn Ser Trp Gly
            170              175              180

Val Arg Leu Arg Thr
        185

<210> SEQ ID NO 44
<211> LENGTH: 1164
<212> TYPE: DNA
<213> ORGANISM: Artificial sequence
<220> FEATURE:
<223> OTHER INFORMATION: Synthetic protease encoding gene
<220> FEATURE:
<221> NAME/KEY: CDS
<222> LOCATION: (1)..(1164)
<223> OTHER INFORMATION: Full length protease
<220> FEATURE:
<221> NAME/KEY: sig_peptide
<222> LOCATION: (1)..(81)
<220> FEATURE:
<221> NAME/KEY: misc_feature
<222> LOCATION: (82)..(1164)
<223> OTHER INFORMATION: Propeptide
<220> FEATURE:
<221> NAME/KEY: mat_peptide
<222> LOCATION: (577)..(1164)
```

<400> SEQUENCE: 44

| | | | | | | | | | | | | | | | |
|---|---|---|---|---|---|---|---|---|---|---|---|---|---|---|---|
| atg | aaa | aaa | ccg | ctg | gga | aaa | att | gtc | gca | agc | aca | gca | ctt | ctt | 45 |
| Met | Lys | Lys | Pro | Leu | Gly | Lys | Ile | Val | Ala | Ser | Thr | Ala | Leu | Leu | |
| | -190 | | | | -185 | | | | -180 | | | | | | |

| att | tca | gtg | gca | ttt | agc | tca | tct | att | gca | tca | gca | gct | aca | gga | 90 |
|---|---|---|---|---|---|---|---|---|---|---|---|---|---|---|---|
| Ile | Ser | Val | Ala | Phe | Ser | Ser | Ser | Ile | Ala | Ser | Ala | Ala | Thr | Gly | |
| -175 | | | | | -170 | | | | -165 | | | | | | |

| gca | tta | ccg | cag | tct | ccg | aca | ccg | gaa | gca | gat | gca | gtc | tca | atg | 135 |
|---|---|---|---|---|---|---|---|---|---|---|---|---|---|---|---|
| Ala | Leu | Pro | Gln | Ser | Pro | Thr | Pro | Glu | Ala | Asp | Ala | Val | Ser | Met | |
| | -160 | | | | -155 | | | | -150 | | | | | | |

| caa | gaa | gca | ctg | caa | aga | gat | ctt | gat | ctt | aca | tca | gca | gaa | gca | 180 |
|---|---|---|---|---|---|---|---|---|---|---|---|---|---|---|---|
| Gln | Glu | Ala | Leu | Gln | Arg | Asp | Leu | Asp | Leu | Thr | Ser | Ala | Glu | Ala | |
| | -145 | | | | -140 | | | | -135 | | | | | | |

| gaa | gaa | ctt | ctt | gct | gca | caa | gat | aca | gca | ttt | gaa | gtg | gat | gaa | 225 |
|---|---|---|---|---|---|---|---|---|---|---|---|---|---|---|---|
| Glu | Glu | Leu | Leu | Ala | Ala | Gln | Asp | Thr | Ala | Phe | Glu | Val | Asp | Glu | |
| | -130 | | | | -125 | | | | -120 | | | | | | |

| gca | gcg | gca | gaa | gca | gca | gga | gat | gca | tat | ggc | ggc | tca | gtt | ttt | 270 |
|---|---|---|---|---|---|---|---|---|---|---|---|---|---|---|---|
| Ala | Ala | Ala | Glu | Ala | Ala | Gly | Asp | Ala | Tyr | Gly | Gly | Ser | Val | Phe | |
| | -115 | | | | -110 | | | | -105 | | | | | | |

| gat | aca | gaa | tca | ctt | gaa | ctt | aca | gtt | ctt | gtt | aca | gat | gca | gca | gca | 318 |
|---|---|---|---|---|---|---|---|---|---|---|---|---|---|---|---|---|
| Asp | Thr | Glu | Ser | Leu | Glu | Leu | Thr | Val | Leu | Val | Thr | Asp | Ala | Ala | Ala | |
| | -100 | | | | -95 | | | | -90 | | | | | | | |

| gtt | gaa | gca | gtt | gaa | gca | aca | gga | gca | gga | aca | gta | ctt | gtt | tca | tat | 366 |
|---|---|---|---|---|---|---|---|---|---|---|---|---|---|---|---|---|
| Val | Glu | Ala | Val | Glu | Ala | Thr | Gly | Ala | Gly | Thr | Val | Leu | Val | Ser | Tyr | |
| | -85 | | | | -80 | | | | -75 | | | | | | | |

| gga | att | gat | ggc | ctt | gat | gaa | att | gtt | caa | gaa | ctg | aat | gca | gct | gat | 414 |
|---|---|---|---|---|---|---|---|---|---|---|---|---|---|---|---|---|
| Gly | Ile | Asp | Gly | Leu | Asp | Glu | Ile | Val | Gln | Glu | Leu | Asn | Ala | Ala | Asp | |
| -70 | | | | -65 | | | | -60 | | | | -55 | | | | |

| gct | gtt | ccg | ggc | gtt | gtt | ggc | tgg | tat | ccg | gat | gtt | gct | gga | gat | aca | 462 |
|---|---|---|---|---|---|---|---|---|---|---|---|---|---|---|---|---|
| Ala | Val | Pro | Gly | Val | Val | Gly | Trp | Tyr | Pro | Asp | Val | Ala | Gly | Asp | Thr | |
| | | | -50 | | | | -45 | | | | -40 | | | | | |

| gtt | gtc | ctt | gaa | gtt | ctt | gaa | gga | tca | ggc | gca | gat | gtt | tca | ggc | ctg | 510 |
|---|---|---|---|---|---|---|---|---|---|---|---|---|---|---|---|---|
| Val | Val | Leu | Glu | Val | Leu | Glu | Gly | Ser | Gly | Ala | Asp | Val | Ser | Gly | Leu | |
| | | -35 | | | | -30 | | | | -25 | | | | | | |

| ctg | gca | gac | gca | gga | gtc | gat | gca | tca | gca | gtt | gaa | gtt | aca | aca | tca | 558 |
|---|---|---|---|---|---|---|---|---|---|---|---|---|---|---|---|---|
| Leu | Ala | Asp | Ala | Gly | Val | Asp | Ala | Ser | Ala | Val | Glu | Val | Thr | Thr | Ser | |
| | -20 | | | | -15 | | | | -10 | | | | | | | |

| gat | caa | ccg | gaa | ctt | tat | gca | gat | att | att | ggc | ggc | ctg | gca | tat | tat | 606 |
|---|---|---|---|---|---|---|---|---|---|---|---|---|---|---|---|---|
| Asp | Gln | Pro | Glu | Leu | Tyr | Ala | Asp | Ile | Ile | Gly | Gly | Leu | Ala | Tyr | Tyr | |
| -5 | | | | -1 | 1 | | | 5 | | | | 10 | | | | |

| atg | ggc | ggc | aga | tgc | agc | gtt | ggc | ttt | gca | gca | aca | aat | gca | tca | ggc | 654 |
|---|---|---|---|---|---|---|---|---|---|---|---|---|---|---|---|---|
| Met | Gly | Gly | Arg | Cys | Ser | Val | Gly | Phe | Ala | Ala | Thr | Asn | Ala | Ser | Gly | |
| | | | 15 | | | | 20 | | | | 25 | | | | | |

| caa | ccg | ggc | ttt | gtt | aca | gca | ggc | cat | tgc | ggc | aca | gtt | ggc | aca | cca | 702 |
|---|---|---|---|---|---|---|---|---|---|---|---|---|---|---|---|---|
| Gln | Pro | Gly | Phe | Val | Thr | Ala | Gly | His | Cys | Gly | Thr | Val | Gly | Thr | Pro | |
| | | 30 | | | | 35 | | | | 40 | | | | | | |

| gtt | tca | att | ggc | aat | ggc | aaa | ggc | gtt | ttt | gaa | cga | agc | att | ttt | ccg | 750 |
|---|---|---|---|---|---|---|---|---|---|---|---|---|---|---|---|---|
| Val | Ser | Ile | Gly | Asn | Gly | Lys | Gly | Val | Phe | Glu | Arg | Ser | Ile | Phe | Pro | |
| | | 45 | | | | 50 | | | | 55 | | | | | | |

| ggc | aat | gat | tca | gca | ttt | gtt | aga | ggc | aca | tca | aat | ttt | aca | ctt | aca | 798 |
|---|---|---|---|---|---|---|---|---|---|---|---|---|---|---|---|---|
| Gly | Asn | Asp | Ser | Ala | Phe | Val | Arg | Gly | Thr | Ser | Asn | Phe | Thr | Leu | Thr | |
| 60 | | | | 65 | | | | 70 | | | | | | | | |

| aat | ctg | gtt | tca | aga | tat | aat | tca | ggc | tat | gca | aca | gtt | gca | ggc | 846 |
|---|---|---|---|---|---|---|---|---|---|---|---|---|---|---|---|
| Asn | Leu | Val | Ser | Arg | Tyr | Asn | Ser | Gly | Tyr | Ala | Thr | Val | Ala | Gly | |
| 75 | | | | 80 | | | | 85 | | | | 90 | | | |

| cat | aat | caa | gca | ccg | att | ggc | tca | gca | gtt | tgc | aga | tca | ggc | tca | aca | 894 |
|---|---|---|---|---|---|---|---|---|---|---|---|---|---|---|---|---|
| His | Asn | Gln | Ala | Pro | Ile | Gly | Ser | Ala | Val | Cys | Arg | Ser | Gly | Ser | Thr | |
| | | | 95 | | | | 100 | | | | 105 | | | | | |

| aca | ggc | tgg | cat | tgc | ggc | aca | att | caa | gca | aga | aat | caa | aca | gtt | agg | 942 |
|---|---|---|---|---|---|---|---|---|---|---|---|---|---|---|---|---|

```
Thr Gly Trp His Cys Gly Thr Ile Gln Ala Arg Asn Gln Thr Val Arg
            110                 115                 120 tat ccg caa ggc aca gtt tat agt ctg aca aga aca aca gtt tgt gca      990
Tyr Pro Gln Gly Thr Val Tyr Ser Leu Thr Arg Thr Thr Val Cys Ala
            125                 130                 135 gaa ccg ggc gat tca ggc tca tat att agc ggc act caa gca caa         1038
Glu Pro Gly Asp Ser Gly Ser Tyr Ile Ser Gly Thr Gln Ala Gln
            140                 145                 150 ggc gtt aca tca ggc ggc tca ggc aat tgc agt gct ggc ggc aca aca     1086
Gly Val Thr Ser Gly Gly Ser Gly Asn Cys Ser Ala Gly Gly Thr Thr
155             160                 165                 170 tat tac caa gaa gtt aat ccg atg ctt agt tca tgg ggc ctt aca ctt     1134
Tyr Tyr Gln Glu Val Asn Pro Met Leu Ser Ser Trp Gly Leu Thr Leu
                175                 180                 185 aga aca caa tcg cat gtt caa tcc gct cca                             1164
Arg Thr Gln Ser His Val Gln Ser Ala Pro
            190                 195

<210> SEQ ID NO 45
<211> LENGTH: 388
<212> TYPE: PRT
<213> ORGANISM: Artificial sequence
<220> FEATURE:
<223> OTHER INFORMATION: Synthetic Construct

<400> SEQUENCE: 45

Met Lys Lys  Pro Leu Gly Lys Ile  Val Ala Ser Thr  Ala Leu Leu
    -190             -185              -180

Ile Ser Val  Ala Phe Ser Ser Ser  Ile Ala Ser Ala  Ala Thr Gly
    -175             -170              -165

Ala Leu Pro  Gln Ser Pro Thr Pro  Glu Ala Asp Ala  Val Ser Met
    -160             -155              -150

Gln Glu Ala  Leu Gln Arg Asp Leu  Asp Leu Thr Ser  Ala Glu Ala
    -145             -140              -135

Glu Glu Leu  Leu Ala Ala Gln Asp  Thr Ala Phe Glu  Val Asp Glu
    -130             -125              -120

Ala Ala Ala  Glu Ala Ala Gly Asp  Ala Tyr Gly Gly  Ser Val Phe
    -115             -110              -105

Asp Thr Glu  Ser Leu Glu Leu Thr  Val Leu Val Thr  Asp Ala Ala Ala
    -100              -95              -90

Val Glu Ala  Val Glu Ala Thr Gly  Ala Gly Thr Val  Leu Val Ser Tyr
    -85              -80               -75

Gly Ile Asp Gly Leu Asp Glu Ile Val Gln Glu Leu Asn Ala Ala Asp
-70              -65                  -60                  -55

Ala Val Pro  Gly Val Val Gly Trp  Tyr Pro Asp Val  Ala Gly Asp Thr
                 -50                  -45                  -40

Val Val Leu  Glu Val Leu Glu Gly  Ser Gly Ala Asp  Val Ser Gly Leu
                 -35                  -30                  -25

Leu Ala Asp  Ala Gly Val Asp Ala  Ser Ala Val Glu  Val Thr Thr Ser
            -20                  -15                  -10

Asp Gln Pro  Glu Leu Tyr Ala Asp  Ile Ile Gly Gly  Leu Ala Tyr Tyr
    -5                -1   1                 5                  10

Met Gly Gly  Arg Cys Ser Val Gly  Phe Ala Ala Thr  Asn Ala Ser Gly
                 15                   20                  25

Gln Pro Gly  Phe Val Thr Ala Gly  His Cys Gly Thr  Val Gly Thr Pro
                 30                   35                  40

Val Ser Ile  Gly Asn Gly Lys Gly  Val Phe Glu Arg  Ser Ile Phe Pro
                 45                   50                  55
```

```
Gly Asn Asp Ser Ala Phe Val Arg Gly Thr Ser Asn Phe Thr Leu Thr
         60                  65                  70

Asn Leu Val Ser Arg Tyr Asn Ser Gly Gly Tyr Ala Thr Val Ala Gly
 75                  80                  85                  90

His Asn Gln Ala Pro Ile Gly Ser Ala Val Cys Arg Ser Gly Ser Thr
                 95                 100                 105

Thr Gly Trp His Cys Gly Thr Ile Gln Ala Arg Asn Gln Thr Val Arg
             110                 115                 120

Tyr Pro Gln Gly Thr Val Tyr Ser Leu Thr Arg Thr Thr Val Cys Ala
             125                 130                 135

Glu Pro Gly Asp Ser Gly Gly Ser Tyr Ile Ser Gly Thr Gln Ala Gln
             140                 145                 150

Gly Val Thr Ser Gly Gly Ser Gly Asn Cys Ser Ala Gly Gly Thr Thr
155                 160                 165                 170

Tyr Tyr Gln Glu Val Asn Pro Met Leu Ser Ser Trp Gly Leu Thr Leu
                 175                 180                 185

Arg Thr Gln Ser His Val Gln Ser Ala Pro
             190                 195
```

<210> SEQ ID NO 46
<211> LENGTH: 165
<212> TYPE: PRT
<213> ORGANISM: Artificial sequence
<220> FEATURE:
<223> OTHER INFORMATION: Shuffled propeptide O-2.19
<220> FEATURE:
<221> NAME/KEY: PROPEP
<222> LOCATION: (1)..(165)

<400> SEQUENCE: 46

```
Ala Thr Gly Ala Leu Pro Gln Ser Pro Thr Pro Glu Ala Asp Ala Val
 1               5                  10                  15

Ser Met Gln Glu Ala Leu Gln Arg Asp Leu Asp Leu Thr Ser Ala Glu
             20                  25                  30

Ala Glu Glu Leu Leu Ala Ala Gln Asp Thr Ala Phe Glu Val Asp Glu
         35                  40                  45

Ala Ala Ala Ala Ala Gly Asp Ala Tyr Gly Gly Ser Val Phe Asp
 50                  55                  60

Thr Glu Ser Leu Thr Leu Thr Val Leu Val Thr Asp Ala Ser Ala Val
 65                  70                  75                  80

Glu Ala Val Glu Ala Gly Ala Glu Ala Lys Val Val Ser His Gly
                 85                  90                  95

Met Glu Gly Leu Glu Glu Ile Val Ala Asp Leu Asn Ala Ala Asp Ala
             100                 105                 110

Gln Pro Gly Val Val Gly Trp Tyr Pro Asp Ile His Ser Asp Thr Val
             115                 120                 125

Val Leu Glu Val Leu Glu Gly Ser Gly Ala Asp Val Asp Ser Leu Leu
             130                 135                 140

Ala Asp Ala Gly Val Asp Ala Ser Ala Val Glu Val Thr Thr Ser Asp
145                 150                 155                 160

Gln Pro Glu Leu Tyr
                165
```

<210> SEQ ID NO 47
<211> LENGTH: 166
<212> TYPE: PRT
<213> ORGANISM: Artificial sequence
<220> FEATURE:

```
<223> OTHER INFORMATION: Shuffled propeptide G-2.73
<220> FEATURE:
<221> NAME/KEY: PROPEP
<222> LOCATION: (1)..(166)

<400> SEQUENCE: 47

Ala Thr Gly Ala Leu Pro Gln Ser Pro Thr Pro Glu Ala Asp Ala Val
1               5                   10                  15

Ser Met Gln Glu Ala Leu Gln Arg Asp Leu Asp Leu Ser Ser Ala Glu
            20                  25                  30

Ala Glu Glu Leu Leu Ala Ala Gln Asp Thr Ala Phe Glu Val Asp Glu
        35                  40                  45

Ala Ala Ala Gly Ala Ala Gly Asp Ala Tyr Gly Gly Ser Val Phe Asp
    50                  55                  60

Thr Glu Thr Leu Glu Leu Thr Val Leu Val Thr Asp Ala Ser Ala Val
65                  70                  75                  80

Glu Ala Val Glu Ala Ala Gly Ala Glu Ala Lys Val Val Ser His Gly
                85                  90                  95

Met Glu Gly Leu Glu Glu Ile Val Ala Asp Leu Asn Ala Ala Asp Ala
            100                 105                 110

Gln Pro Gly Val Val Gly Trp Tyr Pro Asp Ile His Ser Asp Thr Val
        115                 120                 125

Val Val Glu Val Leu Gly Ser Gly Ala Asp Val Asp Ser Leu Leu
    130                 135                 140

Ala Asp Ala Gly Val Asp Thr Ala Asp Val Lys Val Glu Ser Thr Thr
145                 150                 155                 160

Glu Gln Pro Glu Leu Tyr
                165

<210> SEQ ID NO 48
<211> LENGTH: 166
<212> TYPE: PRT
<213> ORGANISM: Artificial sequence
<220> FEATURE:
<223> OTHER INFORMATION: Shuffled propeptide G-1.43
<220> FEATURE:
<221> NAME/KEY: PROPEP
<222> LOCATION: (1)..(166)

<400> SEQUENCE: 48

Ala Thr Gly Ala Leu Pro Gln Ser Pro Thr Pro Glu Ala Asp Ala Val
1               5                   10                  15

Ser Met Gln Glu Ala Leu Gln Arg Asp Leu Gly Leu Ser Ser Ser Gln
            20                  25                  30

Ala Glu Glu Leu Leu Asp Ala Gln Ala Glu Ser Phe Glu Ile Asp Glu
        35                  40                  45

Ala Ala Ala Ala Ala Ala Gly Asp Ala Tyr Gly Gly Ser Ile Phe Asp
    50                  55                  60

Thr Asp Ser Leu Thr Leu Thr Val Leu Val Thr Asp Ala Ser Ala Val
65                  70                  75                  80

Glu Ala Val Glu Ala Ala Gly Ala Glu Ala Lys Val Val Ser His Gly
                85                  90                  95

Met Glu Gly Leu Glu Glu Ile Val Ala Asp Leu Asn Ala Ala Asp Ala
            100                 105                 110

Gln Pro Gly Val Val Gly Trp Tyr Pro Asp Ile His Ser Asp Thr Val
        115                 120                 125

Val Leu Glu Val Leu Gly Ser Gly Ala Asp Val Asp Ser Leu Leu
    130                 135                 140
```

```
Ala Asp Ala Gly Val Asp Thr Ala Asp Val Lys Val Glu Ser Thr Thr
145                 150                 155                 160

Glu Gln Pro Glu Leu Tyr
                165
```

<210> SEQ ID NO 49
<211> LENGTH: 166
<212> TYPE: PRT
<213> ORGANISM: Artificial sequence
<220> FEATURE:
<223> OTHER INFORMATION: Shuffled propeptide G-2.6

<400> SEQUENCE: 49

```
Ala Thr Gly Ala Leu Pro Gln Ser Pro Thr Pro Glu Ala Asp Ala Val
1               5                   10                  15

Ser Met Gln Glu Ala Leu Gln Arg Asp Leu Asp Leu Thr Ser Ala Glu
            20                  25                  30

Ala Glu Glu Leu Leu Ala Ala Gln Asp Thr Ala Phe Glu Val Asp Glu
        35                  40                  45

Ala Ala Ala Ala Ala Gly Asp Ala Tyr Gly Gly Ser Ile Phe Asp
    50                  55                  60

Thr Glu Thr Leu Glu Leu Thr Val Leu Val Thr Asp Ser Ser Ser Val
65                  70                  75                  80

Glu Ala Val Glu Ala Ala Gly Ala Glu Ala Lys Val Val Ser His Gly
                85                  90                  95

Met Glu Gly Leu Glu Glu Ile Val Ala Asp Leu Asn Ala Ala Asp Ala
            100                 105                 110

Gln Pro Gly Val Val Gly Trp Tyr Pro Asp Ile His Ser Asp Thr Val
        115                 120                 125

Val Leu Glu Val Leu Glu Gly Ser Gly Ala Asp Val Asp Ser Leu Leu
    130                 135                 140

Ala Gly Ala Gly Val Asp Thr Ala Asp Val Lys Val Glu Ser Thr Thr
145                 150                 155                 160

Glu Gln Pro Glu Leu Tyr
                165
```

<210> SEQ ID NO 50
<211> LENGTH: 165
<212> TYPE: PRT
<213> ORGANISM: Artificial sequence
<220> FEATURE:
<223> OTHER INFORMATION: Shuffled propeptide G-2.5
<220> FEATURE:
<221> NAME/KEY: PROPEP
<222> LOCATION: (1)..(165)

<400> SEQUENCE: 50

```
Ala Thr Gly Ala Leu Pro Gln Ser Pro Thr Pro Glu Ala Asp Ala Val
1               5                   10                  15

Ser Met Gln Glu Ala Leu Gln Arg Asp Leu Gly Leu Thr Pro Leu Glu
            20                  25                  30

Ala Glu Glu Leu Leu Ala Ala Gln Asp Thr Ala Phe Glu Val Asp Glu
        35                  40                  45

Ala Ala Ala Glu Ala Ala Gly Asp Ala Tyr Gly Gly Ser Val Phe Asp
    50                  55                  60

Thr Glu Thr Leu Glu Leu Thr Val Leu Val Thr Asp Ser Ala Val
65                  70                  75                  80

Glu Ala Val Glu Ala Ala Gly Ala Glu Ala Lys Val Val Ser His Gly
                85                  90                  95
```

```
Met Glu Gly Leu Glu Glu Ile Val Ala Asp Leu Asn Ala Ala Asp Ala
                100                 105                 110

Gln Pro Gly Val Val Gly Trp Tyr Pro Asp Ile His Ser Asp Thr Val
            115                 120                 125

Val Leu Glu Val Leu Gly Ser Gly Ala Asp Val Asp Ser Leu Leu
130                 135                 140

Ala Asp Ala Gly Val Asp Ala Ser Ala Val Glu Val Thr Pro Ala Ala
145                 150                 155                 160

Arg Pro Glu Leu Tyr
                165

<210> SEQ ID NO 51
<211> LENGTH: 166
<212> TYPE: PRT
<213> ORGANISM: Artificial sequence
<220> FEATURE:
<223> OTHER INFORMATION: Shuffled propeptide G-2.3
<220> FEATURE:
<221> NAME/KEY: PROPEP
<222> LOCATION: (1)..(166)

<400> SEQUENCE: 51

Ala Thr Gly Ala Leu Pro Gln Ser Pro Thr Pro Asp Gly Ala Glu Ala
1               5                   10                  15

Thr Thr Met Val Glu Ala Leu Gln Arg Asp Leu Gly Leu Thr Pro Ala
                20                  25                  30

Glu Ala Glu Glu Leu Leu Ala Ala Gln Asp Thr Ala Phe Glu Val Asp
            35                  40                  45

Glu Ala Ala Ala Ala Ala Gly Asp Ala Tyr Gly Gly Ser Ile Phe
        50                  55                  60

Asp Thr Asp Ser Leu Thr Leu Thr Val Leu Val Thr Ala Ala Ala
65                  70                  75                  80

Val Glu Ala Val Glu Ala Ala Gly Ala Glu Ala Lys Val Val Ser His
                85                  90                  95

Gly Met Glu Gly Leu Glu Glu Ile Val Ala Asp Leu Asn Ala Ala Asp
                100                 105                 110

Ala Val Pro Gly Val Val Gly Trp Tyr Pro Asp Val Ala Gly Asp Thr
            115                 120                 125

Val Val Leu Glu Val Leu Glu Gly Ser Gly Ala Asp Val Tyr Ser Leu
        130                 135                 140

Leu Ala Asp Ala Gly Val Asp Ala Ser Ala Val Glu Val Thr Pro Ala
145                 150                 155                 160

Ala Gln Pro Glu Leu Tyr
                165

<210> SEQ ID NO 52
<211> LENGTH: 166
<212> TYPE: PRT
<213> ORGANISM: Artificial sequence
<220> FEATURE:
<223> OTHER INFORMATION: Shuffled propeptide G-1.4
<220> FEATURE:
<221> NAME/KEY: PROPEP
<222> LOCATION: (1)..(166)

<400> SEQUENCE: 52

Ala Thr Gly Ala Leu Pro Gln Ser Pro Thr Pro Glu Ala Asp Ala Val
1               5                   10                  15

Ser Met Gln Glu Ala Leu Gln Arg Asp Leu Gly Leu Ser Ser Gln
                20                  25                  30
```

-continued

Ala Glu Glu Leu Leu Asp Ala Gln Ala Glu Ser Phe Glu Ile Asp Glu
          35                  40                  45

Ala Ala Ala Ala Ala Ala Asp Ser Tyr Gly Gly Ser Ile Phe Asp
 50                  55                  60

Thr Asp Ser Leu Thr Leu Thr Val Leu Val Thr Asp Ala Ser Ala Val
 65                  70                  75                  80

Glu Ala Val Glu Ala Ala Gly Ala Glu Ala Lys Val Val Ser His Gly
                 85                  90                  95

Met Glu Gly Leu Glu Glu Ile Val Ala Asp Leu Asn Ala Ala Asp Ala
             100                 105                 110

Gln Pro Gly Val Val Gly Trp Tyr Pro Asp Ile His Ser Asp Thr Val
         115                 120                 125

Val Leu Glu Val Leu Glu Gly Ser Gly Ala Asp Val Asp Ser Leu Leu
     130                 135                 140

Ala Asp Ala Gly Val Asp Thr Ala Asp Val Lys Val Glu Ser Thr Thr
145                 150                 155                 160

Glu Gln Pro Glu Leu Tyr
                165

<210> SEQ ID NO 53
<211> LENGTH: 166
<212> TYPE: PRT
<213> ORGANISM: Artificial sequence
<220> FEATURE:
<223> OTHER INFORMATION: Shuffled propeptide G-1.2
<220> FEATURE:
<221> NAME/KEY: PROPEP
<222> LOCATION: (1)..(166)

<400> SEQUENCE: 53

Ala Thr Gly Ala Leu Pro Gln Ser Pro Thr Pro Glu Ala Asp Ala Val
 1               5                  10                  15

Ser Met Gln Glu Ala Leu Gln Arg Asp Leu Asp Leu Thr Ser Ala Glu
                 20                  25                  30

Ala Glu Leu Leu Ala Ala Gln Asp Thr Ala Phe Glu Val Asp Glu
          35                  40                  45

Ala Ala Ala Ala Ala Ala Gly Asp Ala Tyr Gly Gly Ser Ile Phe Asp
 50                  55                  60

Thr Glu Thr Leu Glu Leu Thr Val Leu Val Thr Asp Ser Ser Ser Val
 65                  70                  75                  80

Glu Ala Val Glu Ala Ala Gly Ala Glu Ala Lys Val Val Ser His Gly
                 85                  90                  95

Met Glu Gly Leu Glu Glu Ile Val Ala Asp Leu Asn Ala Ala Asp Ala
             100                 105                 110

Gln Pro Gly Val Val Gly Trp Tyr Pro Asp Ile His Ser Asp Thr Val
         115                 120                 125

Val Leu Glu Val Leu Glu Gly Ser Gly Ala Asp Val Asp Ser Leu Leu
     130                 135                 140

Ala Gly Ala Gly Val Asp Thr Ala Asp Val Lys Val Glu Ser Thr Thr
145                 150                 155                 160

Glu Gln Pro Glu Leu Tyr
                165

```
<210> SEQ ID NO 54
<211> LENGTH: 9
<212> TYPE: PRT
<213> ORGANISM: Artificial
<220> FEATURE:
<223> OTHER INFORMATION: Synthetic construct

<400> SEQUENCE: 54

Gly Ala Val Leu Ile Met Pro Phe Trp
1               5

<210> SEQ ID NO 55
<211> LENGTH: 5
<212> TYPE: PRT
<213> ORGANISM: Artificial
<220> FEATURE:
<223> OTHER INFORMATION: Synthetic construct

<400> SEQUENCE: 55

Ser Thr Asn Gln Tyr
1               5

<210> SEQ ID NO 56
<211> LENGTH: 5
<212> TYPE: PRT
<213> ORGANISM: Artificial
<220> FEATURE:
<223> OTHER INFORMATION: Synthetic construct

<400> SEQUENCE: 56

Gln Ser Val Ala Pro
1               5

<210> SEQ ID NO 57
<211> LENGTH: 8
<212> TYPE: PRT
<213> ORGANISM: Artificial
<220> FEATURE:
<223> OTHER INFORMATION: Synthetic construct

<400> SEQUENCE: 57

Gln Ser His Val Gln Ser Ala Pro
1               5

<210> SEQ ID NO 58
<211> LENGTH: 4
<212> TYPE: PRT
<213> ORGANISM: Artificial
<220> FEATURE:
<223> OTHER INFORMATION: Synthetic construct

<400> SEQUENCE: 58

Gln Ser Ala Pro
1
```

PROTEASES AND METHODS FOR PRODUCING THEM

CROSS-REFERENCE TO RELATED APPLICATIONS

This application is a divisional of U.S. Application No. 10/560,224 filed on Dec. 12, 2005, (now abandoned) which is a 35 U.S.C. 371 national application of PCT/DK2004/000436 filed Jun. 21, 2004, which claims priority or the benefit under 35 U.S.C. 119 of Danish Application Nos. PA 2003 00916, PA 2003 01847 and PA 2004 00334 filed Jun. 19, 2003, Dec. 12, 2003 and Mar. 1, 2004, respectively, and U.S. Provisional Application Nos. 60/480,292, 60/531,067 and 60/549,348 filed Jun. 20, 2003, Dec. 18, 2003, and Mar. 2, 2004, respectively, the contents of which are fully incorporated herein by reference.

FIELD OF THE INVENTION

A number of microbially derived related proteases are notably difficult to produce in industrially relevant yields, they may be prone to various types of degradation and/or instabilities. The present invention provides methods for producing such proteases by expressing them as proteases comprising a heterologous pro-sequence. The invention further provides the resulting proteases comprising such heterologous prosequences. The present invention relates to isolated polypeptides having protease activity related to a *Nocardiopsis* sp. protease, and isolated nucleic acid sequences encoding such proteases. The invention furthermore relates to nucleic acid constructs, vectors, and host cells comprising these nucleic acid sequences as well as methods for producing and using the proteases, in particular within animal feed.

BACKGROUND OF THE INVENTION

Polypeptides having protease activity, or proteases, are sometimes also designated peptidases, proteinases, peptide hydrolases, or proteolytic enzymes. Proteases may be of the exo-type that hydrolyses peptides starting at either end thereof, or of the endo-type that act internally in polypeptide chains (endopeptidases). Endopeptidases show activity on N- and C-terminally blocked peptide substrates that are relevant for the specificity of the protease in question.

The term "protease" is defined herein as an enzyme that hydrolyses peptide bonds. It includes any enzyme belonging to the EC 3.4 enzyme group (including each of the thirteen subclasses thereof). The EC number refers to Enzyme Nomenclature 1992 from NC-IUBMB, Academic Press, San Diego, Calif., including supplements 1-5 published in Eur. J. Biochem. 1994, 223, 1-5; Eur. J. Biochem. 1995, 232, 1-6; Eur. J. Biochem. 1996, 237, 1-5; Eur. J. Biochem. 1997, 250, 1-6; and Eur. J. Biochem. 1999, 264, 610-650; respectively. The nomenclature is regularly supplemented and updated; see e.g. the website at www.chem.qmw.ac.uk/iubmb/enzyme/index.html).

U.S. Application Publication No. 2002/0182672 discloses, that if one or two of the last two amino acids at the C-terminus of a polypeptide is/are charged polar: D or E (negatively charged) or K, R, or H (positively charged), the tail would be considered polar, charged, and this makes the polypeptide resistant against proteolytic degradation by a subclass of proteases that recognize non-polar C-terminal tails of secreted proteins.

Another disclosure reported that proline residues at the C-terminus of nascent polypeptide chains induce degradation of the polypeptide (2002. Prolin residues at the C terminus of nascent chains induce SsrA tagging during translation termination. J. Biol. Chem. 277:33825-33823).

SUMMARY OF THE INVENTION

It is a well known problem in the art of expressing polypeptides having proteolytic activity, that many of such polypeptides are inherently unstable, they may be subject to autoproteolysis, or they may be targeted for degradation by other proteases already during their production, resulting in suboptimal yields. Many other factors may contribute to their instability, not all of which are understood at present. It is of great interest to provide proteolytic polypeptides with an increased stability that may thus be produced in higher yields.

Secreted proteases of the S2A and/or S1E classification, often have a pro-region which is cleaved off from the protease to produce the mature part of the protease. The present inventors have found, that production of S2A and/or S1E proteases as fusion polypeptides comprising a heterologous pro-region results in much improved yields when compared with production of the unaltered wild-type proteases.

Accordingly, in a first aspect the invention relates to a secreted mature polypeptide which after maturation has protease activity, which polypeptide when expressed and before maturation comprises a heterologous pro-region, and which polypeptide:

(a) comprises an amino acid sequence which is at least 70% identical, or preferably 75%, 80%, 85%, 86%, 87%, 88%, 89%, 90%, 91%, 92%, 93%, 94%, 95%, 96%, 97%, 98%, or 99% identical to the amino acid sequence of the mature part of the polypeptide shown in SEQ ID NO: 28; SEQ ID NO: 33; SEQ ID NO: 37; SEQ ID NO: 41; SEQ ID NO: 43; or SEQ ID NO: 45;

(b) comprises an amino acid sequence which is at least 70% identical, or preferably 75%, 80%, 85%, 86%, 87%, 88%, 89%, 90%, 91%, 92%, 93%, 94%, 95%, 96%, 97%, 98%, or 99% identical to the amino acid sequence of the mature part of the polypeptide encoded by the polynucleotide in SEQ ID NO: 1; SEQ ID NO: 2; SEQ ID NO: 25; SEQ ID NO: 31; SEQ ID NO: 32; SEQ ID NO: 36; SEQ ID NO: 40; or SEQ ID NO: 44;

(c) comprises a mature part which is a variant of the mature part of the polypeptide having the amino acid sequence of SEQ ID NO: 28; SEQ ID NO: 33; SEQ ID NO: 37; SEQ ID NO: 41; SEQ ID NO: 43; or SEQ ID NO: 45, the segment comprising a substitution, deletion, extension, and/or insertion of one or more amino acids;

(d) is encoded by a nucleic acid sequence which hybridizes under very low, low, medium-low, medium, medium-high, high, or very high stringency conditions with:

(I) a polynucleotide encoding the mature part of a protease, said polynucleotide obtainable from genomic DNA from *Nocardiopsis dassonvillei* subsp. *dassonvillei* DSM 43235 by use of primers SEQ ID NOs: 26 and 27; from *Nocardiopsis alba* DSM 15647 by use of primers SEQ ID NOs: 34 and 35; from *Nocardiopsis prasina* DSM 15648 by use of primers SEQ ID NOs: 38 and 39; or from *Nocardiopsis prasina* DSM 15649 by use of primers SEQ ID NOs: 42 and 39;

(II) the polynucleotide of SEQ ID NO: 1; of SEQ ID NO: 2; of SEQ ID NO: 25; of SEQ ID NO: 31; of SEQ ID NO: 32; of SEQ ID NO: 36; of SEQ ID NO: 40; or of SEQ ID NO: 44;

(III) a subsequence of (I) or (II) of at least 500 nucleotides, preferably 400, 300, 200, or 100 nucleotides, or (IV) a complementary strand of (I), (II), or (III);

(e) is an allelic variant of (a), (b), (c), or (d); or (f) is a fragment of (a), (b), (c), (d), or (f).

In a second aspect, the invention relates to an isolated polynucleotide encoding a polypeptide as defined in the first aspect; or an isolated polynucleotide encoding a fusion polypeptide which after maturation has protease activity, which before maturation comprises a heterologous pro-region, and which polypeptide:

(a) comprises an amino acid sequence which is at least 70% identical, or preferably 75%, 80%, 85%, 86%, 87%, 88%, 89%, 90%, 91%, 92%, 93%, 94%, 95%, 96%, 97%, 98%, or 99% identical to the amino acid sequence of the mature part of the polypeptide shown in SEQ ID NO: 28; SEQ ID NO: 33; SEQ ID NO: 37; SEQ ID NO: 41; SEQ ID NO: 43; or SEQ ID NO: 45;

(b) comprises an amino acid sequence which is at least 70% identical, or preferably 75%, 80%, 85%, 86%, 87%, 88%, 89%, 90%, 91%, 92%, 93%, 94%, 95%, 96%, 97%, 98%, or 99% identical to the amino acid sequence of the mature part of the polypeptide encoded by the polynucleotide in SEQ ID NO: 1; SEQ ID NO: 2; SEQ ID NO: 25; SEQ ID NO: 31; SEQ ID NO: 32; SEQ ID NO: 36; SEQ ID NO: 40; or SEQ ID NO: 44;

(c) comprises a mature part which is a variant of the mature part of the polypeptide having the amino acid sequence of SEQ ID NO: 28; SEQ ID NO: 33; SEQ ID NO: 37; SEQ ID NO: 41; SEQ ID NO: 43; or SEQ ID NO: 45, the segment comprising a substitution, deletion, extension, and/or insertion of one or more amino acids;

(d) is encoded by a nucleic acid sequence which hybridizes under very low, low, medium-low, medium, medium-high, high, or very high stringency conditions with:

(I) a polynucleotide encoding the mature part of a protease, said polynucleotide obtainable from genomic DNA from *Nocardiopsis dassonvillei* subsp. *dassonvillei* DSM 43235 by use of primers SEQ ID NOs: 26 and 27; from *Nocardiopsis alba* DSM 15647 by use of primers SEQ ID NOs: 34 and 35; from *Nocardiopsis prasina* DSM 15648 by use of primers SEQ ID NOs: 38 and 39; or from *Nocardiopsis prasina* DSM 15649 by use of primers SEQ ID NOs: 42 and 39;

(II) the polynucleotide of SEQ ID NO: 1; of SEQ ID NO: 2; of SEQ ID NO: 25; of SEQ ID NO: 31; of SEQ ID NO: 32; of SEQ ID NO: 36; of SEQ ID NO: 40; or of SEQ ID NO: 44;

(III) a subsequence of (I) or (II) of at least 500 nucleotides, preferably 400, 300, 200, or 100 nucleotides, or (IV) a complementary strand of (I), (II), or (III);

(e) is an allelic variant of (a), (b), (c), or (d); or (f) is a fragment of (a), (b), (c), (d), or (f).

Still, in a third aspect, the invention relates to a recombinant expression vector or polynucleotide construct comprising a polynucleotide as defined in the previous aspect.

Yet a fourth aspect relates to a recombinant host cell comprising a polynucleotide as defined in the second aspect or an expression vector or polynucleotide construct as defined in the previous aspect.

In a fifth aspect, the invention also relates to a transgenic plant, or plant part, comprising a polynucleotide as defined in the second aspect, or an expression vector or polynucleotide construct as defined in the third aspect.

The sixth aspect of the invention relates to a transgenic, non-human animal, or products, or elements thereof, comprising a polynucleotide as defined in the second aspect, or an expression vector or polynucleotide construct as defined in the third aspect.

The seventh aspect of the invention relates to a method for producing a polypeptide as defined in the first aspect, the method comprising: (a) cultivating a recombinant host cell as defined in the fourth aspect, or a transgenic plant or animal as defined in the fifth or sixth aspects, to produce a supernatant comprising the polypeptide, and optionally (b) recovering the polypeptide.

Other aspects of then invention relate to: an animal feed additive comprising at least one polypeptide as defined in the first aspect; and (a) at least one fat-soluble vitamin, and/or (b) at least one water-soluble vitamin, and/or (c) at least one trace mineral;

an animal feed composition having a crude protein content of 50 to 800 g/kg and comprising at least one polypeptide as defined in the first aspect, or at least one feed additive of the previous aspect;

a composition comprising at least one polypeptide as defined in the first aspect, together with at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6);

a method for using at least one polypeptide as defined in the first aspect, for improving the nutritional value of an animal feed, for increasing digestible and/or soluble protein in animal diets, for increasing the degree of hydrolysis of proteins in animal diets, and/or for the treatment of vegetable proteins, the method comprising including the polypeptide(s) in animal feed, and/or in a composition for use in animal feed;

a method for using at least one polypeptide as defined in the first aspect, comprising including the polypeptide(s) in a detergent formulation.

DETAILED DESCRIPTION OF THE INVENTION

Proteases are classified on the basis of their catalytic mechanism into the following groups: Serine proteases (S), Cysteine proteases (C), Aspartic proteases (A), Metalloproteases (M), and Unknown, or as yet unclassified, proteases (U), see Handbook of Proteolytic Enzymes, A. J. Barrett, N. D. Rawlings, J. F. Woessner (eds), Academic Press (1998), in particular the general introduction part.

Serine proteases are ubiquitous, being found in viruses, bacteria and eukaryotes; they include exopeptidase, endopeptidase, oligopeptidase and omega-peptidase activity. Over 20 families (denoted S1-S27) of serine proteases have been identified, these being grouped into 6 clans denoted SA, SB, SC, SE, SF, and SG, on the basis of structural similarity and functional evidence (Barrett et al., 1998, Handbook of proteolytic enzymes). Structures are known for at least four of the clans (SA, SB, SC and SE), these appear to be totally unrelated, suggesting at least four evolutionary origins of serine peptidases. Alpha-lytic endopeptidases belong to the chymotrypsin (SA) clan, within which they have been assigned to subfamily A of the S2 family (S2A).

Another classification system of proteolytic enzymes is based on sequence information, and is therefore used more often in the art of molecular biology; it is described in Rawlings, N.D. et al., 2002, MEROPS: The protease database. Nucleic Acids Res. 30:343-346. The MEROPS database is freely available electronically at the website having the address www.merops.ac.uk. According to the MEROPS system, the proteolytic enzymes classified as S2A in 'The Handbook of Proteolytic Enzymes', are in MEROPS classified as 'S1 E' proteases (Rawlings ND, Barrett AJ. (1993) Evolutionary families of peptidase, Biochem. J. 290:205-218).

In particular embodiments, the proteases of the invention and for use according to the invention are selected from the group consisting of:

(a) proteases belonging to the EC 3.4.-.- enzyme group;

(b) Serine proteases belonging to the S group of the above Handbook;

(c1) Serine proteases of peptidase family S2A;

(c2) Serine proteases of peptidase family S1E as described in Biochem. J. 290:205-218 (1993) and in MEROPS a protease database, release 6.20, Mar. 24, 2003, (www.merops.ac.uk). The database is described in Rawlings, N. D., O'Brien, E. A. & Barrett, A. J. (2002) MEROPS: the protease database. Nucleic Acids Res. 30, 343-346.

For determining whether a given protease is a serine protease, and a family S2A protease, reference is made to the above Handbook and the principles indicated therein. Such determination can be carried out for all types of proteases, be it naturally occurring or wild-type proteases; or genetically engineered or synthetic proteases.

Protease activity can be measured using any assay, in which a substrate is employed, that includes peptide bonds relevant for the specificity of the protease in question. Assay-pH and assay-temperature are likewise to be adapted to the protease in question. Examples of assay-pH-values are pH 2, 3, 4, 5, 6, 7, 8, 9, 10, 11, or 12. Examples of assay-temperatures are 30, 35, 37, 40, 45, 50, 55, 60, 65, 70, 80, 90, or 95° C.

Examples of protease substrates are casein, such as Azurine-Crosslinked Casein (AZCL-casein). Two protease assays are described in Example 2 herein, either of which can be used to determine protease activity. For the purposes of this invention, the so-called pNA Assay is a preferred assay.

There are no limitations on the origin of the protease of the invention and/or for use according to the invention. Thus, the term protease includes not only natural or wild-type proteases obtained from microorganisms of any genus, but also any mutants, variants, fragments etc. thereof exhibiting protease activity, as well as synthetic proteases, such as shuffled proteases, and consensus proteases. Such genetically engineered proteases can be prepared as is generally known in the art, e.g., by Site-directed Mutagenesis, by PCR (using a PCR fragment containing the desired mutation as one of the primers in the PCR reactions), or by Random Mutagenesis. The preparation of consensus proteins is described in, e.g., EP 897985. The term "obtained from" as used herein in connection with a given source shall mean that the polypeptide encoded by the nucleic acid sequence is produced by the source or by a cell in which the nucleic acid sequence from the source is present. In a preferred embodiment, the polypeptide is secreted extracellularly.

In a specific embodiment, the protease is a low-allergenic variant, designed to invoke a reduced immunological response when exposed to animals, including man. The term immunological response is to be understood as any reaction by the immune system of an animal exposed to the protease. One type of immunological response is an allergic response leading to increased levels of IgE in the exposed animal. Low-allergenic variants may be prepared using techniques known in the art. For example the protease may be conjugated with polymer moieties shielding portions or epitopes of the protease involved in an immunological response. Conjugation with polymers may involve in vitro chemical coupling of polymer to the protease, e.g., as described in WO 96/17929, WO 98/30682, WO 98/35026, and/or WO 99/00489. Conjugation may in addition or alternatively thereto involve in vivo coupling of polymers to the protease. Such conjugation may be achieved by genetic engineering of the nucleotide sequence encoding the protease, inserting consensus sequences encoding additional glycosylation sites in the protease and expressing the protease in a host capable of glycosylating the protease, see, e.g., WO 00/26354. Another way of providing low-allergenic variants is genetic engineering of the nucleotide sequence encoding the protease so as to cause the protease to self-oligomerize, effecting that protease monomers may shield the epitopes of other protease monomers and thereby lowering the antigenicity of the oligomers. Such products and their preparation is described, e.g., in WO 96/16177. Epitopes involved in an immunological response may be identified by various methods such as the phage display method described in WO 00/26230 and WO 01/83559, or the random approach described in EP 561907. Once an epitope has been identified, its amino acid sequence may be altered to produce altered immunological properties of the protease by known gene manipulation techniques such as site directed mutagenesis (see, e.g., WO 00/26230, WO 00/26354 and/or WO 00/22103) and/or conjugation of a polymer may be done in sufficient proximity to the epitope for the polymer to shield the epitope.

The first aspect of the invention relates to a secreted mature polypeptide which after maturation has protease activity, which polypeptide when expressed and before maturation comprises a heterologous pro-region, and which polypeptide:

(a) comprises an amino acid sequence which is at least 70% identical, or preferably 75%, 80%, 85%, 86%, 87%, 88%, 89%, 90%, 91%, 92%, 93%, 94%, 95%, 96%, 97%, 98%, or 99% identical to the amino acid sequence of the mature part of the polypeptide shown in SEQ ID NO: 28; SEQ ID NO: 33; SEQ ID NO: 37; SEQ ID NO: 41; SEQ ID NO: 43; or SEQ ID NO: 45;

(b) comprises an amino acid sequence which is at least 70% identical, or preferably 75%, 80%, 85%, 86%, 87%, 88%, 89%, 90%, 91%, 92%, 93%, 94%, 95%, 96%, 97%, 98%, or 99% identical to the amino acid sequence of the mature part of the polypeptide encoded by the polynucleotide in SEQ ID NO: 1; SEQ ID NO: 2; SEQ ID NO: 25; SEQ ID NO: 31; SEQ ID NO: 32; SEQ ID NO: 36; SEQ ID NO: 40; or SEQ ID NO: 44;

(c) comprises a mature part which is a variant of the mature part of the polypeptide having the amino acid sequence of SEQ ID NO: 28; SEQ ID NO: 33; SEQ ID NO: 37; SEQ ID NO: 41; SEQ ID NO: 43; or SEQ ID NO: 45, the segment comprising a substitution, deletion, extension, and/or insertion of one or more amino acids;

(d) is encoded by a nucleic acid sequence which hybridizes under very low, low, medium-low, medium, medium-high, high, or very high stringency conditions with:

(I) a polynucleotide encoding the mature part of a protease, said polynucleotide obtainable from genomic DNA from *Nocardiopsis dassonvillei* subsp. *dassonvillei* DSM 43235 by use of primers SEQ ID NOs: 26 and 27; from *Nocardiopsis alba* DSM 15647 by use of primers SEQ ID NOs: 34 and 35; from *Nocardiopsis prasina* DSM 15648 by use of primers SEQ ID NOs: 38 and 39; or from *Nocardiopsis prasina* DSM 15649 by use of primers SEQ ID NOs: 42 and 39;

(II) the polynucleotide of SEQ ID NO: 1; of SEQ ID NO: 2; of SEQ ID NO: 25; of SEQ ID NO: 31; of SEQ ID NO: 32; of SEQ ID NO: 36; of SEQ ID NO: 40; or of SEQ ID NO: 44;

(III) a subsequence of (I) or (II) of at least 500 nucleotides, preferably 400, 300, 200, or 100 nucleotides, or (IV) a complementary strand of (I), (II), or (III);
(e) is an allelic variant of (a), (b), (c), or (d); or
(f) is a fragment of (a), (b), (c), (d), or (f).

For the purposes of the present invention, the degree of identity between two amino acid sequences, as well as the degree of identity between two nucleotide sequences, is determined by the program "align" which is a Needleman-Wunsch alignment (i.e., a global alignment). The program is used for alignment of polypeptide, as well as nucleotide sequences. The default scoring matrix BLOSUM50 is used for polypeptide alignments, and the default identity matrix is used for nucleotide alignments. The penalty for the first residue of a gap is −12 for polypeptides and −16 for nucleotides. The penalties for further residues of a gap are −2 for polypeptides, and −4 for nucleotide.

"Align" is part of the FASTA package version v20u6 (see W. R. Pearson and D. J. Lipman, 1988, "Improved Tools for Biological Sequence Analysis", PNAS 85:2444-2448, and W. R. Pearson, 1990, "Rapid and Sensitive Sequence Comparison with FASTP and FASTA," Methods in Enzymology 183: 63-98). FASTA protein alignments use the Smith-Waterman algorithm with no limitation on gap size (see "Smith-Waterman algorithm", T. F. Smith and M. S. Waterman, 1981, J. Mol. Biol. 147:195-197).

The degree of identity between two amino acid sequences may also be determined by the Clustal method (Higgins, 1989, CABIOS 5: 151-153) using the LASERGENE™ MEGALIGN™ software (DNASTAR, Inc., Madison, Wis.) with an identity table and the following multiple alignment parameters: Gap penalty of 10, and gap length penalty of 10. Pairwise alignment parameters are Ktuple=1, gap penalty=3, windows=5, and diagonals=5. The degree of identity between two nucleotide sequences may be determined using the same algorithm and software package as described above with the following settings: Gap penalty of 10, and gap length penalty of 10. Pairwise alignment parameters are Ktuple=3, gap penalty=3 and windows=20.

A fragment of one of the encoding polynucleotide sequences of the invention is a polynucleotide which encodes a polypeptide having one or more amino acids deleted from the amino and/or carboxyl terminus compared to the full-length amino acid sequence. In one embodiment a fragment encodes at least 75 amino acid residues, or at least 100 amino acid residues, or at least 125 amino acid residues, or at least 150 amino acid residues, or at least 160 amino acid residues, or at least 165 amino acid residues, or at least 170 amino acid residues, or at least 175 amino acid residues.

An allelic variant denotes any of two or more alternative forms of a gene occupying the same chromosomal locus. Allelic variation arises naturally through mutation, and may result in polymorphism within populations. Gene mutations can be silent (no change in the encoded polypeptide) or may encode polypeptides having altered amino acid sequences. An allelic variant of a polypeptide is a polypeptide encoded by an allelic variant of a gene.

The present invention also relates to isolated polypeptides having protease activity and which are encoded by nucleic acid sequences which hybridize under very low, or low, or low-medium, medium, medium-high, high, or very high stringency conditions with a nucleic acid probe which hybridizes under the same conditions with (I) a polynucleotide encoding the mature part of a protease obtainable from genomic DNA from *Nocardiopsis dassonvillei* subsp. *dassonvillei* DSM 43235 by use of primers SEQ ID NOs: 26 and 27; from *Nocardiopsis alba* DSM 15647 by use of primers SEQ ID NOs: 34 and 35; from *Nocardiopsis prasina* DSM 15648 by use of primers SEQ ID NOs: 38 and 39; or from *Nocardiopsis prasina* DSM 15649 by use of primers SEQ ID NOs: 42 and 39; (II) the polynucleotide of SEQ ID NO: 1; of SEQ ID NO: 2; of SEQ ID NO: 25; of SEQ ID NO: 31; of SEQ ID NO: 32; of SEQ ID NO: 36; of SEQ ID NO: 40; or of SEQ ID NO: 44; (III) a subsequence of (I) or (II) of at least 500 nucleotides, preferably 400, 300, 200, or 100 nucleotides, or (IV) a complementary strand of (I), (II), or (III) (J. Sambrook, E. F. Fritsch, and T. Maniatis, 1989, *Molecular Cloning, A Laboratory Manual*, 2nd edition, Cold Spring Harbor, N.Y.). In one particular embodiment the nucleic acid probe is selected from amongst the nucleic acid sequences of (a), (b), or (c) above. A polynucleotide corresponding to the mature peptide encoding part of SEQ ID NO: 1, SEQ ID NO: 25, SEQ ID NO: 31, SEQ ID NO: 32, SEQ ID NO: 36, SEQ ID NO: 40, or of SEQ ID NO: 44, is a preferred probe.

The nucleic acid sequences of SEQ ID NO: 1, SEQ ID NO: 25, SEQ ID NO: 31, SEQ ID NO: 32, SEQ ID NO: 36, SEQ ID NO: 40, or SEQ ID NO: 44, or a subsequence thereof, as well as the amino acid sequences of SEQ ID NO: 28; SEQ ID NO: 30; SEQ ID NO: 33; SEQ ID NO: 37, SEQ ID NO: 41, SEQ ID NO: 43, or SEQ ID NO: 45, or a fragment thereof, and even a genomic polynucleotide encoding a protease obtainable from genomic DNA from *Nocardiopsis dassonvillei* subsp. *dassonvillei* DSM 43235 by use of primers SEQ ID NOs: 26 and 27; from *Nocardiopsis alba* DSM 15647 by use of primers SEQ ID NOs: 34 and 35; from *Nocardiopsis prasina* DSM 15648 by use of primers SEQ ID NOs: 38 and 39; or from *Nocardiopsis prasina* DSM 15649 by use of primers SEQ ID NOs: 42 and 39, or a subsequence thereof, may be used to design a nucleic acid probe to identify and clone DNA encoding polypeptides having protease activity from strains of different genera or species according to methods well known in the art. In particular, such probes can be used for hybridization with the genomic or cDNA of the genus or species of interest, following standard Southern blotting procedures, in order to identify and isolate the corresponding gene therein. Such probes can be considerably shorter than the entire sequence, but should be at least 15, preferably at least 25, and more preferably at least 35 nucleotides in length. Longer probes can also be used. Both DNA and RNA probes can be used. The probes are typically labeled for detecting the corresponding gene (for example, with $^{32}$P, $^{3}$H, $^{35}$S, biotin, or avidin). Such probes are encompassed by the present invention.

Thus, a genomic DNA or cDNA library prepared from such other organisms may be screened for DNA that hybridizes with the probes described above and which encodes a polypeptide having protease activity. Genomic or other DNA from such other organisms may be separated by agarose or polyacrylamide gel electrophoresis, or other separation techniques. DNA from the libraries or the separated DNA may be transferred to and immobilized on nitrocellulose or other suitable carrier material. In order to identify a clone or DNA which is homologous with SEQ ID NO: 1 or a subsequence thereof, the carrier material is used in a Southern blot. For purposes of the present invention, hybridization indicates that the nucleic acid sequence hybridizes to a labeled nucleic acid probe corresponding to the nucleic acid sequence shown in SEQ ID NO: 1, its complementary strand, or a subsequence thereof, under very low to very high stringency conditions. Molecules to which the nucleic acid probe hybridizes under these conditions are detected using X-ray film.

For long probes of at least 100 nucleotides in length, very low to very high stringency conditions are defined as prehybridization and hybridization at 42° C. in 5×SSPE, 0.3% SDS, 200 μg/ml sheared and denatured salmon sperm DNA, and either 25% formamide for very low and low stringencies, 35% formamide for medium and medium-high stringencies, or 50% formamide for high and very high stringencies, following standard Southern blotting procedures.

For long probes of at least 100 nucleotides in length, the carrier material is finally washed three times each for 15 minutes using 0.2×SSC, 0.2% SDS, 20% formamide preferably at least at 45° C. (very low stringency), more preferably at least at 50° C. (low stringency), more preferably at least at 55° C. (medium stringency), more preferably at least at 60° C. (medium-high stringency), even more preferably at least at 65° C. (high stringency), and most preferably at least at 70° C. (very high stringency).

For short probes about 15 nucleotides to about 70 nucleotides in length, stringency conditions are defined as prehybrdization, hybridization, and washing post-hybridization at 5° C. to 10° C. below the calculated $T_m$ using the calculation according to Bolton and McCarthy (1962, *Proceedings of the National Academy of Sciences USA* 48:1390) in 0.9 M NaCl, 0.09 M Tris-HCl pH 7.6, 6 mM EDTA, 0.5% NP-40, 1×Denhardt's solution, 1 mM sodium pyrophosphate, 1 mM sodium monobasic phosphate, 0.1 mM ATP, and 0.2 mg of yeast RNA per ml following standard Southern blotting procedures.

For short probes about 15 nucleotides to about 70 nucleotides in length, the carrier material is washed once in 6×SSC plus 0.1% SDS for 15 minutes and twice each for 15 minutes using 6×SSC at 5° C. to 10° C. below the calculated $T_m$.

The present invention also relates to variants of the polypeptide of the invention, comprising a substitution, deletion, and/or insertion of one or more amino acids.

In a particular embodiment, amino acid changes are of a minor nature, that is conservative amino acid substitutions that do not significantly affect the folding and/or activity of the protein; small deletions, typically of one to about 30 amino acids; small amino- or carboxyl-terminal extensions, such as an amino-terminal methionine residue; a small peptide of up to about 2025 residues; or a small extension that facilitates purification by changing net charge or another function, such as a poly-histidine tract, an antigenic epitope or a binding domain.

Examples of conservative substitutions are within the group of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine). Amino acid substitutions which do not generally alter the specific activity are known in the art and are described, for example, by H. Neurath and R. L. Hill, 1979, In, *The Proteins*, Academic Press, New York. The most commonly occurring exchanges are Ala/Ser, Val/Ile, Asp/Glu, Thr/Ser, Ala/Gly, Ala/Thr, Ser/Asn, Ala/Val, Ser/Gly, Tyr/Phe, Ala/Pro, Lys/Arg, Asp/Asn, Leu/Ile, Leu/Val, Ala/Glu, and Asp/Gly as well as these in reverse.

In a particular embodiment, the polypeptides of the invention and for use according to the invention are acid-stable. For the present purposes, the term acid-stable means that the residual activity after 2 hours of incubation at pH 3.0 and 37° C., is at least 50%, as compared to the residual activity of a corresponding sample incubated for 2 hours at pH 9.0 and 5° C. In a particular embodiment, the residual activity is at least 60%, 70%, 80% or at least 90%.

In particular embodiments, the polypeptide of the invention is i) a bacterial protease; ii) a protease of the phylum Actinobacteia; iii) of the class Actinobacteda; iv) of the order Actinomycetales v) of the family Nocardiopsaceae; vi) of the genus *Nocardiopsis*; and/or a protease derived from vii) *Nocardiopsis* species such as *Nocardiopsis alba*, *Nocardiopsis antarctica*, *Nocardiopsis prasina, composta, exhalans, halophila, halotolerans, kunsanensis, listeri, lucentensis, metallicus, synnemataformans, trehalosi, tropica, umidischolae, xinjiangensis*, or *Nocardiopsis dassonvillei*, for example *Nocardiopsis dassonvillei* DSM 43235.

The above taxonomy is according to the chapter: The road map to the Manual by G. M. Garrity & J. G. Holt in Bergey's Manual of Systematic Bacteriology, 2001, second edition, volume 1, David R. Bone, Richard W. Castenholz.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSM), Centraalbureau Voor Schimmelcultures (CBS), and Agricultural Research Service Patent Culture Collection, Northern Regional Research Center (NRRL). For example, *Nocardiopsis dassonvillei* subsp. *dassonvillei* DSM 43235 is publicly available from DSMZ (Deutsche Sammiung von Mikroorganismen und Zellkulturen GmbH, Braunschweig, Germany). The strain was also deposited at other depositary institutions as follows: ATCC 23219, IMRU 1250, NCTC 10489.

Furthermore, such polypeptides may be identified and obtained from other sources including microorganisms isolated from nature (e.g., soil, composts, water, etc.) using the above-mentioned probes. Techniques for isolating microorganisms from natural habitats are well known in the art. The nucleic acid sequence may then be derived by similarly screening a genomic or cDNA library of another microorganism. Once a nucleic acid sequence encoding a polypeptide has been detected with the probe(s), the sequence may be isolated or cloned by utilizing techniques which are known to those of ordinary skill in the art (see, e.g., Sambrook et al., 1989, supra).

As defined herein, an "isolated" polypeptide is a polypeptide which is essentially free of other polypeptides, e.g., at least about 20% pure, preferably at least about 40% pure, more preferably about 60% pure, even more preferably about 80% pure, most preferably about 90% pure, and even most preferably about 95% pure, as determined by SDS-PAGE.

Polypeptides encoded by nucleic acid sequences of the present invention also include fused polypeptides or cleavable fusion polypeptides in which another polypeptide is fused at the N-terminus or the C-terminus of the polypeptide or fragment thereof. A fused polypeptide is produced by fusing a nucleic acid sequence (or a portion thereof) encoding another polypeptide to a nucleic acid sequence (or a portion thereof) of the present invention. Techniques for producing fusion polypeptides are known in the art, e.g., PCR, or ligating the coding sequences encoding the polypeptides so that they are in frame and that expression of the fused polypeptide is under control of the same promoter(s) and terminator.

In the present context, non-polar amino acids are G, A, V, L, I, M, P, F or W (SEQ ID NO:54); and uncharged polar amino acids are S, T, N, Q, Y, (SEQ ID NO:55) and C. The terms "non-polar" and "uncharged polar" when used to describe amino acids in a polypeptide are generally recognized in the art as characterizing the side-chain of the amino acid. Hence, for instance, the free carboxylic acid of the c-terminal amino acid in a polypeptide is not considered when determining whether this amino acid is a non-polar or uncharged polar amino acid.

A preferred embodiment releates to a polypeptide of the first aspect which mature part is a wildtype polypeptide; an artificial variant of a wildtype polypeptide said variant having one or more amino-acid(s) added to the C-terminus as compared to the wildtype and preferably the one or more added amino acid(s) is (are) non-polar or uncharged and even more preferably the one or more added amino acid(s) is one or more of Q, S, V, A, or P(SEQ ID NO:56); a shuffled polypeptide; or a protein-engineered polypeptide.

Yet another preferred embodiment relates to a polypeptide of the first aspect, which comprises at least three non-polar or uncharged polar amino acids within the last four amino acids of the C-terminus of the polypeptide;

Another preferred embodiment relates to a polypeptide of the first aspect, wherein the one or more added amino acids are selected from the group consisting of: QSHVQSAP(SEQ ID NO:57), QSAP (SEQ ID NO:58) QP, TL, TT, QL, TP, LP, TI, IQ, QP, PI, LT, TQ, IT, QQ, and PQ.

The inventors determined, that the polypeptides of the present invention were produced in even greater yields when they were expressed as mature proteases fused to a heterologous pro-region, and/or fused to a heterologous secretion signal peptide, as shown in the examples below.

Accordingly, a preferred embodiment relates to the polypeptide according to the first aspect which when expressed and before maturation comprises a heterologous secretion signal-peptide which is cleaved from the polypeptide when the polypeptide is secreted, preferably the heterologous secretion signal peptide is derived from a heterologous protease, preferably the heterologous secretion signal peptide comprises an amino acid sequence having a sequence identity of at least 70%, or preferably 75%, 80%, 85%, 86%, 87%, 88%, 89%, 90%, 91%, 92%, 93%, 94%, 95%, 96%, 97%, 98%, or 99%, with the amino acid sequence encoded by polynucleotides 1-81 of SEQ ID NO: 2, or SEQ ID NO: 44.

Accordingly, a preferred embodiment relates to the polypeptide according to the first aspect which when expressed and before maturation comprises a heterologous pro-region from a protease; preferably the pro-region is derived from an S2A or S1E protease, more preferably the pro-region is encoded by a polynucleotide which hybridizes under very low, low, medium-low, medium, medium-high, high, or very high stringency conditions with a polynucleotide encoding the pro-region shown in position −166 to −1 of SEQ ID NO: 28, in position 1-166 of SEQ ID NO: 30, in position −167 to −1 of SEQ ID NO: 33, in position −165 to −1 of SEQ ID NO: 37, in position −165 to −1 of SEQ ID NO: 41, in position −165 to −1 of SEQ ID NO: 43, in position −165 to −1 of SEQ ID NO: 45, in position 1-165 of SEQ ID NO: 46, in position 1-166 of SEQ ID NO: 47, in position 1-166 of SEQ ID NO: 48, in position 1-166 of SEQ ID NO: 49, in position 1-166 of SEQ ID NO: 50, in position 1-165 of SEQ ID NO: 51, in position 1-166 of SEQ ID NO: 52, or in position 1-166 of SEQ ID NO: 53; and most preferably it is at least 70% identical, or preferably 75%, 80%, 85%, 86%, 87%, 88%, 89%, 90%, 91%, 92%, 93%, 94%, 95%, 96%, 97%, 98%, or 99%, identical to the pro-region shown in position −166 to −1 of SEQ ID NO: 28, in position 1-166 of SEQ ID NO: 30, in position −167 to −1 of SEQ ID NO: 33, in position −165 to −1 of SEQ ID NO: 37, in position −165 to −1 of SEQ ID NO: 41, in position −165 to −1 of SEQ ID NO: 43, in position −165 to −1 of SEQ ID NO: 45, in position 1-165 of SEQ ID NO: 46, in position 1-166 of SEQ ID NO: 47, in position 1-166 of SEQ ID NO: 48, in position 1-166 of SEQ ID NO: 49, in position 1-166 of SEQ ID NO: 50, in position 1-165 of SEQ ID NO: 51, in position 1-166 of SEQ ID NO: 52, or in position 1-166 of SEQ ID NO: 53.

Nucleic Acid Sequences

The present invention also relates to isolated nucleic acid sequences that encode a polypeptide of the present invention. Particular nucleic acid sequences of the invention are the polynucleotides of SEQ ID NO: 1, SEQ ID NO: 2, SEQ ID NO: 25, SEQ ID NO: 31, SEQ ID NO: 32, SEQ ID NO: 36, SEQ ID NO: 40, or SEQ ID NO: 44. Another particular nucleic acid sequence of the invention is the sequence, preferably the mature polypeptide encoding region thereof, which is obtainable from genomic DNA from *Nocardiopsis dassonvillei* subspecies *dassonvillei* DSM 43235. The present invention also encompasses nucleic acid sequences which encode a polypeptide having the amino acid sequence of amino acids shown in positions 1 to 188, or positions −165 to 188, of SEQ ID NO: 43, which nucleic acid sequences differ from the corresponding parts of SEQ ID NO: 1 by virtue of the degeneracy of the genetic code. The present invention also relates to subsequences of the above polynucleotides which encode polypeptide fragments that have protease activity.

A subsequence of a polynucleotide is a nucleic acid sequence from which one or more nucleotides from the 5' and/or 3' end has been deleted. Preferably, a subsequence contains at least 225 nucleotides, more preferably at least 300 nucleotides, even more preferably at least 375, 450, 500, 531, 600, 700, 800, 900 or 1000 nucleotides. The present invention also relates to nucleotide sequences which have a degree of identity to the polynucleotide of SEQ ID NO: 1, SEQ ID NO: 2, SEQ ID NO: 25, SEQ ID NO: 31, SEQ ID NO: 32, SEQ ID NO: 36, SEQ ID NO: 40, or SEQ ID NO: 44, of at least 85%, 86, 87, 88, 89, 90, 91, 92, 93, 94, 95, 96, 97, 98, or at least 99%.

The techniques used to isolate or clone a nucleic acid sequence encoding a polypeptide are known in the art and include isolation from genomic DNA, preparation from cDNA, or a combination thereof. The cloning of the nucleic acid sequences of the present invention from such genomic DNA can be effected, e.g., by using the well known polymerase chain reaction (PCR) or antibody screening of expression libraries to detect cloned DNA fragments with shared structural features. See, e.g., Innis et al., 1990, *PCR: A Guide to Methods and Application*, Academic Press, New York. Other nucleic acid amplification procedures such as ligase chain reaction (LCR), ligated activated transcription (LAT) and nucleic acid sequence-based amplification (NASBA) may be used. The nucleic acid sequence may be cloned from a strain of *Nocardiopsis* or another or related organism and thus, for example, may be an allelic or species variant of the polypeptide encoding region of the nucleic acid sequence.

The term "isolated nucleic acid sequence" as used herein refers to a nucleic acid sequence which is essentially free of other nucleic acid sequences, e.g., at least about 20% pure, preferably at least about 40% pure, more preferably at least about 60% pure, even more preferably at least about 80% pure, and most preferably at least about 90% pure as determined by agarose electrophoresis. For example, an isolated nucleic acid sequence can be obtained by standard cloning procedures used in genetic engineering to relocate the nucleic acid sequence from its natural location to a different site where it will be reproduced. The cloning procedures may involve excision and isolation of a desired nucleic acid fragment comprising the nucleic acid sequence encoding the polypeptide, insertion of the fragment into a vector molecule, and incorporation of the recombinant vector into a host cell where multiple copies or clones of the nucleic acid sequence will be replicated. The nucleic acid sequence may be of genomic, cDNA, RNA, semisynthetic, synthetic origin, or any combinations thereof.

Modification of a nucleic acid sequence encoding a polypeptide of the present invention may be necessary for the synthesis of polypeptides substantially similar to the polypeptide. The term "substantially similar" to the polypeptide refers to non-naturally occurring forms of the polypeptide. These polypeptides may differ in some engineered way from the polypeptide isolated from its native source, e.g., variants that differ in specific activity, thermostability, pH optimum, allergenicity, or the like. The variant sequence may be constructed on the basis of the nucleic acid sequence presented as the polypeptide encoding part of the polynucleotides of the invention, e.g., a subsequence thereof, and/or by introduction of nucleotide substitutions which do not give rise to another amino acid sequence of the polypeptide encoded by the nucleic acid sequence, but which correspond to the codon usage of the host organism intended for production of the protease, or by introduction of nucleotide substitutions which may give rise to a different amino acid sequence. For a general description of nucleotide substitution, see, e.g., Ford et al., 1991, *Protein Expression and Purification* 2: 95-107. Low-allergenic polypeptides can, e.g., be prepared as described above.

It will be apparent to those skilled in the art that such substitutions can be made outside the regions critical to the function of the molecule and still result in an active polypeptide. Amino acid residues essential to the activity of the polypeptide encoded by the isolated nucleic acid sequence of the invention, and therefore preferably not subject to substitution, may be identified according to procedures known in the art, such as site-directed mutagenesis or alanine-scanning mutagenesis (see, e.g., Cunningham and Wells, 1989, *Science* 244: 1081-1085). In the latter technique, mutations are introduced at every positively charged residue in the molecule, and the resultant mutant molecules are tested for protease activity to identify amino acid residues that are critical to the activity of the molecule. Sites of substrate-protease interaction can also be determined by analysis of the three-dimensional structure as determined by such techniques as nuclear magnetic resonance analysis, crystallography or photoaffinity labelling (see, e.g., de Vos et al., 1992, *Science* 255: 306312; Smith et al., 1992, *Journal of Molecular Biology* 224: 899-904; Wlodaver et al., 1992, *FEBS Letters* 309: 59-64).

The present invention also relates to isolated nucleic acid sequences encoding a polypeptide of the present invention, which hybridize under very low stringency conditions, preferably low stringency conditions, more preferably medium stringency conditions, more preferably medium-high stringency conditions, even more preferably high stringency conditions, and most preferably very high stringency conditions with a nucleic acid probe which hybridizes under the same conditions with the nucleic acid sequence of the invention or its complementary strand; or allelic variants and subsequences thereof (Sambrook et al., 1989, supra), as defined herein.

The present invention also relates to isolated nucleic acid sequences produced by (a) hybridizing a DNA under very low, low, medium, medium-high, high, or very high stringency conditions with (i) a polynucleotide of the invention, (ii) a subsequence of (i), or (iii) a complementary strand of (i), or (ii); and (b) isolating the nucleic acid sequence. The subsequence is preferably a sequence of at least 100 nucleotides such as a sequence that encodes a polypeptide fragment which has protease activity.

The introduction of a mutation into the nucleic acid sequence to exchange one nucleotide for another nucleotide may be accomplished by site-directed mutagenesis using any of the methods known in the art. Particularly useful is the procedure that utilizes a supercoiled, double stranded DNA vector with an insert of interest and two synthetic primers containing the desired mutation. The oligonucleotide primers, each complementary to opposite strands of the vector, extend during temperature cycling by means of Pfu DNA polymerase. On incorporation of the primers, a mutated plasmid containing staggered nicks is generated. Following temperature cycling, the product is treated with DpnI which is specific for methylated and hemimethylated DNA to digest the parental DNA template and to select for mutation-containing synthesized DNA. Other procedures known in the art may also be used. The invention also relates to an isolated polynucleotide encoding a polypeptide as defined in the first aspect.

Nucleic Acid Constructs

The present invention also relates to nucleic acid constructs comprising a nucleic acid sequence of the present invention operably linked to one or more control sequences that direct the expression of the coding sequence in a suitable host cell under conditions compatible with the control sequences. Expression will be understood to include any step involved in the production of the polypeptide including, but not limited to, transcription, post-transcriptional modification, translation, post-translational modification, and secretion.

"Nucleic acid construct" is defined herein as a nucleic acid molecule, either single- or double-stranded, which is isolated from a naturally occurring gene or which has been modified to contain segments of nucleic acid combined and juxtaposed in a manner that would not otherwise exist in nature. The term nucleic acid construct is synonymous with the term expression cassette when the nucleic acid construct contains all the control sequences required for expression of a coding sequence of the present invention. The term "coding sequence" is defined herein as a nucleic acid sequence that directly specifies the amino acid sequence of its protein product. The boundaries of the coding sequence are generally determined by a ribosome binding site (prokaryotes) or by the ATG start codon (eukaryotes) located just upstream of the open reading frame at the 5' end of the mRNA and a transcription terminator sequence located just downstream of the open reading frame at the 3' end of the mRNA. A coding sequence can include, but is not limited to, DNA, cDNA, and recombinant nucleic acid sequences.

An isolated nucleic acid sequence encoding a polypeptide of the present invention may be manipulated in a variety of ways to provide for expression of the polypeptide. Manipulation of the nucleic acid sequence prior to its insertion into a vector may be desirable or necessary depending on the expression vector. The techniques for modifying nucleic acid sequences utilizing recombinant DNA methods are well known in the art.

The term "control sequences" is defined herein to include all components that are necessary or advantageous for the expression of a polypeptide of the present invention. Each control sequence may be native or foreign to the nucleic acid sequence encoding the polypeptide. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the nucleic acid sequence encoding a polypeptide. The term "operably linked" is defined herein as a configuration in which a control sequence is appropriately placed at a position relative to the coding sequence of the DNA sequence such that the control sequence directs the expression of a polypeptide.

The control sequence may be an appropriate promoter sequence, a nucleic acid sequence that is recognized by a host cell for expression of the nucleic acid sequence. The promoter sequence contains transcriptional control sequences that mediate the expression of the polypeptide. The promoter may be any nucleic acid sequence which shows transcriptional activity in the host cell of choice including mutant, truncated, and hybrid promoters, and may be obtained from genes encoding extracellular or intracellular polypeptides either homologous or heterologous to the host cell.

Examples of suitable promoters for directing the transcription of the nucleic acid constructs of the present invention, especially in a bacterial host cell, are the promoters obtained from the *E. coli* lac operon, *Streptomyces coelicolor* agarase gene (dagA), *Bacillus subtilis* levansucrase gene (sacB), *Bacillus licheniformis* alpha-amylase gene (amyL), *Bacillus stearothermophilus* maltogenic amylase gene (amyM), *Bacillus amyloliquefaciens* alpha-amylase gene (amyQ), *Bacillus licheniformis* penicillinase gene (penP), *Bacillus subtilis* xylA and xylB genes, and prokaryotic beta-lactamase gene (Villa-Kamaroff et al., 1978, Proceedings of the National Academy of Sciences USA 75: 3727-3731), as well as the tac promoter (DeBoer et al., 1983, Proceedings of the National Academy of Sciences USA 80: 21-25). Further promoters are described in "Useful proteins from recombinant bacteria" in Scientific American, 1980, 242: 74-94; and in Sambrook et al., 1989, supra.

Examples of suitable promoters for directing the transcription of the nucleic acid constructs of the present invention in a filamentous fungal host cell are promoters obtained from the genes for *Aspergillus oryzae* TAKA amylase, *Rhizomucor miehei* aspartic proteinase, *Aspergillus niger* neutral alpha-amylase, *Aspergillus niger* acid stable alpha-amylase, *Aspergillus niger* or *Aspergillus awamori* glucoamylase (glaA), *Rhizomucor miehei* lipase, *Aspergillus oryzae* alkaline protease, *Aspergillus oryzae* triose phosphate isomerase, *Aspergillus nidulans* acetamidase, and *Fusarium oxysporum* trypsin-like protease (WO 96/00787), as well as the NA2-tpi promoter (a hybrid of the promoters from the genes for *Aspergillus niger* neutral alpha-amylase and *Aspergillus oryzae* triose phosphate isomerase), and mutant, truncated, and hybrid promoters thereof.

In a yeast host, useful promoters are obtained from the genes for *Saccharomyces cerevisiae* enolase (ENO-1), *Saccharomyces cerevisiae* galactokinase (GAL-1), *Saccharomyces cerevisiae* alcohol dehydrogenase/glyceraldehyde-3-phosphate dehydrogenase (ADH2/GAP), and *Saccharomyces cerevisiae* 3-phosphoglycerate kinase. Other useful promoters for yeast host cells are described by Romanos et al., 1992, Yeast 8: 423-488.

The control sequence may also be a suitable transcription terminator sequence, a sequence recognized by a host cell to terminate transcription. The terminator sequence is operably linked to the 3' terminus of the nucleic acid sequence encoding the polypeptide. Any terminator which is functional in the host cell of choice may be used in the present invention.

Preferred terminators for filamentous fungal host cells are obtained from the genes for *Aspergillus oryzae* TAKA amylase, *Aspergillus niger* glucoamylase, *Aspergillus nidulans* anthranilate synthase, *Aspergillus niger* alpha-glucosidase, and *Fusarium oxysporum* trypsin-like protease.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase. Other useful terminators for yeast host cells are described by Romanos et al., 1992, supra.

Preferred terminators for bacterial host cells, such as a *Bacillus* host cell, are the terminators from *Bacillus licheniformis* alpha-amylase gene (amyL), the *Bacillus stearothermophilus* maltogenic amylase gene (amyM), or the *Bacillus amyloliquefaciens* alpha-amylase gene (amyQ).

The control sequence may also be a suitable leader sequence, a nontranslated region of an mRNA which is important for translation by the host cell. The leader sequence is operably linked to the 5' terminus of the nucleic acid sequence encoding the polypeptide. Any leader sequence that is functional in the host cell of choice may be used in the present invention.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae* 3-phosphoglycerate kinase, *Saccharomyces cerevisiae* alpha-factor, and *Saccharomyces cerevisiae* alcohol dehydrogenase/glyceraldehyde-3-phosphate dehydrogenase (ADH2/GAP).

The control sequence may also be a polyadenylation sequence, a sequence operably linked to the 3' terminus of the nucleic acid sequence and which, when transcribed, is recognized by the host cell as a signal to add polyadenosine residues to transcribed mRNA. Any polyadenylation sequence which is functional in the host cell of choice may be used in the present invention.

Preferred polyadenylation sequences for filamentous fungal host cells are obtained from the genes for *Aspergillus oryzae* TAKA amylase, *Aspergillus niger* glucoamylase, *Aspergillus nidulans* anthranilate synthase, *Fusarium oxysporum* trypsin-like protease, and *Aspergillus niger* alpha-glucosidase.

Useful polyadenylation sequences for yeast host cells are described by Guo and Sherman, 1995, Molecular Cellular Biology 15: 5983-5990.

The control sequence may also be a signal peptide coding region that codes for an amino acid sequence linked to the amino terminus of a polypeptide and directs the encoded polypeptide into the cell's secretory pathway. The 5' end of the coding sequence of the nucleic acid sequence may inherently contain a signal peptide coding region naturally linked in translation reading frame with the segment of the coding region which encodes the secreted polypeptide. Alternatively, the 5' end of the coding sequence may contain a signal peptide coding region which is foreign to the coding sequence. The foreign signal peptide coding region may be required where the coding sequence does not naturally contain a signal peptide coding region. Alternatively, the foreign signal peptide coding region may simply replace the natural signal peptide coding region in order to enhance secretion of the polypeptide. However, any signal peptide coding region which directs the expressed polypeptide into the secretory pathway of a host cell of choice may be used in the present invention.

Effective signal peptide coding regions for bacterial host cells are the signal peptide coding regions obtained from the genes for *Bacillus* NCIB 11837 maltogenic amylase, *Bacillus stearothermophilus* alpha-amylase, *Bacillus licheniformis* subtilisin, *Bacillus licheniformis* alpha-amylase, *Bacillus stearothermophilus* neutral proteases (nprT, nprS, nprM), and

*Bacillus subtilis* prsA. Further signal peptides are described by Simonen and Palva, 1993, Microbiological Reviews 57: 109-137.

Effective signal peptide coding regions for filamentous fungal host cells are the signal peptide coding regions obtained from the genes for *Aspergillus oryzae* TAKA amylase, *Aspergillus niger* neutral amylase, *Aspergillus niger* glucoamylase, *Rhizomucor miehei* aspartic proteinase, *Humicola insolens* cellulase, and *Humicola lanuginosa* lipase.

Useful signal peptides for yeast host cells are obtained from the genes for *Saccharomyces cerevisiae* alpha-factor and *Saccharomyces cerevisiae* invertase. Other useful signal peptide coding regions are described by Romanos et al., 1992, supra.

The control sequence may also be a propeptide coding region that codes for an amino acid sequence positioned at the amino terminus of a polypeptide. The resultant polypeptide is known as a proenzyme or propolypeptide (or a zymogen in some cases). A propolypeptide is generally inactive and can be converted to a mature active polypeptide by catalytic or autocatalytic cleavage of the propeptide from the propolypeptide. The propeptide coding region may be obtained from the genes for *Bacillus subtilis* alkaline protease (aprE), *Bacillus subtilis* neutral protease (nprT), *Saccharomyces cerevisiae* alpha-factor, *Rhizomucor miehei* aspartic proteinase, and *Myceliophthora thermophila* laccase (WO 95/33836).

Where both signal peptide and propeptide regions are present at the amino terminus of a polypeptide, the propeptide region is positioned next to the amino terminus of a polypeptide and the signal peptide region is positioned next to the amino terminus of the propeptide region.

It may also be desirable to add regulatory sequences which allow the regulation of the expression of the polypeptide relative to the growth of the host cell. Examples of regulatory systems are those which cause the expression of the gene to be turned on or off in response to a chemical or physical stimulus, including the presence of a regulatory compound. Regulatory systems in prokaryotic systems include the lac, tac, and trp operator systems. In yeast, the ADH2 system or GAL1 system may be used. In filamentous fungi, the TAKA alpha-amylase promoter, *Aspergillus niger* glucoamylase promoter, and *Aspergillus oryzae* glucoamylase promoter may be used as regulatory sequences. Other examples of regulatory sequences are those which allow for gene amplification. In eukaryotic systems, these include the dihydrofolate reductase gene which is amplified in the presence of methotrexate, and the metallothionein genes which are amplified with heavy metals. In these cases, the nucleic acid sequence encoding the polypeptide would be operably linked with the regulatory sequence.

Expression Vectors

The present invention also relates to recombinant expression vectors comprising a nucleic acid sequence of the present invention, a promoter, and transcriptional and translational stop signals. The various nucleic acid and control sequences described above may be joined together to produce a recombinant expression vector which may include one or more convenient restriction sites to allow for insertion or substitution of the nucleic acid sequence encoding the polypeptide at such sites. Alternatively, the nucleic acid sequence of the present invention may be expressed by inserting the nucleic acid sequence or a nucleic acid construct comprising the sequence into an appropriate vector for expression. In creating the expression vector, the coding sequence is located in the vector so that the coding sequence is operably linked with the appropriate control sequences for expression.

The recombinant expression vector may be any vector (e.g., a plasmid or virus) which can be conveniently subjected to recombinant DNA procedures and can bring about the expression of the nucleic acid sequence. The choice of the vector will typically depend on the compatibility of the vector with the host cell into which the vector is to be introduced. The vectors may be linear or closed circular plasmids.

The vector may be an autonomously replicating vector, i.e., a vector which exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one which, when introduced into the host cell, is integrated into the genome and replicated together with the chromosome(s) into which it has been integrated. Furthermore, a single vector or plasmid or two or more vectors or plasmids which together contain the total DNA to be introduced into the genome of the host cell, or a transposon may be used.

The vectors of the present invention preferably contain one or more selectable markers which permit easy selection of transformed cells. A selectable marker is a gene the product of which provides for biocide or viral resistance, resistance to heavy metals, prototrophy to auxotrophs, and the like. Examples of bacterial selectable markers are the dal genes from *Bacillus subtilis* or *Bacillus licheniformis*. Suitable markers for yeast host cells are ADE2, HIS3, LEU2, LYS2, MET3, TRP1, and URA3. Selectable markers for use in a filamentous fungal host cell include, but are not limited to, amdS (acetamidase), argB (ornithine carbamoyltransferase), bar (phosphinothricin acetyltransferase), hygB (hygromycin phosphotransferase), niaD (nitrate reductase), pyrG (orotidine-5'-phosphate decarboxylase), sC (sulfate adenyltransferase), trpC (anthranilate synthase), as well as equivalents thereof. Preferred for use in an *Aspergillus* cell are the amdS and pyrG genes of *Aspergillus nidulans* or *Aspergillus oryzae* and the bar gene of *Streptomyces hygroscopicus*.

The vectors of the present invention preferably contain an element(s) that permits stable integration of the vector into the host cell's genome or autonomous replication of the vector in the cell independent of the genome.

For integration into the host cell genome, the vector may rely on the nucleic acid sequence encoding the polypeptide or any other element of the vector for stable integration of the vector into the genome by homologous or nonhomologous recombination. Alternatively, the vector may contain additional nucleic acid sequences for directing integration by homologous recombination into the genome of the host cell. The additional nucleic acid sequences enable the vector to be integrated into the host cell genome at a precise location(s) in the chromosome(s). To increase the likelihood of integration at a precise location, the integrational elements should preferably contain a sufficient number of nucleic acids, such as 100 to 1,500 base pairs, preferably 400 to 1,500 base pairs, and most preferably 800 to 1,500 base pairs, which are highly homologous with the corresponding target sequence to enhance the probability of homologous recombination. The integrational elements may be any sequence that is homologous with the target sequence in the genome of the host cell. Furthermore, the integrational elements may be non-encoding or encoding nucleic acid sequences. On the other hand, the vector may be integrated into the genome of the host cell by non-homologous recombination.

For autonomous replication, the vector may further comprise an origin of replication enabling the vector to replicate autonomously in the host cell in question. Examples of bacterial origins of replication are the origins of replication of plasmids pBR322, pUC19, pACYC177, and pACYC184 permitting replication in *E. coli*, and pUB110, pE194, pTA1060, and pAMβ1 permitting replication in *Bacillus*. Examples of origins of replication for use in a yeast host cell are the 2 micron origin of replication, ARS1, ARS4, the combination of ARS1 and CEN3, and the combination of ARS4 and CEN6. The origin of replication may be one having a mutation which makes it functioning temperature-sensitive in the host cell (see, e.g., Ehrlich, 1978, *Proceedings of the National Academy of Sciences USA* 75: 1433).

More than one copy of a nucleic acid sequence of the present invention may be inserted into the host cell to increase production of the gene product. An increase in the copy number of the nucleic acid sequence can be obtained by integrating at least one additional copy of the sequence into the host cell genome or by including an amplifiable selectable marker gene with the nucleic acid sequence where cells containing amplified copies of the selectable marker gene, and thereby additional copies of the nucleic acid sequence, can be selected for by cultivating the cells in the presence of the appropriate selectable agent.

The procedures used to ligate the elements described above to construct the recombinant expression vectors of the present invention are well known to one skilled in the art (see, e.g., Sambrook et al., 1989, supra).

The protease may also be coexpressed together with at least one other enzyme of interest for animal feed, such as phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6).

The enzymes may be co-expressed from different vectors, from one vector, or using a mixture of both techniques. When using different vectors, the vectors may have different selectable markers, and different origins of replication. When using only one vector, the genes can be expressed from one or more promoters. If cloned under the regulation of one promoter (di- or multi-cistronic), the order in which the genes are cloned may affect the expression levels of the proteins. The protease may also be expressed as a fusion protein, i.e., that the gene encoding the protease has been fused in frame to the gene encoding another protein. This protein may be another enzyme or a functional domain from another enzyme.

Accordingly, the invention also relates to a recombinant expression vector or polynucleotide construct comprising a polynucleotide of the invention.

Host Cells

The present invention also relates to recombinant host cells, comprising a nucleic acid sequence of the invention, which are advantageously used in the recombinant production of the polypeptides. A vector comprising a nucleic acid sequence of the present invention is introduced into a host cell so that the vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source. The host cell may be a unicellular microorganism, e.g., a prokaryote, or a non-unicellular microorganism, e.g., a eukaryote.

Useful unicellular cells are bacterial cells such as gram positive bacteria including, but not limited to, a *Bacillus* cell, or a *Streptomyces* cell, or cells of lactic acid bacteria; or gram negative bacteria such as *E. coli* and *Pseudomonas* sp. Lactic acid bacteria include, but are not limited to, species of the genera *Lactococcus, Lactobacillus, Leuconostoc, Streptococcus, Pediococcus,* and *Enterococcus*. Useful unicellular cells are bacterial cells such as gram positive bacteria including, but not limited to, a *Bacillus* cell, e.g., *Bacillus alkalophilus, Bacillus amyloliquefaciens, Bacillus brevis, Bacillus circulans, Bacillus clausii, Bacillus coagulans, Bacillus lautus, Bacillus lentus, Bacillus licheniformis, Bacillus megaterium, Bacillus stearothermophilus, Bacillus subtilis,* and *Bacillus thuringiensis*; or a *Streptomyces* cell, e.g., *Streptomyces lividans* or *Streptomyces murinus*, or gram negative bacteria such as *E. coli* and *Pseudomonas* sp. In a preferred embodiment, the bacterial host cell is a *Bacillus lentus, Bacillus licheniformis, Bacillus stearothermophilus* or *Bacillus subtilis* cell. In another preferred embodiment, the *Bacillus* cell is an alkalophilic *Bacillus*.

The introduction of a vector into a bacterial host cell may, for instance, be effected by protoplast transformation (see, e.g., Chang and Cohen, 1979, *Molecular General Genetics* 168: 111-115), using competent cells (see, e.g., Young and Spizizin, 1961, *Journal of Bacteriology* 81: 823-829, or Dubnau and Davidoff-Abelson, 1971, *Journal of Molecular Biology* 56: 209-221), electroporation (see, e.g., Shigekawa and Dower, 1988, *Biotechniques* 6: 742-751), or conjugation (see, e.g., Koehler and Thorne, 1987, *Journal of Bacteriology* 169: 5771-5278). The host cell may be a eukaryote, such as a non-human animal cell, an insect cell, a plant cell, or a fungal cell. In one particular embodiment, the host cell is a fungal cell. "Fungi" as used herein includes the phyla Ascomycota, Basidiomycota, Chytridiomycota, and Zygomycota (as defined by Hawksworth et al., In, *Ainsworth and Bisby's Dictionary of The Fungi,* 8th edition, 1995, CAB International, University Press, Cambridge, UK) as well as the Oomycota (as cited in Hawksworth et al., 1995, supra, page 171) and all mitosporic fungi (Hawksworth et al., 1995, supra).

In another particular embodiment, the fungal host cell is a yeast cell. "Yeast" as used herein includes ascosporogenous yeast (Endomycetales), basidiosporogenous yeast, and yeast belonging to the Fungi Imperfecti (Blastomycetes). Since the classification of yeast may change in the future, for the purposes of this invention, yeast shall be defined as described in *Biology and Activities of Yeast* (Skinner, F. A., Passmore, S. M., and Davenport, R. R., eds, *Soc. App. Bacteriol. Symposium Series* No. 9, 1980).

The yeast host cell may be a *Candida, Hansenula, Kluyveromyces, Pichia, Saccharomyces, Schizosaccharomyces,* or *Yarrowia* cell.

The fungal host cell may be a filamentous fungal cell. "Filamentous fungi" include all filamentous forms of the subdivision Eumycota and Oomycota (as defined by Hawksworth et al., 1995, supra). The filamentous fungi are characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

Examples of filamentous fungal host cells are cells of species of, but not limited to, *Acremonium, Aspergillus, Fusarium, Humicola, Mucor, Myceliophthora, Neurospora, Penicillium, Thielavia, Tolypocladium,* or *Trichoderma*.

Fungal cells may be transformed by a process involving protoplast formation, transformation of the protoplasts, and regeneration of the cell wall in a manner known per se. Suitable procedures for transformation of *Aspergillus* host cells are described in EP 238 023 and Yelton et al., 1984, *Proceedings of the National Academy of Sciences USA* 81: 1470-1474. Suitable methods for transforming *Fusarium* species are described by Malardier et al., 1989, *Gene* 78: 147-156 and WO 96/00787. Yeast may be transformed using the procedures described by Becker and Guarente, In Abelson, J. N. and Simon, M. I., editors, *Guide to Yeast Genetics and Molecular Biology, Methods in Enzymology*, Volume 194, pp 182-187, Academic Press, Inc., New York; Ito et al., 1983, *Journal of Bacteriology* 153: 163; and Hinnen et al., 1978, *Proceedings of the National Academy of Sciences USA* 75: 1920.

The invention relates to a recombinant host cell comprising a polynucleotide of the invention, or an expression vector or polynucleotide construct of the invention. In a preferred embodiment, the recombinant host cell is a *Bacillus* cell.

Plants

The present invention also relates to a transgenic plant, plant part, or plant cell which has been transformed with a nucleic acid sequence encoding a polypeptide having protease activity of the present invention so as to express and produce the polypeptide in recoverable quantities. The polypeptide may be recovered from the plant or plant part. Alternatively, the plant or plant part containing the recombinant polypeptide may be used as such for improving the quality of a food or feed, e.g., improving nutritional value, palatability, and rheological properties, or to destroy an antinutritive factor.

In a particular embodiment, the polypeptide is targeted to the endosperm storage vacuoles in seeds. This can be obtained by synthesizing it as a precursor with a suitable signal peptide, see Horvath et al. in PNAS, Feb. 15, 2000, vol. 97, no. 4, p. 1914-1919.

The transgenic plant can be dicotyledonous (a dicot) or monocotyledonous (a monocot) or engineered variants thereof. Examples of monocot plants are grasses, such as meadow grass (blue grass, Poa), forage grass such as festuca, lolium, temperate grass, such as Agrostis, and cereals, e.g., wheat, oats, rye, barley, rice, sorghum, and maize (corn). Examples of dicot plants are tobacco, legumes, such as lupins, potato, sugar beet, pea, bean and soybean, and cruciferous plants (family Brassicaceae), such as cauliflower, rape seed, and the closely related model organism *Arabidopsis thaliana*. Low-phytate plants as described, e.g., in U.S. Pat. Nos. 5,689,054 and 6,111,168 are examples of engineered plants.

Examples of plant parts are stem, callus, leaves, root, fruits, seeds, and tubers. Also specific plant tissues, such as chloroplast, apoplast, mitochondria, vacuole, peroxisomes, and cytoplasm are considered to be a plant part. Furthermore, any plant cell, whatever the tissue origin, is considered to be a plant part.

Also included within the scope of the present invention are the progeny of such plants, plant parts and plant cells.

The transgenic plant or plant cell expressing a polypeptide of the present invention may be constructed in accordance with methods known in the art. Briefly, the plant or plant cell is constructed by incorporating one or more expression constructs encoding a polypeptide of the present invention into the plant host genome and propagating the resulting modified plant or plant cell into a transgenic plant or plant cell.

Conveniently, the expression construct is a nucleic acid construct which comprises a nucleic acid sequence encoding a polypeptide of the present invention operably linked with appropriate regulatory sequences required for expression of the nucleic acid sequence in the plant or plant part of choice.

Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences are determined, for example, on the basis of when, where, and how the polypeptide is desired to be expressed. For instance, the expression of the gene encoding a polypeptide of the present invention may be constitutive or inducible, or may be developmental, stage or tissue specific, and the gene product may be targeted to a specific tissue or plant part such as seeds or leaves. Regulatory sequences are, for example, described by Tague et al., 1988, *Plant Physiology* 86: 506.

For constitutive expression, the 35S-CaMV promoter may be used (Franck et al., 1980, *Cell* 21: 285294). Organ-specific promoters may be, for example, a promoter from storage sink tissues such as seeds, potato tubers, and fruits (Edwards & Coruzzi, 1990, *Ann. Rev. Genet.* 24: 275303), or from metabolic sink tissues such as meristems (Ito et al., 1994, *Plant Mol. Biol.* 24: 863-878), a seed specific promoter such as the glutelin, prolamin, globulin, or albumin promoter from rice (Wu et al., 1998, *Plant and Cell Physiology* 39: 885-889), a *Vicia faba* promoter from the legumin B4 and the unknown seed protein gene from *Vicia faba* (Conrad et al., 1998, *Journal of Plant Physiology* 152: 708-711), a promoter from a seed oil body protein (Chen et al., 1998, Plant and Cell Physiology 39: 935-941), the storage protein napA promoter from *Brassica napus*, or any other seed specific promoter known in the art, e.g., as described in WO 91/14772. Furthermore, the promoter may be a leaf specific promoter such as the rbcs promoter from rice or tomato (Kyozuka et al., 1993, *Plant Physiology* 102: 991-1000, the chlorella virus adenine methyltransferase gene promoter (Mitra and Higgins, 1994, *Plant Molecular Biology* 26: 8593), or the aldP gene promoter from rice (Kagaya et al., 1995, *Molecular and General Genetics* 248: 668-674), or a wound inducible promoter such as the potato pin2 promoter (Xu et al., 1993, *Plant Molecular Biology* 22: 573-588).

A promoter enhancer element may also be used to achieve higher expression of the protease in the plant. For instance, the promoter enhancer element may be an intron which is placed between the promoter and the nucleotide sequence encoding a polypeptide of the present invention. For instance, Xu et al., 1993, supra disclose the use of the first intron of the rice actin 1 gene to enhance expression.

Still further, the codon usage may be optimized for the plant species in question to improve expression (see Horvath et al. referred to above).

The selectable marker gene and any other parts of the expression construct may be chosen from those available in the art.

The nucleic acid construct is incorporated into the plant genome according to conventional techniques known in the art, including *Agrobacterium*-mediated transformation, virus-mediated transformation, microinjection, particle bombardment, biolistic transformation, and electroporation (Gasser et al., 1990, *Science* 244:1293; Potrykus, 1990, *Bio/Technology* 8: 535; Shimamoto et al., 1989, *Nature* 338: 274).

Presently, *Agrobacterium tumefaciens*-mediated gene transfer is the method of choice for generating transgenic dicots (for a review, see Hooykas and Schilperoort, 1992, *Plant Molecular Biology* 19: 1538). However it can also be used for transforming monocots, although other transformation methods are generally preferred for these plants. Presently, the method of choice for generating transgenic monocots is particle bombardment (microscopic gold or tungsten particles coated with the transforming DNA) of embryonic calli or developing embryos (Christou, 1992, *Plant Journal* 2: 275281; Shimamoto, 1994, *Current Opinion Biotechnology* 5: 158-162; Vasil et al., 1992, *Bio/Technology* 10: 667-674). An alternative method for transformation of monocots is based on protoplast transformation as described by Omirulleh et al., 1993, *Plant Molecular Biology* 21: 415-428.

Following transformation, the transformants having incorporated therein the expression construct are selected and regenerated into whole plants according to methods well-known in the art.

The present invention also relates to methods for producing a polypeptide of the present invention comprising (a) cultivating a transgenic plant or a plant cell comprising a nucleic acid sequence encoding a polypeptide having protease activity of the present invention under conditions conducive for production of the polypeptide; and (b) recovering the polypeptide. The invention relates to a transgenic plant, or plant part, comprising a polynucleotide as defined in claim 8, or an expression vector or polynucleotide construct of the invention.

Animals

The present invention also relates to a transgenic, non-human animal and products or elements thereof, examples of which are body fluids such as milk and blood, organs, flesh, and animal cells. Techniques for expressing proteins, e.g., in mammalian cells, are known in the art, see, e.g., the handbook Protein Expression: A Practical Approach, Higgins and Hames (eds), Oxford University Press (1999), and the three other handbooks in this series relating to Gene Transcription, RNA processing, and Post-translational Processing. Generally speaking, to prepare a transgenic animal, selected cells of a selected animal are transformed with a nucleic acid sequence encoding a polypeptide having protease activity of the present invention so as to express and produce the polypeptide. The polypeptide may be recovered from the animal, e.g., from the milk of female animals, or the polypeptide may be expressed to the benefit of the animal itself, e.g., to assist the animal's digestion. Examples of animals are mentioned below in the section headed Animal Feed.

To produce a transgenic animal with a view to recovering the protease from the milk of the animal, a gene encoding the protease may be inserted into the fertilized eggs of an animal in question, e.g., by use of a transgene expression vector which comprises a suitable milk protein promoter, and the gene encoding the protease. The transgene expression vector is microinjected into fertilized eggs, and preferably permanently integrated into the chromosome. Once the egg begins to grow and divide, the potential embryo is implanted into a surrogate mother, and animals carrying the transgene are identified. The resulting animal can then be multiplied by conventional breeding. The polypeptide may be purified from the animal's milk, see, e.g., Meade, H. M. et al., 1999, Expression of recombinant proteins in the milk of transgenic animals, Gene expression systems: Using nature for the art of expression. J. M. Fernandez and J. P. Hoeffler (eds.), Academic Press.

In the alternative, in order to produce a transgenic non-human animal that carries in the genome of its somatic and/or germ cells a nucleic acid sequence including a heterologous transgene construct including a transgene encoding the protease, the transgene may be operably linked to a first regulatory sequence for salivary gland specific expression of the protease, as disclosed in WO 00/64247.

The invention relates to a transgenic, non-human animal, or products, or elements thereof, comprising a polynucleotide, or an expression vector or polynucleotide construct of the invention.

Methods of Production

The present invention also relates to methods for producing a polypeptide of the present invention comprising (a) cultivating a host cell or a transgenic plant or animal under conditions conducive for production of the polypeptide in a supernatant: and optionally (b) recovering the polypeptide.

In the production methods of the present invention, the cells are cultivated in a nutrient medium suitable for production of the polypeptide using methods known in the art. For example, the cell may be cultivated by shake flask cultivation, small-scale or large-scale fermentation (including continuous, batch, fed-batch, or solid state fermentations) in laboratory or industrial fermentors performed in a suitable medium and under conditions allowing the polypeptide to be expressed and/or isolated. The cultivation takes place in a suitable nutrient medium comprising carbon and nitrogen sources and inorganic salts, using procedures known in the art. Suitable media are available from commercial suppliers or may be prepared according to published compositions (e.g., in catalogues of the American Type Culture Collection).

If the polypeptide is secreted into the nutrient medium, the polypeptide can be recovered directly from the medium. If the polypeptide is not secreted, it can be recovered from cell lysates.

The polypeptides may be detected using methods known in the art that are specific for the polypeptides. These detection methods may include use of specific antibodies, formation of a product, or disappearance of a substrate. For example, a protease assay may be used to determine the activity of the polypeptide as described herein.

The resulting polypeptide may be recovered by methods known in the art. For example, the polypeptide may be recovered from the nutrient medium by conventional procedures including, but not limited to, centrifugation, filtration, extraction, spray-drying, evaporation, or precipitation.

The polypeptides of the present invention may be purified by a variety of procedures known in the art including, but not limited to, chromatography (e.g., ion exchange, affinity, hydrophobic, chromatofocusing, and size exclusion), electrophoretic procedures (e.g., preparative isoelectric focusing), differential solubility (e.g., ammonium sulfate precipitation), SDS-PAGE, or extraction (see, e.g., Protein Purification, J. C. Janson and Lars Ryden, editors, VCH Publishers, New York, 1989).

Compositions

In a still further aspect, the present invention relates to compositions comprising a polypeptide of the present invention. The polypeptide compositions may be prepared in accordance with methods known in the art and may be in the form of a liquid or a dry composition. For instance, the polypeptide composition may be in the form of a granulate or a microgranulate. The polypeptide to be included in the composition may be stabilized in accordance with methods known in the art. Examples are given below of preferred uses of the polypeptides or polypeptide compositions of the invention.

Animal Feed

The present invention is also directed to methods for using the polypeptides of the invention in animal feed, as well as to feed compositions and feed additives comprising the polypeptides of the invention. The term animal includes all animals, including human beings. Examples of animals are non-ruminants, and ruminants, such as cows, sheep and horses. In a particular embodiment, the animal is a non-ruminant animal. Non-ruminant animals include monogastric animals, e.g., pigs or swine (including, but not limited to, piglets, growing pigs, and sows); poultry such as turkeys, ducks and chicken (including but not limited to broiler chicks, layers); young calves; and fish (including but not limited to salmon, trout, tilapia, catfish and carps; and crustaceans (including but not limited to shrimps and prawns)

The term feed or feed composition means any compound, preparation, mixture, or composition suitable for, or intended for intake by an animal.

In the use according to the invention the protease can be fed to the animal before, after, or simultaneously with the diet. The latter is preferred.

In a particular embodiment, the protease, in the form in which it is added to the feed, or when being included in a feed additive, is well-defined. Well-defined means that the protease preparation is at least 50% pure as determined by Size-exclusion chromatography (see Example 12 of WO 01/58275). In other particular embodiments the protease preparation is at least 60, 70, 80, 85, 88, 90, 92, 94, or at least 95% pure as determined by this method. A well-defined protease preparation is advantageous. For instance, it is much easier to dose correctly to the feed a protease that is essentially free from interfering or contaminating other proteases. The term dose correctly refers in particular to the objective of obtaining consistent and constant results, and the capability of optimising dosage based upon the desired effect.

For the use in animal feed, however, the protease need not be that pure; it may, e.g., include other enzymes, in which case it could be termed a protease preparation. The protease preparation can be (a) added directly to the feed (or used directly in a treatment process of vegetable proteins), or (b) it can be used in the production of one or more intermediate compositions such as feed additives or premixes that is subsequently added to the feed (or used in a treatment process). The degree of purity described above refers to the purity of the original protease preparation, whether used according to (a) or (b) above.

Protease preparations with purities of this order of magnitude are in particular obtainable using recombinant methods of production, whereas they are not so easily obtained and also subject to a much higher batch-to-batch variation when the protease is produced by traditional fermentation methods. Such protease preparation may of course be mixed with other enzymes.

In a particular embodiment, the protease for use according to the invention is capable of solubilising vegetable proteins. A suitable assay for determining solubilised protein is disclosed in Example 11.

The term vegetable proteins as used herein refers to any compound, composition, preparation or mixture that includes at least one protein derived from or originating from a vegetable, including modified proteins and protein-derivatives. In particular embodiments, the protein content of the vegetable proteins is at least 10, 20, 30, 40, 50, or 60% (w/w). Vegetable proteins may be derived from vegetable protein sources, such as legumes and cereals, for example materials from plants of the families Fabaceae (Leguminosae), Cruciferaceae, Chenopodiaceae, and Poaceae, such as soy bean meal, lupin meal and rapeseed meal. In a particular embodiment, the vegetable protein source is material from one or more plants of the family Fabaceae, e.g., soybean, lupine, pea, or bean.

In another particular embodiment, the vegetable protein source is material from one or more plants of the family Chenopodiaceae, e.g., beet, sugar beet, spinach or quinoa. Other examples of vegetable protein sources are rapeseed, and cabbage. Soybean is a preferred vegetable protein source. Other examples of vegetable protein sources are cereals such as barley, wheat, rye, oat, maize (corn), rice, and sorghum.

The treatment according to the invention of vegetable proteins with at least one protease of the invention results in an increased solubilisation of vegetable proteins. The following are examples of % solubilised protein obtainable using the proteases of the invention in a monogastric in vitro model: At least 102%, 103%, 104%, 105%, 106%, or at least 107%, relative to a blank. The percentage of solubilised protein is determined using the monogastric in vitro model of Example 11. The term solubilisation of proteins basically means bringing protein(s) into solution. Such solubilisation may be due to protease-mediated release of protein from other components of the usually complex natural compositions such as feed.

In a further particular embodiment, the protease for use according to the invention is capable of increasing the amount of digestible vegetable proteins. The following are examples of % digested or digestible protein obtainable using the proteases of the invention in a monogastric in vitro model: At least 104%, 105%, 106%, 107%, 108%, 109%, or at least 110%, relative to a blank. The percentage of digested or digestible protein is determined using the in vitro model of Example 11.

The following are examples of % digested or digestible protein obtainable using the proteases of the invention in an aquaculture in vitro model: At least 103%, 104%, 105%, 106%, 107%, 108%, 109% or at least 110%, relative to a blank. The percentage of digested or digestible protein is determined using the aquaculture in vitro model of Example 12.

In a still further particular embodiment, the protease for use according to the invention is capable of increasing the Degree of Hydrolysis (DH) of vegetable proteins. The following are examples of Degree of Hydrolysis increase obtainable in a monogastric in vitro model: At least 102%, 103%, 104%, 105%, 106%, or at least 107%, relative to a blank. The DH is determined using the monogastric in vitro model of Example 11. The following are examples of Degree of Hydrolysis increase obtainable in an aquaculture in vitro model: At least 102%, 103%, 104%, 105%, 106%, or at least 107%, relative to a blank. The DH is determined using the aquaculture in vitro model of Example 12.

In a particular embodiment of a (pre-) treatment process of the invention, the protease(s) in question is affecting (or acting on, or exerting its solubilising influence on) the vegetable proteins or protein sources. To achieve this, the vegetable protein or protein source is typically suspended in a solvent, e.g., an aqueous solvent such as water, and the pH and temperature values are adjusted paying due regard to the characteristics of the enzyme in question. For example, the treatment may take place at a pH-value at which the activity of the actual protease is at least at least 40%, 50%, 60%, 70%, 80% or at least 90%. Likewise, for example, the treatment may take place at a temperature at which the activity of the actual protease is at least 40%, 50%, 60%, 70%, 80% or at least 90%. The above percentage activity indications are relative to the maximum activities. The enzymatic reaction is continued until the desired result is achieved, following which it may or may not be stopped by inactivating the enzyme, e.g., by a heat-treatment step.

In another particular embodiment of a treatment process of the invention, the protease action is sustained, meaning, e.g., that the protease is added to the vegetable proteins or protein sources, but its solubilising influence is so to speak not switched on until later when desired, once suitable solubilising conditions are established, or once any enzyme inhibitors are inactivated, or whatever other means could have been applied to postpone the action of the enzyme.

In one embodiment the treatment is a pre-treatment of animal feed or vegetable proteins for use in animal feed.

The term improving the nutritional value of an animal feed means improving the availability and/or digestibility of the proteins, thereby leading to increased protein extraction from the diet components, higher protein yields, increased protein degradation and/or improved protein utilisation. The nutritional value of the feed is therefore increased, and the animal performance such as growth rate and/or weight gain and/or feed conversion ratio (i.e., the weight of ingested feed relative to weight gain) of the animal is/are improved.

In a particular embodiment the feed conversion ratio is increased by at least 1%, 2%, 3%, 4%, 5%, 6%, 7%, 8%, 9% or at least 10%. In a further particular embodiment the weight gain is increased by at least 2%, 3%, 4%, 5%, 6%, 7%, 8%, 9%, 10% or at least 11%. These figures are relative to control experiments with no protease addition.

The feed conversion ratio (FCR) and the weight gain may be calculated as described in EEC (1986): Directive de la Commission du 9 avril 1986 fixant la méthode de calcul de la valeur énérgetique des aliments composés destinés à la volaille. Journal Officiel des Communautés Européennes, L130, 53-54.

The protease can be added to the feed in any form, be it as a relatively pure protease, or in admixture with other components intended for addition to animal feed, i.e., in the form of animal feed additives, such as the so-called pre-mixes for animal feed.

In a further aspect the present invention relates to compositions for use in animal feed, such as animal feed, and animal feed additives, e.g., premixes.

Apart from the protease of the invention, the animal feed additives of the invention contain at least one fat-soluble vitamin, and/or at least one water soluble vitamin, and/or at least one trace mineral. The feed additive may also contain at least one macro mineral.

Further, optional, feed-additive ingredients are colouring agents, aroma compounds, stabilisers, antimicrobial peptides, including antifungal polypeptides, and/or at least one other enzyme selected from amongst phytase (EC 3.1.3.8 or 3.1.3.26); xylanase (EC 3.2.1.8); galactanase (EC 3.2.1.89); alpha-galactosidase (EC 3.2.1.22); protease (EC 3.4.-.-), phospholipase A1 (EC 3.1.1.32); phospholipase A2 (EC 3.1.1.4); lysophospholipase (EC 3.1.1.5); phospholipase C (3.1.4.3); phospholipase D (EC 3.1.4.4); and/or beta-glucanase (EC 3.2.1.4 or EC 3.2.1.6).

In a particular embodiment these other enzymes are well-defined (as defined above for protease preparations).

Examples of antimicrobial peptides (AMP's) are CAP18, Leucocin A, Tritrpticin, Protegrin-1, Thanatin, Defensin, Lactoferrin, Lactoferricin, and Ovispirin such as Novispirin (Robert Lehrer, 2000), Plectasins, and Statins, including the compounds and polypeptides disclosed in PCT/DK02/00781 and PCT/DK02/00812, as well as variants or fragments of the above that retain antimicrobial activity.

Examples of antifungal polypeptides (AFP's) are the *Aspergillus giganteus*, and *Aspergillus niger* peptides, as well as variants and fragments thereof which retain antifungal activity, as disclosed in WO 94/01459 and WO 02/090384.

Usually fat- and water-soluble vitamins, as well as trace minerals form part of a so-called premix intended for addition to the feed, whereas macro minerals are usually separately added to the feed. A premix enriched with a protease of the invention, is an example of an animal feed additive of the invention.

In a particular embodiment, the animal feed additive of the invention is intended for being included (or prescribed as having to be included) in animal diets or feed at levels of 0.01 to 10.0%; more particularly 0.05 to 5.0%; or 0.2 to 1.0% (% meaning g additive per 100 g feed). This is so in particular for premixes.

The following are non-exclusive lists of examples of these components:

Examples of fat-soluble vitamins are vitamin A, vitamin D3, vitamin E, and vitamin K, e.g., vitamin K3.

Examples of water-soluble vitamins are vitamin B12, biotin and choline, vitamin B1, vitamin B2, vitamin B6, niacin, folic acid and panthothenate, e.g., Ca-D-panthothenate.

Examples of trace minerals are manganese, zinc, iron, copper, iodine, selenium, and cobalt.

Examples of macro minerals are calcium, phosphorus and sodium.

The nutritional requirements of these components (exemplified with poultry and piglets/pigs) are listed in Table A of WO 01/58275. Nutritional requirement means that these components should be provided in the diet in the concentrations indicated.

In the alternative, the animal feed additive of the invention comprises at least one of the individual components specified in Table A of WO 01/58275. At least one means either of, one or more of, one, or two, or three, or four and so forth up to all thirteen, or up to all fifteen individual components. More specifically, this at least one individual component is included in the additive of the invention in such an amount as to provide an in-feed-concentration within the range indicated in column four, or column five, or column six of Table A.

The present invention also relates to animal feed compositions. Animal feed compositions or diets have a relatively high content of protein. Poultry and pig diets can be characterised as indicated in Table B of WO 01/58275, columns 2-3. Fish diets can be characterised as indicated in column 4 of this Table B. Furthermore such fish diets usually have a crude fat content of 200-310 g/kg. WO 01/58275 corresponds to U.S. Ser. No. 09/779,334 which is hereby incorporated by reference.

An animal feed composition according to the invention has a crude protein content of 50-800 g/kg, and furthermore comprises at least one protease as claimed herein.

Furthermore, or in the alternative (to the crude protein content indicated above), the animal feed composition of the invention has a content of metabolisable energy of 10-30 MJ/kg; and/or a content of calcium of 0.1-200 g/kg; and/or a content of available phosphorus of 0.1-200 g/kg; and/or a content of methionine of 0.1-100 g/kg; and/or a content of methionine plus cysteine of 0.1-150 g/kg; and/or a content of lysine of 0.550 g/kg.

In particular embodiments, the content of metabolisable energy, crude protein, calcium, phosphorus, methionine, methionine plus cysteine, and/or lysine is within any one of ranges 2, 3, 4 or 5 in Table B of WO 01/58275 (R. 2-5).

Crude protein is calculated as nitrogen (N) multiplied by a factor 6.25, i.e., Crude protein (g/kg)=N (g/kg)×6.25. The nitrogen content is determined by the Kjeldahl method (A.O.A.C., 1984, Official Methods of Analysis 14th ed., Association of Official Analytical Chemists, Washington D.C.).

Metabolisable energy can be calculated on the basis of the NRC publication Nutrient requirements in swine, ninth revised edition 1988, subcommittee on swine nutrition, committee on animal nutrition, board of agriculture, national research council. National Academy Press, Washington, D.C., pp. 2-6, and the European Table of Energy Values for Poultry Feed-stuffs, Spelderholt centre for poultry research and extension, 7361 DA Beekbergen, The Netherlands. Grafisch bedrijf Ponsen & Iooijen by, Wageningen. ISBN 90-71463-12-5.

The dietary content of calcium, available phosphorus and amino acids in complete animal diets is calculated on the basis of feed tables such as Veevoedertabel 1997, gegevens over chemische samenstelling, verteerbaarheid en voederwaarde van voedermiddelen, Central Veevoederbureau, Runderweg 6, 8219 pk Lelystad. ISBN 90-72839-13-7.

In a particular embodiment, the animal feed composition of the invention contains at least one vegetable protein or protein source as defined above.

In still further particular embodiments, the animal feed composition of the invention contains 0-80% maize; and/or 0-80% sorghum; and/or 0-70% wheat; and/or 0-70% Barley; and/or 0-30% oats; and/or 0-40% soybean meal; and/or 0-10% fish meal; and/or 0-20% whey.

Animal diets can, e.g., be manufactured as mash feed (non pelleted) or pelleted feed. Typically, the milled feed-stuffs are mixed and sufficient amounts of essential vitamins and minerals are added according to the specifications for the species in question. Enzymes can be added as solid or liquid enzyme formulations. For example, a solid enzyme formulation is typically added before or during the mixing step; and a liquid enzyme preparation is typically added after the pelleting step. The enzyme may also be incorporated in a feed additive or premix.

The final enzyme concentration in the diet is within the range of 0.01-200 mg enzyme protein per kg diet, for example in the range of 0.5-25 mg enzyme protein per kg animal diet.

The protease should of course be applied in an effective amount, i.e., in an amount adequate for improving solubilisation and/or improving nutritional value of feed. It is at present contemplated that the enzyme is administered in one or more of the following amounts (dosage ranges): 0.01-200; 0.01-100; 0.5-100; 1-50; 5-100; 10-100; 0.05-50; or 0.10-10—all these ranges being in mg protease enzyme protein per kg feed (ppm).

For determining mg enzyme protein per kg feed, the protease is purified from the feed composition, and the specific activity of the purified protease is determined using a relevant assay (see under protease activity, substrates, and assays). The protease activity of the feed composition as such is also determined using the same assay, and on the basis of these two determinations, the dosage in mg enzyme protein per kg feed is calculated.

The same principles apply for determining mg enzyme protein in feed additives. Of course, if a sample is available of the protease used for preparing the feed additive or the feed, the specific activity is determined from this sample (no need to purify the protease from the feed composition or the additive).

The present invention is further described by the following examples which should not be construed as limiting the scope of the invention.

Detergent Compositions

The protease of the invention may be added to and thus become a component of a detergent composition. The detergent composition of the invention may for example be formulated as a hand or machine laundry detergent composition including a laundry additive composition suitable for pretreatment of stained fabrics and a rinse added fabric softener composition, or be formulated as a detergent composition for use in general household hard surface cleaning operations, or be formulated for hand or machine dishwashing operations.

In a specific aspect, the invention provides a detergent additive comprising the protease of the invention. The detergent additive as well as the detergent composition may comprise one or more other enzymes such as another protease, such as alkaline proteases from Bacillus, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e., pH-optimum, compatibility with other enzymatic and non-enzymatic ingredients, etc.), and the enzyme(s) should be present in effective amounts.

Suitable lipases include those of bacterial or fungal origin. Chemically modified or protein engineered mutants are included. Examples of useful lipases include lipases from *Humicola* (synonym *Thermomyces*), e.g., from *H. lanuginosa* (*T. lanuginosus*) as described in EP 258068 and EP 305216 or from *H. insolens* as described in WO 96/13580, a *Pseudomonas* lipase, e.g., from *P. alcaligenes* or *P. pseudoalcaligenes* (EP 218272), *P. cepacia* (EP 331376), *P. stutzeri* (GB 1,372,034), *P. fluorescens*, *Pseudomonas* sp. strain SD 705 (WO 95/06720 and WO 96/27002), *P. wisconsinensis* (WO 96/12012), a *Bacillus* lipase, e.g., from *B. subtilis* (Dartois et al., 1993, Biochemica et Biophysica Acta, 1131, 253-360), *B. stearothermophilus* (JP 64/744992) or *B. pumilus* (WO 91/16422). Other examples are lipase variants such as those described in WO 92/05249, WO 94/01541, EP 407225, EP 260105, W/O 95/35381, WO 96/00292, WO 95/30744, WO 94/25578, WO 95/14783, WO 95/22615, WO 97/04079 and WO 97/07202. Preferred commercially available lipase enzymes include Lipolase™ and Lipolase Ultra™ (Novozymes A/S).

Suitable amylases (alpha- and/or beta-) include those of bacterial or fungal origin. Chemically modified or protein engineered mutants are included. Amylases include, for example, alpha-amylases obtained from *Bacillus*, e.g., a special strain of *B. licheniformis*, described in more detail in GB 1,296,839. Examples of useful amylases are the variants described in WO 94/02597, WO 94/18314, WO 96/23873, and WO 97/43424, especially the variants with substitutions in one or more of the following positions: 15, 23, 105, 106, 124, 128, 133, 154, 156, 181, 188, 190, 197, 202, 208, 209, 243, 264, 304, 305, 391, 408, and 444. Commercially available amylases are Duramyl™, Termamyl™, Fungamyl™ and BAN™ (Novozymes A/S), Rapidase™ and Purastar™ (from Genencor International Inc.).

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum* disclosed in U.S. Pat. Nos. 4,435,307, 5,648,263, 5,691,178, and 5,776,757 and WO 89/09259. Especially suitable cellulases are the alkaline or neutral cellulases having colour care benefits. Examples of such cellulases are cellulases described in EP 0 495257, EP 531372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and WO 99/01544. Commercially available cellulases include Celluzyme™, and Carezyme™ (Novozymes A/S), Clazinase™, and Puradax HA™ (Genencor International Inc.), and KAC-500(B)™ (Kao Corporation).

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof as those described in WO 93/24618, WO 95/10602, and WO 98/15257. Commercially available peroxidases include Guardzyme™ (Novozymes).

The detergent enzyme(s) may be included in a detergent composition by adding separate additives containing one or more enzymes, or by adding a combined additive comprising all of these enzymes. A detergent additive of the invention, i.e., a separate additive or a combined additive, can be formulated, e.g., as a granulate, a liquid, a slurry, etc. Preferred detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods. Protected enzymes may be prepared according to the method disclosed in EP 238216.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonylphenol ethoxylate, alkylpolyglycoside, alkyldimethylamineoxide, ethoxylated fatty acid monoethanolamide, fatty acid monoethanolamide, polyhydroxy alkyl fatty acid amide, or N-acyl N-alkyl derivatives of glucosamine ("glucamides").

The detergent may contain 0-65% of a detergent builder or complexing agent such as zeolite, diphosphate, triphosphate, phosphonate, carbonate, citrate, nitrilotriacetic acid, ethylenediaminetetraacetic acid, diethylenetriaminepentaacetic acid, alkyl- or alkenylsuccinic acid, soluble silicates or layered silicates (e.g., SKS-6 from Hoecrhst).

The detergent may comprise one or more polymers. Examples are carboxymethylcellulose, poly(vinylpyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid copolymers.

The detergent may contain a bleaching system which may comprise a $H_2O_2$ source such as perborate or percarbonate which may be combined with a peracid-forming bleach activator such as tetraacetylethylenediamine or nonanoyloxybenzenesulfonate. Alternatively, the bleaching system may comprise peroxyacids of, e.g., the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in, e.g., WO 92/19709 and WO 92/19708.

The detergent may also contain other conventional detergent ingredients such as, e.g., fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the enzyme of the invention, may be added in an amount corresponding to 0.01-100 mg of enzyme protein per liter of wash liquor, preferably 0.055 mg of enzyme protein per liter of wash liquor, in particular 0.1-1 mg of enzyme protein per liter of wash liquor.

The enzyme of the invention may additionally be incorporated in the detergent formulations disclosed in WO 97/07202.

The invention described and claimed herein is not to be limited in scope by the specific embodiments herein disclosed, since these embodiments are intended as illustrations of several aspects of the invention. Any equivalent embodiments are intended to be within the scope of this invention. Indeed, various modifications of the invention in addition to those shown and described herein will become apparent to those skilled in the art from the foregoing description. Such modifications are also intended to fall within the scope of the appended claims. In the case of conflict, the present disclosure including definitions will control.

Various references are cited herein, the disclosures of which are incorporated by reference in their entireties.

EXAMPLES

Materials and Methods

Strains:
    *Bacillus subtilis* PL1801 (Diderichsen et al., 1990, Cloning of aldB, which encodes alpha-acetolactate decarboxylase, an exoenzyme from *Bacillus brevis*. J. Bacteriol., 172, 4315-4321)
    *Bacillus subtilis* MB1053
    *Bacillus subtilis* PL359837
    *Bacillus subtilis* MB1510
    *Bacillus subtilis* PL2306. This strain is the *B. subtilis* DN1885 with disrupted apr and npr genes (Diderichsen, B., Wedsted, U., Hedegaard, L., Jensen, B. R., Sjøholm, C., 1990, Cloning of aldB, which encodes alpha-acetolactate decarboxylase, an exoenzyme from *Bacillus brevis*. J. Bacteriol., 172, 4315-4321) which is also disrupted in the transcriptional unit of the known *Bacillus subtilis* cellulase gene, resulting in cellulase negative cells. The disruption was performed essentially as described in (Eds. A. L. Sonenshein, J. A. Hoch and Richard Losick (1993) *Bacillus subtilis* and other Gram-Positive Bacteria, American Society for microbiology, p. 618).

Procedure for Isolating Genomic DNA

Harvest 1.5 ml culture and resuspend in 100 microliters TEL. Leave at 37° C. for 30 min.

Add 500 microliters thiocynate buffer and leave at room temperature for 10 min.

Add 250 microliters NH$_4$Ac and leave at ice for 10 min.

Add 500 microliters CIA and mix.

Transfer to a microcentrifuge and spin for 10 min. at full speed.

Transfer supernatant to a new Eppendorf tube and add 0.54 volume cold isopropanol. Mix thoroughly.

Spin and wash the DNA pellet with 70% EtOH.

Resuspend the genomic DNA in 100 microliters TER.

| | |
|---|---|
| TE: | 10 mM Tris-HCl, pH 7.4 |
| | 1 mM EDTA, pH 8.0 |
| TEL: | 50 mg/ml Lysozym in TE-buffer |
| Thiocyanate: | 5M guanidium thiocyanate |
| | 100 mM EDTA |
| | 0.6% w/v N-laurylsarcosine, sodium salt. |
| | 60 g thiocyanate, 20 ml 0.5M EDTA, pH 8.0, 20 ml H$_2$O dissolves at 65° C. Cool down to RT and add 0.6 g N-laurylsarcosine. Add H$_2$O to 100 ml and filter it through a 0.2 micron sterile filter. |
| NH$_4$Ac: | 7.5M CH$_3$COONH$_4$ |
| TER: | 1 microgram/ml Rnase A in TE-buffer |
| CIA: | Chloroform/isoamyl alcohol 24:1 |

Purification of PCR Bands and DNA Sequencing

PCR fragment can be purified using GFX™ PCR DNA and Gel Band™ Purification Kit (Pharmacia Biotech) according to the manufacturer's instructions. The nucleotide sequences of the amplified PCR fragments are determined on an ABI PRISM™ 3700 DNA Analyzer (Perkin Elmer, USA) using 50-100 ng as template, the Taq deoxy-terminal cycle sequencing kit (Perkin Elmer, USA), fluorescent labeled terminators and 5 µmol of the sequencing primer of choice.

Media

TY: (As described in Ausubel, F. M. et al. (eds.) "Current protocols in Molecular Biology". John Wiley and Sons, 1995).

LB agar: (As described in Ausubel, F. M. et al. (eds.) "Current protocols in Molecular Biology". John Wiley and Sons, 1995).

LB-PG agar: is LB agar supplemented with 0.5% Glucose and 0.05 M potassium phosphate, pH 7.0.

Proteolytic Activity

S2A protease activity is measured using the PNA assay with succinyl-alanine-alanine-proline-phenylalnine-paranitroanilide as a substrate unless otherwise mention. The principle of the PNA assay is described in Rothgeb, T. M., Goodlander, B. D., Garrison, P. H., and Smith, L. A., Journal of the American Oil Chemists' Society, Vol. 65 (5), pp. 806-810 (1988).

Gene Expression in *Bacillus subtilis* Host

All the expressed genes in the following examples are integrated by homologous recombination on the *Bacillus subtilis* host cell genome. The genes are expressed under the control of a triple promoter system (as described in WO 99/43835), consisting of the promoters from *Bacillus licheniformis* alpha-amylase gene (amyL), *Bacillus amyloliquefaciens* alpha-amylase gene (amyQ), and the *Bacillus thuringiensis* cryIIIA promoter including stabilizing sequence. The gene coding for Chloramphenicol acetyl-transferase was used as maker. (Described in, e.g., Diderichsen, Poulsen, and Joergensen, A useful cloning vector for *Bacillus subtilis*. Plasmid 30:312 (1993)).

Example 1

Construction of Synthetic 10R Tail-Variant Genes with Savinase Signal

A synthetic 10R gene (10RS) encoding a S2A protease denoted 10R from *Nocardiopsis* sp. NRRL 18262 (WO 01/58276) was constructed which has the nucleotide sequence shown in SEQ ID NO: 1. This synthetic gene was fused by PCR in frame to the DNA coding for the signal peptide from SAVINASE™ (Novozymes) resulting in the coding sequence Sav-10RS which is shown in SEQ ID NO: 2. Several tail-variants of this construct were made. Compared to the Sav-10RS protease encoded by SEQ ID NO: 2 the tail variant construct Sav-10RS HV0 was constructed to have 8 amino acids extra in the C-terminus: QSHVQSAP (SEQ ID NO: 3) which were encoded by the following DNA sequence extension inserted in front of the TAA stopcodon of SEQ ID NO: 2:

(SEQ ID NO: 4): caatcgcatgttcaatccgctcca

Tail variant Sav-10RS HV1 was constructed to have 4 amino acids extra in the C-terminus: QSAP (SEQ ID NO: 5), with the following DNA sequence extension inserted in front of the TAA stopcodon:

(SEQ ID NO: 6): caatcggctcct

Tail variant Sav-10RS HV3 was constructed to have 2 amino acids extra in the C-terminus: QP (SEQ ID NO: 7) with the following DNA sequence extension inserted in front of the TAA stopcodon:

(SEQ ID NO: 8): caacca

Tail variant Sav-10RS HV2 was constructed to have one amino acid extra in the C-terminus: P (SEQ ID NO: 9) with the following DNA sequence extension inserted in front of the TAA stopcodon:

(SEQ ID NO: 10): cca

The 10RS gene and the four tail-variant encoding genes were integrated by homologous recombination into the *Bacillus subtilis* MB1053 host cell genome. Chloramphenicol resistant transformants were checked for protease activity on 1% skim milk LB-PG agar plates (supplemented with 6 µg/ml chloramphenicol). Some protease positive colonies were further analyzed by DNA sequencing of the insert to ensure the correct gene DNA sequence, and five strains, each comprising one of the above constructs, were selected and denoted, respectively: *B. subtilis* Sav-10RS, *B. subtilis* Sav-10RS HV0, *B. subtilis* Sav-10RS HV1, *B. subtilis* Sav-10RS HV2 and *B. subtilis* Sav-10RS HV3.

Example 2

Fermentation Yields of 10R Tail-Variants with Savinase Signal

Fermentations for the production of the tail-variant enzymes of the invention were performed on a rotary shaking table in 500 ml baffled Erlenmeyer flasks each containing 100 ml TY supplemented with 6 mg/l chloramphenicol.

Six Erlenmeyer flasks for each of the five *B. subtilis* strains from example 1 were fermented in parallel. Two of the six Erlenmeyer flasks were incubated at 37° C. (250 rpm), two at 30° C. (250 rpm), and the last two at 26° C. (250 rpm). A sample was taken from each shake flask at day 1, 2 and 3 and analyzed for proteolytic activity. The results are shown in tables 1-3. As it can be seen from tables 1-3, the effect of the tails is a surprisingly high improvement on the expression level of the protease, as measured by activity in the culture broth. The effect is most pronounced at 26° C. and 30° C., but is also evident at 37° C. as an effect observed especially at the early stage of the fermentation.

TABLE 1

Relative proteolytic activities at 37° C.

|  | Day 1 | Day 2 | Day 3 |
| --- | --- | --- | --- |
| Sav-10RS | 1.0 | 1.0 | 1.0 |
| Sav-10RS HV0 | 3.3 | 0.7 | 0.8 |
| Sav-10RS HV1 | 4.7 | 1.3 | 1.2 |
| Sav-10RS HV2 | 2.2 | 0.6 | 0.4 |
| Sav-10RS HV3 | 5.3 | 1.4 | 1.7 |

TABLE 2

Relative proteolytic activities at 30° C.

|  | Day 1 | Day 2 | Day 3 |
| --- | --- | --- | --- |
| Sav-10RS | 1.0 | 1.0 | 1.0 |
| Sav-10RS HV0 | 1.7 | 2.2 | 2.9 |
| Sav-10RS HV1 | 4.6 | 3.1 | 4.9 |
| Sav-10RS HV2 | 2.4 | 1.9 | 2.3 |
| Sav-10RS HV3 | 4.8 | 3.0 | 4.4 |

TABLE 3

Relative proteolytic activities at 26° C.

|  | Day 1 | Day 2 | Day 3 |
| --- | --- | --- | --- |
| Sav-10RS | 1.0 | 1.0 | 1.0 |
| Sav-10RS HV0 | 1.8 | 2.5 | 3.1 |
| Sav-10RS HV1 | 2.5 | 3.6 | 4.3 |
| Sav-10RS HV2 | 1.8 | 2.6 | 2.8 |
| Sav-10RS HV3 | 2.6 | 3.5 | 4.6 |

Example 3

Chromosomal Integration of Tail-Variant Genes

The following construct was used for the chromosomal integration of the tail-variant encoding genes. The coding sequence of the well-known subtilisin BPN' protease was operationally linked to a triple promoter, a marker gene was fused to this (a spectinomycin resistance gene surrounded by resolvase res-sites), and pectate lyase encoding genes from *Bacillus subtilis* were fused to the construct as flanking segments comprising the 5' polynucleotide region upstream [yfmD-ytmC-yfmB-yfmA-Pel-start], and the 3' polynucleotide region downstream [Pel-end-yflS-citS(start)] of the tail-variant encoding polynucleotide, respectively. The integrational cassette was made by the joining of several different PCR fragments. After the final PCR reaction the PCR product was used for transformation of naturally competent *B. subtilis* cells. One clone denoted PL3598-37 was selected and confirmed by sequencing to contain the correct construct.

The PL359837 clone thus contains the following:

1. The flanking regions 100% homologous to region of the *B. subtilis* genome (appears as the upstream fragment yfmD-ytmC-yfmByfmA-Pelstart and the downstream fragment Pel-end-yflS-citS(start)).
2. The Spectinomycin resistance gene flanked by Resolvase sites (res).
3. The triple promoter region plus CryIIIA mRNA stabilising leader sequence.
4. The BPN' Open Reading Frame.

Construction of Triple Promoter BPN' Cassette

A PCR fragment comprising the integrational cassette for a BPN' library was constructed, thus operably linking a triple promoter (as described in WO 99/43835; Novozymes) to a BPN' expression cassette from a *Bacillus* strain. The triple promoter is a fusion of an optimized *Bacillus* amyL-derived promoter (as shown in WO 93/10249; Novozymes) with two promoters scBAN and cryIIIA, where the first is a consensus version of the *Bacillus amyloliquefaciens* amylase BAN promoter, and the latter includes a mRNA-stabilising sequence (as described in WO 99/43835; Novozymes). Suitable primers can be derived from the publicly available sequences (Vasantha et al., Genes for alkaline protease and neutral protease from *Bacillus amyloliquefaciens* contain a large open reading frame between the regions coding for signal sequence and mature protein. J. Bacteriol. 159:811 (1984) EMBL: accession No. K02496). A KpnI and a SalI restriction site was introduced to flank the PCR fragment at each end, using the primers:

252639 (SEQ ID NO: 11): catgtgcatgtgggtaccgcaacgtt
cgcagatgctgctgaagag

251992 (SEQ ID NO: 12): catgtgcatgtggtcgaccgattatg
gagcggattgaacatgcg

The KpnI and SalI restriction sites in the PCR fragment were subsequently used to clone the fragment into a KpnI-SalI digested PecI-Spec PCR fragment. The PecI-Spec fragment comprises a Spectinomycin resistance gene inserted in the middle of the *B. subtilis* pectate lyase gene plus approx. 2.3 kb of upstream genomic DNA and approx. 1.7 kb downstream genomic DNA. The PecI-Spec fragment was produced by PCR amplification of genomic DNA from the *B. subtilis* strain MB1053, using the primers:

179541 (SEQ ID NO: 13): gcgttgagacgcgcggccgcgagcgc
cgtttggctgaatgatac

179542 (SEQ ID NO: 14): gcgttgagacagctcgagcagggaaa
aatggaaccgcttttc

Construction of MB1053

The MB1053 *B. subtilis* strain was constructed by deletion of the pectate lyase (Pel) gene through integration of a PCR product into a wild-type *B. subtilis* type strain genome. This was achieved by a PCR amplification of genomic DNA directly downstream and upstream of the pectate lyase gene of the *B. subtilis*.

The ends of the genomic DNA directly preceding and proceeding the Pel gene were elongated through primer insertion of sequences being 100% homologous to DNA sequences defined by the ends of a third PCR fragment encoding a marker gene surrounded by Resolvase (Res) sites. In this particular case the marker gene (Spec) conferred resistance to spectinomycin, and it was situated between two Res sites, altogether present on the plasmid pSJ3358 (described In U.S. Pat. No. 5,882,888). Three different PCR fragments were initially produced.

Fragment 1: this fragment covers from the yfmD gene to the middle of the Pel gene and introduces an overhang to the Res-Spec-Res cassette at the Pel gene. The size of fragment 1 is 2.8 kb. The fragment was produced by a PCR amplification chromosomal DNA from the *B. subtilis* strain PL2306, using the primers:
179541 (SEQ ID NO: 13), and
179539 with overlap to #179154 Spec primer (SEQ ID NO: 15):

ccatttgatcagaattcactggccgtcgttttacaaccattgcggaaaat agtcataggcatcc

Fragment 2: this fragment covers from the middle of the Pel gene to after the end of the CitS gene and introducing an overhang to the Res-Spec-Res cassette at the middle of the Pel gene. The size of fragment 2 is 2.3 kb. The fragment was produced by a PCR amplification of chromosomal DNA from the *B. subtilis* strain PL2306, using the primers:
179542 (SEQ ID NO: 14), and
179540 with overlap to #179153 Spec primer (SEQ ID NO: 16):

ggatccagatctggtacccgggtctagagtcgacgcggcggttcgcgtcc ggacagcaca

Fragment 3: this fragment contains the Spectinomycin gene surrounded by Res sites and DNA sequences in the ends overlapping with PCR fragment 1 and 2. The size of fragment 3 is 1.6 kb. Fragment 3 was produced by PCR amplification of plasmid pSJ3358, using the primers:

179154 (SEQ ID NO: 17): gttgtaaaacgacggccagtgaattc
                         tgatcaaatgg

179153 (SEQ ID NO: 18): ccgcgtcgacactagacacgggtacc
                         tgatctagatc Standard Conditions for the PCR Reaction For the PCR amplifications of fragment 1-3 the HiFi Expand™ PCR system (Roche) was used together with the following cycling scheme:
  5 microliters Buffer 2
  14 microliters dNTP's (1.25 mM each)
  2.5 ud 20 micro-M primer 1
  2.5 microliters 20 µM primer 2
  x microliters water
To this mix 3 microliters of DNA (apx. 100 ng) and 0.75 microliter Enzyme mix (use hot start) is added.
  Total volume is 50 microliters.
  The cycling profile is:
  1 cycle of 120 sec at 94° C.
Break.
  10 cycles of 15 sec at 94° C., 60 sec at 60° C., 240 sec at 72° C.
  20 cycles of 15 sec at 94° C., 60 sec at 60° C., (180 sec at 72° C. add 20 sec pr cycle)
  1 cycle 600 sec at 68° C.
The three PCR fragments were made and joined in later JOINING-PCR reactions. The three PCR fragments were single sharp bands and no gel purification was necessary. Only Qiagen™ PCR purification was performed prior to the following JOINING-PCR.

JOINING of fragment 1+3 (same procedure for fragment 2+3):
  5 microliters Buffer 2
  8 microliters dNTP's (1.25 mM each)
  5.0 microliters Fragment 3
  5.0 microliters Fragment 1
  9.25 microliters water
  1 cycle of 120 sec at 94° C.
Break. Add Enzyme
  10 cycles of 15 sec at 94° C., 60 sec at 60° C., 240 sec at 72° C.
Break. Add Primers
  15 cycles of 15 sec at 94° C., 60 sec at 60° C., (180 sec at 72° C. add 20 sec pr cycle)
  1 cycle 600 sec at 68° C.
After the first cycle at 94° C. for 120 sec there is a break, where 0.75 microliter enzyme mix is added.
Total volume is now 45.0 microliters.
After the initial 10 cycles, there is another break in the cycling and for fragment 1+3: 2.5 microliters (20 micro-M #179541) and 2.5 microliters (20 micro-M #179153) are added and for fragment 2+3: 2.5 microliters (20 micro-M #179542) and 2.5 microliters (20 micro-M #179154) are added and the cycling is continued for 15 cycles more.

The PCR products were then gel purified: The size of fragment 1+3 should be 3.4 kb and the size of fragment 2+3 should be 3.4 kb. These two fragments were joined in a last PCR reaction (Expand™ long system, Roche):
  5 microliters Buffer 1
  14 microliters dNTP's (1.25 mM each)
  5.0 microliters Fragment 1+3
  5.0 microliters Fragment 2+3
  17.75 microliters water
After the first cycle at 94° C. for 120 sec there is a break, where 0.75 microliter enzyme mix is added.
Total volume is now 45.0 microliters.
After the initial 10 cycles, there is another break in the cycling and 2.5 microliters (20 micro-M #179541) and 2.5 microliters (20 micro-M #179542) is added and the cycling is continued for 15 cycles more.
  1 cycle of 120 sec at 94° C.
Break. Add Enzyme
  10 cycles of 15 sec at 94° C., 60 sec at 60° C., 240 sec at 68° C.
Break. Add Primers
  15 cycles of 15 sec at 94° C., 60 sec at 60° C., 180 sec at 68° C. add 20 sec pr cycle
  1 cycle 600 sec at 68° C.
The size of the joined PCR fragment is 6.8 kb. This PCR fragment was purified using a Qiagen™ PCR purification kit, and 5 microliters of the 50 microliters eluted DNA was used to transform a standard *B. subtilis* strain. After transformation cells were spread onto LBPG-120 micrograms/ml of spectinomycin. Next day more than 1000 colonies were seen. 8 of these were checked using PCR primers from last JOINING PCR amplification yielding PCR fragment of 6.8 kb rather than the 5.2 kb expected if deletion had not occurred. Furthermore, the pectate lyase activity of the clones was checked with the Mancini Immunoassay, which showed no reactivity towards the pectate lyase activity. This taken together with the Spec resistance tells us that deletion had occurred. One such clone was selected and denoted MB1053.

Insertion of BPN' Expression Cassette Adjacent to the Res-Spec-Res in MB1053

The ligation mix of the digested PCR amplified triple promoter BPN' expression cassette and the KpnI-Sal digested PecI-Spec PCR fragment was used as template in a PCR amplification using the PCR primers #179541 and #179542. This resulted in a PCR fragment of approx. 9 kb, which was used to transform B. subtilis PL1801 (Diderichsen et al., 1990, Cloning of aldB, which encodes alpha-acetolactate decarboxylase, an exoenzyme from Bacillus brevis. J. Bacteriol., 172, 4315-4321) competent cells. The transformed cells were plated on LB-120 μg/ml Spectinomycin agar plates with skim milk. Spectinomycin resistant colonies with large skim milk clearing zones were restreaked on Spectinomycin agar plates and analysed for the integration of the PCR fragment with PCR using the primers #179541 (SEQ ID NO: 13) and #179542 (SEQ ID NO: 14).

Appearance of a 9 kb fragment indicates that the PCR fragment has been integrated into the host cell genome. Several of these clones were sequenced to confirm integration of the expression cassette, one such clone was selected and denoted PL3598-37.

Example 4

Construction of Plasmid-Borne Chromosomal Integrational Cassette

An E. coli plasmid-borne integrational cassette for a library may be constructed In vivo. An integration cassette to be used according to the method of the invention may be present on a E. coli plasmid (which is capable only of replication in E. coli, not in B. subtilis), the plasmid comprising:

i) The DNA sequence encoding the Pre-Pro-domains of the subtilisin protease commonly known as Savinase, preceded by and operably linked to ii) a DNA sequence comprising a mRNA stabilising segment derived in this particular case from the CryIIIa gene;

iii) a marker gene (a chloramphenicol resistance gene), and iv) genomic DNA from Bacillus subtilis as 5' and 3' flanking segments: The homologous 5' polynucleotide region upstream of the polynucleotide [yfmD-ytmC-yfmB-yfmA-Pel-start], and the 3' polynucleotide region downstream of the polynucleotide [Pel-end-yflS-citS(start)], respectively.

The cassette was made by several cloning steps involving digestion of pUC19 plasmid and PCR fragments with appropriate restriction endonuclease sites of several different PCR fragments in the generally used plasmid pUC19. After each ligation of a PCR fragment into a plasmid, the ligation mixture was transformed into electrocompetent DH5alpha E. coli cells that were prepared for and transformed by electroporation using a Gene Pulser™ electroporator from BIO-RAD as described by the supplier. One final plasmid construct was confirmed by sequencing to contain the correct construct as outlined above, and it was denoted pMB1508.

The pMB1508 plasmid thus contains the following:

i) The CryIIIA mRNA stabilising leader sequence including a ribosome binding sequence (RBS), operationally linked to ii) DNA encoding the Pre-Pro-domains of the subtilisin commonly known as Savinase, including KpnI and NotI sites for cloning;

iii) The chloramphenicol resistance operon;

iv) The 3' downstream flanking region [Pel-end-yflS-citS(start)] which is 99-100% homologous to the region of the B. subtilis.

The four elements listed were cloned in the pUC19 vector (Isolated from E. coli ATCC 37254; Vieira J, Messing J. The pUC plasmids, an M13 mp7-derived system for insertion mutagenesis and sequencing with synthetic universal primers. Gene 19: 259-268, 1982) in the EcoRI and SalI sites to give pMB1508. In order for the resulting plasmid to integrate efficiently to a specified site of the B. subtilis genome, a new strain was established. The new strain is a derivative of Bacillus subtilis 168 BGSC accession number: 1A1168 trpC2. The strain was made competent and transformed as described above. Using elements from the PL3598-37 clone described above, the new integration strain denoted MB1510 was established and characterized to contain the following elements from PL359837:

i) The triple promoter and the mRNA stabilising element.

ii) Flanking segments comprising the following homologous polynucleotide region [yfmD-ytmC-yfmB-yfmA-Pel-start] upstream of the triple-promoter, and the polynucleotide region [Pel-end-yflS-citS(start)] downstream of the mRNA stabilizing element.

Thus, when using MB1510 competent cells, it is possible for the pMB1508 (or derivatives thereof) to directly integrate into the genome of MB1510 where the two flanking regions in fusion with the triple-promoter and mRNA stabilising element is located, resulting in a construction where the incoming PrePro encoding DNA of pMB1508DNA has been integrated in the correct reading frame with the tripel-promoter, the mRNA stabilising element and the RBS. Thus resulting in high expression of the integrated gene from the promoter elements already present on the genome of MB1510.

Transformation efficiency was established for the B. subtilis strain MB1510 transformed with E. coli prepared plasmid pMB1508. For further testing of the potential of using this approach, the Savinase encoding gene of Bacillus clausii was PCR amplified using the two PCR primers:

```
Primer #317 (SEQ ID NO: 19)
tggcgcaatcggtaccatgggg

Primer #139 NotI (SEQ ID NO: 20)
catgtgcatgcggccgcattaacgcgttgccgcttctgcg
```

The resulting ~0.8 kb of the Savinase fragment and the pMB1508 plasmid are digested with KpnI and NotI, and the resulting fragments are then purified by agarose gel electrophoresis. The two fragments are ligated, and the ligation mixture is used to transform competent E. coli cells which are then plated on LB-agar plates or placed in liquid media for growth overnight at 37° C.; both types of media containing 50-100 micrograms/ml of Ampicillin. After incubation, a plasmid prep is made of the liquid culture. The purified plasmid is used for transformation of competent cells of MB1510 (using 10010.000 ng of plasmid per transformation. The transformed cells are plated onto TY medium with 2% skim milk and 6 micrograms/ml of chloramphenicol for selection. After overnight incubation at 37° C. clearing zones appear around those colonies wherein the integration cassette is integrated properly into the cells, indicating high Savinase expression.

This approach can also be used to make highly diverse libraries of any gene of interest expressible in B. subtilis, where rather than a gene encoding one enzyme, any expressible polynucleotide is inserted into the plasmid pMB1508 and integrated into the MB1510 strain for subsequent screening. Sequence of Plasmid pMB1508 (SEQ ID NO: 21)

The plasmid pMB1508 has the following components, indicated by basepair positions:

BP 5186-395: pUC19 sequence from *E. coli* clone ATCC 37254, Vieira J, Messing J. The pUC plasmids, an M13mp7-derived system for insertion mutagenesis and sequencing with synthetic universal primers. Gene 19: 259-268, 1982.

BP 396-1021: EcoR I cloning site (BP396-401) and the CryIIIA mRNA stabilising element. (Described in WO 96/34963)

BP 1022-1412: Encodes the Pre-Pro sequence of Savinase and the NotI cloning site. (Pre-Pro part described in, e.g., WO 96/23073, the NotI site and the spacing between the Pre-Pro and NotI was introduced by the PCR primer.

BP 1413-2512: The Bgl II cloning site (BP1413-1418) and the Chloramphenicol acetyl-transferase operon of pDN1050 (Described in, e.g., Diderichsen, Poulsen, Joergensen; A useful cloning vector for *Bacillus subtilis*. Plasmid 30:312 (1993)).

BP 2513-5185: The polynucleotide region [Pel-end-yflS-citS(start)] downstream of the pelB locus of the *B. subtilis* genome. (as it appears from the publication and corresponding database of: F. Kunst, N. Ogasawara, I. Moszer, <146 other authors>, H. Yoshikawa, A. Danchin. "The complete genome sequence of the Gram-positive bacterium *Bacillus subtilis*" Nature (1997) 390:249-256).

The *Bacillus subtilis* Strain MB1510

MB1510 has the following specific features in and around the pelB locus:
i) The triple promoter and the mRNA stabilising element including a RBS (Ribosome binding sequence).
ii) Flanking segments comprising the following homologous polynucleotide region [yfmD-ytmC-yfmB-yfmA-Pel-start] upstream of the triple-promoter, and the polynucleotide region [Pel-end-yflS-citS(start)] downstream of the mRNA stabilizing sequence.

Sequence of MB1510 Genomic Integration Region (SEQ ID NO: 22)

BP 1-2873: corresponds to sequence of *Bacillus subtilis* genome yfmD-ytmC-yfmB-yfmA-Pel-start (as it appears from the publication and corresponding database of: F. Kunst et al., "The complete genome sequence of the Gram-positive bacterium *Bacillus subtilis*", Nature (1997) 390:249-256).

BP 3102-4082: The triple promoter and CryIIIA mRNA stabilising element plus RBS. (Described above in PL3598-37 construct).

BP 4083-5718: The polynucleotide region [Pel-end-yflS-citS(start)] end of and downstream of the pelB locus of the *B. subtilis* genome (as it appears from the publication and corresponding database of: F. Kunst, N. Ogasawara, I. Moszer, <146 other authors>, H. Yoshikawa, A. Danchin. "The complete genome sequence of the Gram-positive bacterium *Bacillus subtilis*", Nature (1997) 390:249-256).

Example 5

Construction of a 2 Amino-Acid Tail-Variant Library

This example shows the construction of a tail-variant library. In this library two amino acids were introduced at the C-terminal of the 10R protein. Such a Tail-library may be made with the method described above using the following PCR primers in a PCR reaction using genomic DNA from *B. subtilis* 10RS as template:

```
1605 (SEQ ID NO: 23): gacggccagtgaattcgataaaagtgc 1606 (SEQ ID NO: 24): ccagatctctatnktnktgtacggagtct
                     aactccccaagag
``` wherein N=A, C, G or T; and K=T or G.

The resulting PCR product was digested with EcoR I and Bgl II and ligated into EcoR I and Bgl II digested pMB1508. Hereafter following the principle described above.

Chloramphenicol resistant *Bacillus subtilis* transformants were picked by a robotic colony picker from a bioassay plate and transferred into a 384 well microtiter plate (MTP) containing 0.05×TY supplemented with 6 mg/l chloramphenicol (60 microliters/well). The MTPs were incubated at 26° C. for 72 h. After incubation each well was analyzed for proteolytic activity.

The thirty *Bacillus subtilis* transformants with highest proteolytic activity were selected for determination of the two tail amino acids in each transformant by DNA sequencing, the sequencing results are summaries in table 4 and table 5.

TABLE 4 column one shows the amino acid sequence of the tail, and column two shows the number of *Bacillus subtilis* transformants sequenced with that particular AA tail sequence.

| AA Tail | No. of transformants |
| --- | --- |
| TL | 4 |
| TT | 4 |
| QL | 3 |
| TP | 3 |
| LP | 3 |
| TI | 2 |
| IQ | 2 |
| QP | 2 |
| PI | 2 |
| LT | 1 |
| TQ | 1 |
| IT | 1 |
| QQ | 1 |
| PQ | 1 |
| Total | 30 |

TABLE 5

The table shows the amino acid which could be introduced by the primer used for the library construct and the actual findings by DNA sequencing of the thirty colonies isolated from screening.

| Possibilities position 1 | Result | Possibilities position 2 | Result |
| --- | --- | --- | --- |
| K | 0 | K | 0 |
| R | 0 | R | 0 |
| T | 14 | T | 6 |
| I | 3 | I | 4 |
| Q | 6 | Q | 5 |
| P | 3 | P | 8 |
| L | 4 | L | 7 |
| Total | 30 | Total | 30 |

Example 6

Construction of *Bacillus subtilis* Strains L2, L2 HV0, and L2 HV1

A *Bacillus subtilis* strain was made analogously with the construction of the *Bacillus subtilis* strain 10RS, with the DNA coding for the pro-form of the S2A protease from *Nocardiopsis dassonvillei* subsp. *dassonvillei* DSM 43235, denoted L2, fused by PCR in frame to the DNA coding for the signal peptide from SAVINASE™ (a well-known commercial protease derived from *Bacillus clausii*, available from Novozymes, Denmark), the resulting strain was denoted *Bacillus subtilis* Sav-L2.

The DNA sequence including the coding region for the pro-mature S2A protease from *Nocardiopsis dassonvillei* subsp. *dassonvillei* DSM 43235, as amplified with primers 1423 and 1475, is shown in SEQ ID NO: 25. The corresponding encoded preform amino acid sequence for the L2 protease is shown in SEQ ID NO: 28.

```
1423 (SEQ ID NO: 26): gcttttagttcatcgatcgcatcggctgc
                      tccggcccccgtcccccag 1475 (SEQ ID NO: 27): ggagcggattgaacatgcgattaggtccg
                      gatcctgacaccccag
```

Two tail-variants of this construct were also made. Tail variant Sav-L2 HV0 was constructed to have 8 amino acids extra in the C-terminus: QSHVQSAP (SEQ ID NO: 3), by using the DNA sequence extension inserted in front of the TAA stopcodon which is shown in SEQ ID NO: 4. Tail variant Sav-L2 HV1 was constructed to have 4 amino acids extra in the C-terminus: QSAP (SEQ ID NO: 5), by using the DNA sequence extension inserted in front of the TAA stopcodon which is shown in SEQ ID NO: 6. Both tail variants had the SAVINASE™ signal-peptide encoding sequence fused in frame with the pro-mature encoding sequence, just like in Sav-L2.

The Sav-L2 gene and the two tail-variants Sav-L2 HV0 and Sav-L2 HV1 were integrated by homologous recombination on the *Bacillus subtilis* MB1053 host cell genome as outlined above. Chloramphenicol resistant transformants were checked for protease activity on 1% skim milk LB-PG agar plates (supplemented with 6 micrograms/ml chloramphenicol). Some protease positive colonies were further analyzed by DNA sequencing of the insert to confirm the correct DNA sequence, and one strain for each construct was selected and denoted *B. subtilis* Sav-L2, *B. subtilis* Sav-L2 HV0, and *B. subtilis* Sav-L2 HV1, respectively.

Example 7

Fermentation Yields of the *Bacillus* strains of Example 6

The three *B. subtilis* strains of Example 6 were fermented on a rotary shaking table in 500 ml baffled Erlenmeyer flasks containing 100 ml TY supplemented with 6 mg/l chloramphenicol. Six Erlenmeyer flasks for each of the three *B. subtilis* strains were fermented in parallel. Two of the six Erlenmeyer flasks were incubated at 37° C. (250 rpm), two at 30° C. (250 rpm), and the last two at 26° C. (250 rpm). A sample was taken from each shake flask at day 1, 2 and 3 and analyzed for proteolytic activity. The results are shown in tables 68. As it can be seen from tables 68, the effect of the tails also increases the expression level for the Sav-L2 protease from *Nocardiopsis dassonvillei* subsp. *dassonvillei* DSM 43235 when expressed in *B. subtilis*. An increase of up to 40% is observed in this experiment, but overall improvement is observed for both tail-variants at all three temperatures tested.

TABLE 6

| Relative proteolytic activities at 37° C. | | | |
|---|---|---|---|
| | Day 1 | Day 2 | Day 3 |
| Sav-L2 | 1.0 | 1.0 | 1.0 |
| Sav-L2 HV1 | 1.4 | 1.3 | 1.2 |
| Sav-L2 HV0 | 1.3 | 1.1 | 1.4 |

TABLE 7

| Relative proteolytic activities at 30° C. | | | |
|---|---|---|---|
| | Day 1 | Day 2 | Day 3 |
| Sav-L2 | 1.0 | 1.0 | 1.0 |
| Sav-L2 HV1 | 1.0 | 1.2 | 1.4 |
| Sav-L2 HV0 | 1.1 | 1.3 | 1.3 |

TABLE 8

| Relative proteolytic activities at 26° C. | | | |
|---|---|---|---|
| | Day 1 | Day 2 | Day 3 |
| Sav-L2 | 1.0 | 1.0 | 1.0 |
| Sav-L2 HV1 | 1.3 | 1.1 | 1.1 |
| Sav-L2 HV0 | 0.2 | 1.1 | 1.1 |

Example 8

10R Tail-Variants with Heterologous Pro-Regions in *Bacillus*

The DNA sequence coding for the pro-region from the L2 protease from *Nocardiopsis dassonvillei* subsp. *dassonvillei*, DSM 43235 is shown in SEQ ID NO: 29 and the corresponding amino acid sequence is shown in SEQ ID NO: 30. A *Bacillus subtilis* strain denoted L210R, similar to the *Bacillus subtilis* strain 10RS, but with the DNA coding for the pro-region of the L2 replacing the pro-region of 10RS, was made. The entire L210R protease encoding sequence incl. the pro-region of L2, is shown in SEQ ID NO: 31.

Two tail variants of the above construct were also made. Tail variant HV0 was constructed to have 8 amino acids extra in the C-terminus: QSHVQSAP (SEQ ID NO: 3) with the DNA shown in SEQ ID NO: 4 inserted in front of the TAA stopcodon of the encoding sequence. Tail variant HV1 was constructed to have 4 amino acids extra in the C-terminus: QSAP (SEQ ID NO: 5) with the DNA sequence shown in SEQ ID NO: 6 inserted in front of the TAA stopcodon of the encoding sequence.

The 10RL2) construct and the two tail variants were integrated by homologous recombination on the *Bacillus subtilis* MB1053 host cell genome. Chloramphenicol resistant transformants were checked for protease activity on 1% skim milk LB-PG agar plates (supplemented with 6 micrograms/ml chloramphenicol). Some protease positive colonies were further analyzed by DNA sequencing of the insert to confirm the correct DNA sequence, and a strain for each construct was selected, and denoted *B. subtilis* L210R, *B. subtilis* L210R HV0, and *B. subtilis* L210R HV1, respectively.

Example 9

Fermentation Yields of 10R Tail-Variants with Heterologous Pro-Region

The six *B. subtilis* strains 10RS, 10RS HV0, 10RS HV1, L210R, 1210R HV0, and L210R HV1, were fermented on a rotary shaking table in 500 ml baffled Erlenmeyer flasks containing 100 ml TY supplemented with 6 mg/l chloramphenicol. Six Erlenmeyer flasks for each of the *B. subtilis* strains were fermented in parallel. Two of the six Erlenmeyer flasks were incubated at 37° C. (250 rpm), two at 30° C. (250 rpm), and the last two at 26° C. (250 rpm). A sample was taken from each shake flask at day 1, 2 and 3 and analyzed for proteolytic activity The results are shown in FIG. 1, and in tables 9-11. As it can be seen from the results, the effect of the exchange of the proregion from 10R with the proregion from the L2 protease resulted in a surprisingly high improvement on the expression level of the 10R protease as measured by proteolytic activity in the culture broth at 37° C. The effect is most pronounced in the two tail variants.

TABLE 9

Relative proteolytic activities at 37° C.

|  | Day 1 | Day 2 | Day 3 |
|---|---|---|---|
| 10RS | 1.0 | 1.0 | 1.0 |
| 10RS HV0 | 3.7 | 8.9 | 3.5 |
| 10RS HV1 | 3.9 | 8.5 | 4.3 |
| L210R | 1.9 | 2.3 | 1.6 |
| L210R HV0 | 5.3 | 14.4 | 7.3 |
| L210R HV1 | 9.1 | 20.9 | 7.6 |

TABLE 10

Relative proteolytic activities at 30° C.

|  | Day 1 | Day 2 | Day 3 |
|---|---|---|---|
| 10RS | 1.0 | 1.0 | 1.0 |
| 10RS HV0 | 2.8 | 3.1 | 4.3 |
| 10RS HV1 | 3.6 | 3.6 | 4.9 |
| L210R | 0.6 | 0.4 | 0.9 |
| L210R HV0 | 3.5 | 3.2 | 4.5 |
| L210R HV1 | 3.7 | 3.2 | 4.5 |

TABLE 11

Relative proteolytic activities at 26° C.

|  | Day 1 | Day 2 | Day 3 |
|---|---|---|---|
| 10RS | 1.0 | 1.0 | 1.0 |
| 10RS HV0 | 2.6 | 3.0 | 2.8 |
| 10RS HV1 | 3.7 | 3.3 | 3.1 |
| L210R | 0.4 | 0.7 | 0.4 |
| L210R HV0 | 2.3 | 2.1 | 1.9 |
| L210R HV1 | 2.2 | 1.7 | 1.7 |

Example 10

Repeat of Examples 1-9 with Other 10R-Like Proteases

Completely analogously with the Examples 1 through 9, similar experiments are carried out with the proteases of the following *Nocardiopsis* strains:

(a) *Nocardiopsis dassonvillei* NRRL 18133 as described in WO 88/03947;

(b) *Nocardiopsis* sp. NRRL 18262 as described in WO 88/03947, the DNA and amino acid sequences of the protease derived from *Nocardiopsis* sp. NRRL 18262 are shown in DK patent application no. 1996 00013, and WO 01/58276 describes the use in animal feed of acid-stable proteases related to the protease derived from *Nocardiopsis* sp. NRRL no. 18262;

(c) *Nocardiopsis alba* DSM 15647; the amino acid sequence of the protease is SEQ ID NO: 33, the encoding nucleotide sequence is SEQ ID NO: 32; the gene is isolated from the genomic DNA of this strain by PCR-amplification using the two primers:

```
1421 (SEQ ID NO: 34): gttcatcgatcgcatcggctgcgaccggc
                      ccctcccccagtc 1604 (SEQ ID NO: 35): gcggatcctatcaggtgcgcagggtcaga
                      cc.
```

(d) *Nocardiopsis prasina* DSM 15648; the amino acid sequence of the protease is SEQ ID NO: 37, the encoding nucleotide sequence is SEQ ID NO: 36; the gene is isolated from the genomic DNA of this strain by PCR-amplification using the two primers:

```
1346 (SEQ ID NO: 38): gttcatcgatcgcatcggctgccaccgga
                      ccgctcccccagtc 1602 (SEQ ID NO: 39): gcggatcctattaggtccggagacggacg
                      ccccaggag.
```

(e) *Nocardiopsis prasina* DSM 15649; the amino acid sequence of the protease is SEQ ID NO: 41, the encoding nucleotide sequence is SEQ ID NO: 40; the gene is isolated from the genomic DNA of this strain by PCR-amplification using the two primers:

```
1603 (SEQ ID NO: 42): gttcatcgatcgcatcggctgccaccgga
                      ccactcccccagtc,
and 1602 (SEQ ID NO: 39): gcggatccta ttaggtccgg
                      agacggacgc cccaggag.
```

1602 (SEQ ID NO: 39): qcqqatccta ttaggtccqq aqacqqacqc cccaqqaq.

Example 11

In Vivo Monogastric Performance of a 10R-Like Protease from DSM 43235

The performance of the *Nocardiopsis dassonvillei* subspecies *dassonvillei* DSM 43235 protease assayed in a monogastric in vitro digestion model. The performance of a purified preparation of the mature part of the protease having SEQ ID NO: 28 (prepared as described above) was tested in an in vitro model simulating the digestion in monogastric animals. In particular, the protease was tested for its ability to improve solubilisation and digestion of maize/SBM (maize/soybean meal) proteins. In the tables below, this protease is designated "protease of the invention."

The in vitro system consisted of 15 flasks in which maize/SBM substrate was initially incubated with HCl/pepsin-simulating gastric digestion—and subsequently with pancreatin-simulating intestinal digestion. 10 of the flasks were dosed with the protease at the start of the gastric phase whereas the remaining flasks served as blanks. At the end of the intestinal incubation phase samples of in vitro digesta were removed and analyzed for solubilized and digested protein.

TABLE 12

Outline of in vitro digestion procedure

| Components added | pH | Temperature | Time course | Simulated digestion phase |
|---|---|---|---|---|
| 10 g maize/-SBM substrate (6:4), 41 ml HCl (0.105M) | 3.0 | 40° C. | t = 0 min | Mixing |
| 5 ml HCl (0.105M)/pepsin (3000 U/g substrate), 1 mL protease of the invention | 3.0 | 40° C. | t = 30 min | Gastric digestion |
| 16 ml H$_2$O | 3.0 | 40° C. | t = 1.0 hour | Gastric digestion |
| 7 ml NaOH (0.39M) | 6.8 | 40° C. | t = 1.5 hours | Intestinal digestion |
| 5 ml NaHCO$_3$ (1M)/pancreatin (8 mg/g diet) | 6.8 | 40° C. | t = 2.0 hours | Intestinal digestion |
| Terminate incubation | 7.0 | 40° C. | t = 6.0 hours | |

Conditions
Substrate: 4 g SBM, 6 g maize (premixed)
pH: 3.0 stomach step/6.8-7.0 intestinal step
HCl: 0.105 M for 1.5 hours (i.e., 30 min HCl-substrate premixing)
pepsin: 3000 U/9 diet for 1 hour
pancreatin: 8 mg/g diet for 4 hours
temperature: 40° C.
Replicates: 5
Solutions
0.39 M NaOH
0.105 M HCl
0.105 M HCl containing 6000 U pepsin per 5 ml
1 M NaHCO$_3$ containing 16 mg pancreatin per ml
125 mM NaAc-buffer, pH 6.0
Enzyme Protein Determinations The amount of protease enzyme protein (in what follows, Enzyme Protein is abbreviated EP) is calculated on the basis of the A$_{280}$ values and the amino acid sequences (amino acid compositions) using the principles outlined in S. C. Gill & P. H. von Hippel, Analytical Biochemistry 182, 319-326 (1989).
Experimental Procedure for In Vitro Model The experimental procedure was according to the above outline. pH was measured at time 1, 2.5, and 5.5 hours. Incubations were terminated after 6 hours and samples of 30 ml were removed and placed on ice before centrifugation (10000×g, 10 min, 4° C.). Supernatants were removed and stored at −20° C.
Analysis All samples were analysed for % degree of protein with the OPA method as well as content of solubilised and digested protein using gel filtration.
DH Determination by the OPA-Method The Degree of Hydrolysis (DH) of protein in different samples was determined using an semi-automated microtiter plate based colorimetric method (Nielsen, Petersen, Dambmann, Improved method for determining food protein degree of hydrolysis. J. Food Sci. 2001, 66, 642-646). The OPA reagent was prepared as follows: 7.620 g di-Na tetraborate decahydrate and 200 mg sodiumdodecyl sulphate (SDS) were dissolved in 150 ml deionized water. The reagents were completely dissolved before continuing. 160 mg o-phthal-dialdehyde 97% (OPA) was dissolved in 4 ml ethanol. The OPA solution was transferred quantitatively to the above-mentioned solution by rinsing with deionized water. 176 mg dithiothreitol 99% (DTT) was added to the solution that was made up to 200 ml with deionized water. A serine standard (0.9516 meqv/l) was prepared by solubilising 50 mg serine (Merck, Germany) in 500 ml deionized water.

The sample solution was prepared by diluting each sample to an absorbance (280 nm) of about 0.5. Generally, supernatants were diluted (100×) using an automated Tecan dilution station (Männedorf, Switzerland). All other spectrophotometer readings were performed at 340 nm using deionized water as the control. 25 microliters of sample, standard and blind was dispensed into a microtiter plate. The micro-titer plate was inserted into an iEMS MF reader (Labsystems, Finland) and 200 microliters of OPA reagent was automatically dispensed. Plates were shaken (2 min; 700 rpm) before measuring absorbance. Finally, the DH was calculated. Eight-fold determination of all samples was carried out.
Estimation of Solubilised and Digested Protein The content of solubilised protein in supernatants from in vitro digested samples was estimated by quantifying crude protein (CP) using gel filtration HPLC. Supernatants were thawed, filtered through 0.45 micro-m polycarbonate filters and diluted (1:50, v/v) with H$_2$O. Diluted samples were chromatographed by HPLC using a Superdex Peptide PE (7.5× 300 mm) gel filtration column (Global). The eluent used for isocratic elution was 50 mM sodium phosphate buffer (pH 7.0) containing 150 mM NaCl. The total volume of eluent per run was 26 ml and the flow rate was 0.4 ml/min. Elution profiles were recorded at 214 nm and the total area under the profiles was determined by integration. To estimate protein content from integrated areas, a calibration curve ($R^2$=0.9993) was made from a dilution series of an in vitro digested reference maize/SBM sample with known total protein content. The protein determination in this reference sample was carried out using the Kjeldahl method (determination of % nitrogen; A.O.A.C. (1984) Official Methods of Analysis 14th ed., Washington D.C.).

The content of digested protein was estimated by integrating the chromatogram area corresponding to peptides and amino acids having a molecular mass of 1500 Daltons or below (Savoie, Gauthier, Dialysis Cell For The In-vitro Measurement Of Protein Digestibility. J. Food Sci. 1986, 51, 494-498; Babinszky, Van, Boer, Den, An In-vitro Method for Prediction of The Digestible Crude Protein Content in Pig Feeds. J. Sci. Food Agr. 1990, 50, 173178; Boisen, Eggum, Critical Evaluation of In-vitro Methods for Estimating Digestibility in Simple-Stomach Animals. Nutrition Research Reviews 1991, 4, 141-162). To determine the 1500 Dalton dividing line, the gel filtration column was calibrated using cytochrome C (Boehringer, Germany), aprotinin, gastrin 1, and substance P (Sigma Aldrich, USA), as molecular mass standards.
Results The results shown in Tables 13 and 14 below indicate that the protease increased the Degree of Hydrolysis (DH), as well as soluble and digestible protein significantly.

TABLE 13

Degree of Hydrolysis (DH), absolute and relative values

| Enzyme | | Of total protein | | Relative to blank | |
|---|---|---|---|---|---|
| (dosage in mg EP/kg feed) | n | % DH | SD | % DH | % CV |
| Blank | 5 | 26.84 $^a$ | 0.69 | 100.0 $^a$ | 2.57 |
| Protease of the invention (100) | 5 | 28.21 $^b$ | 0.35 | 105.1 $^b$ | 1.25 |

Different letters within the same column indicate significant differences (1-way ANOVA, Tukey-Kramer test, P < 0.05).
SD = Standard Deviation.
% CV = Coefficient of Variance = (SD/mean value) × 100%

TABLE 14

Solubilised and digested crude protein measured by ÄKTA HPLC

| Enzyme | | Of total protein | | | | Relative to blank | | | |
|---|---|---|---|---|---|---|---|---|---|
| (dosage in mg EP/kg feed) | n | % dig. CP | SD | % sol. CP | SD | % dig. CP | CV % | % sol. CP | CV % |
| Blank | 5 | 54.1 $^a$ | 1.1 | 90.1 $^a$ | 1.1 | 100.0 $^a$ | 2.0 | 100.0 $^a$ | 1.2 |
| Protease of the invention (50) | 5 | 57.7 $^b$ | 1.1 | 93.2 $^b$ | 1.4 | 106.7 $^b$ | 1.9 | 103.4 $^b$ | 1.5 |
| (100) | 5 | 58.9 $^b$ | 0.8 | 94.8 $^b$ | 0.9 | 108.9 $^b$ | 1.3 | 105.2 $^b$ | 0.9 |

Different letters within the same column indicate significant differences (1-way ANOVA, Tukey-Kramer test, P < 0.05).
SD = Standard Deviation.
% CV = Coefficient of Variance = (SD/mean value) × 100%

Example 12

In Vitro Aquaculture Performance of 10R-Like Protease from DSM 43235

Performance of the protease from *Nocardiopsis dassonvillei* subsp. *dassonvillei* DSM 43235 in an aquaculture in vitro model. The protease preparation as described in Example 3 was tested in an aquaculture in vitro model simulating the digestion in coldwater fish. The in vitro system consisted of 15 flasks in which SBM substrate was initially incubated with HCl/pepsin—simulating gastric digestion—and subsequently with pancreatin—simulating intestinal digestion. 10 of the flasks were dosed with the protease at the start of the gastric phase whereas the remaining 5 flasks served as blanks. At the end of the intestinal incubation phase samples of in vitro digesta were removed and analyzed for solubilized and digested protein.

TABLE 15

Outline of aqua in vitro digestion procedure

| Components added | pH | Temperature | Time course | Simulated digestion phase |
|---|---|---|---|---|
| 10 g extruded SBM substrate, 62 mL HCl (0.155M)/pepsin (4000 U/g substrate), 1 mL of the protease of the invention | 3.0 | 15° C. | t = 0 min | Gastric digestion |
| 7 mL NaOH (1.1M) | 6.8 | 15° C. | t = 6 hours | Intestinal digestion |
| 5 mL NaHCO$_3$ (1M)/ pancreatin (8 mg/g diet) | 6.8 | 15° C. | t = 7 hours | Intestinal digestion |
| Terminate incubation | 7.0 | 15° C. | t = 24 hours | |

Conditions
Substrate: 10 g extruded SBM
pH: 3.0 stomach step/6.8-7.0 intestinal step
HCl: 0.155 M for 6 hours
Pepsin: 4000 U/g diet for 6 hours
Pancreatin: 8 mg/g diet for 17 hours
Temperature: 15° C.
Replicates: 5
Solutions
1.1 M NaOH
0.155 M HCl/pepsin (4000 U/g diet)
1 M NaHCO$_3$ containing 16 mg pancreatin/mL
125 mM NaAc-buffer, pH 6.0
Experimental Procedure for Aqua In Vitro Model The experimental produce was according to the above outline. pH was measured at time 1, 5, 8 and 23 hours. Incubations were terminated after 24 hours and samples of 30 mL were removed and placed on ice before centrifugation (13000×g, 10 min, 0° C.). Supernatants were removed and stored at −20° C.
Analysis All supernatants were analyzed using the OPA method (% degree of hydrolysis) and by ÄKTA HPLC to determine solubilised and digested protein (see monogastric example).
Pre-Treatment of In Vitro Supernatants with EASY SPE Columns Before analysis on ÄKTA HPLC supernatants from the in vitro system were pretreated using solid-phase sample purification. This was done to improve the chromatography and thereby prevent unstable elution profiles and baselines. The columns used for extraction were solid phase extraction columns (Chromabond EASY SPE Columns from Macherey-Nagel). 2 mL milliQ water was eluted through the columns by use of a vacuum chamber (vacuum 0.15×100 kPa). Subsequently 3 mL in vitro sample was dispensed onto the column and eluted (vacuum 0.1×100 kPa), the first ½ mL of eluted sample was thrown away and a clean tube was placed beneath the column, then the rest of the sample was eluted and saved for further dilution.

Results

The results shown in Tables 16 and 17 below indicate that the protease significantly increased Degree of hydrolysis and protein digestibility.

TABLE 16

Degree of Hydrolysis (DH) measured by the OPA method, absolute and relative values

| Enzyme | | Of total protein | | Relative to blank | |
|---|---|---|---|---|---|
| (mg EP/kg diet) | n | % DH | SD | % DH | % CV |
| Blank | 5 | 21.30 $^a$ | 0.52 | 100.0 $^a$ | 2.42 |
| Protease of the invention (50) | 5 | 21.98 $^b$ | 0.22 | 103.2 $^b$ | 1.00 |

Different letters within the same column indicate significant differences (1-way ANOVA, Tukey-Kramer test, P < 0.05).
SD = Standard Deviation.
% CV = Coefficient of Variance = (SD/mean value) × 100%

TABLE 17

Solubilised and digested crude protein measured by ÄKTA HPLC, absolute and relative values

| Enzyme | | Of total protein | | | | Relative to blank | | | |
|---|---|---|---|---|---|---|---|---|---|
| (mg EP/kg diet) | N | % CP dig | SD | % CP sol | SD | % CP dig | % CV | % CP sol | % CV |
| Blank | 5 | 50.0 $^a$ | 2.2 | 89.9 $^a$ | 3.2 | 100.0 $^a$ | 4.5 | 100.0 $^a$ | 3.5 |
| Protease of the invention (50) | 5 | 52.3 $^b$ | 1.1 | 91.4 $^a$ | 1.5 | 104.8 $^b$ | 2.1 | 101.7 $^a$ | 1.6 |
| (100) | 5 | 53.4 $^b$ | 0.4 | 91.6 $^a$ | 1.0 | 107.0 $^b$ | 0.7 | 101.9 $^a$ | 1.1 |

Different letters within the same column indicate significant differences (1-way ANOVA, Tukey-Kramer test, P < 0.05).
SD = Standard Deviation.
% CV = Coefficient of Variance = (SD/mean value) × 100%.

Example 13

Fermentation and Activity of 10R Tail-Variants TQ and TP with Savinase Signal

Two of the *B. subtilis* strains of Example 5, strain 209 with the amino acid tail-variant TQ, and strain 211 with the tail-variant TP, together with *B. subtilis* Sav-10RS, were fermented on a rotary shaking table in 500 ml baffled Erlenmeyer flasks containing 100 ml TY supplemented with 6 mg/l chloramphenicol. Twelve Erlenmeyer flasks for each of the three *B. subtilis* strains were fermented in parallel. Four of the twelve Erlenmeyer flasks were incubated at 37° C. (250 rpm), four at 30° C. (250 rpm), and the last four at 26° C. (250 rpm). A sample was taken from each shake flask at day 1, 2 and 3 and analyzed for proteolytic activity. The results are shown in tables 18 to 20 below.

As it can be seen from tables below, the effect of the 2 amino acid tails is a surprisingly high improvement on the yield of the protease, as measured by activity in the culture broth. The effect of the 2 amino acid tails is comparable to the effect observed for Sav-10RS HV1 and Sav-10RS HV3 in Example 1.

TABLE 18

Relative proteolytic activities at 37° C.

| | 1 | 2 | 3 |
|---|---|---|---|
| 10R synt-15 | 1.0 | 1.0 | 1.0 |
| 209 | 7.0 | 7.0 | 6.0 |
| 211 | 7.2 | 7.7 | 4.9 |

TABLE 19

Relative proteolytic activities at 30° C.

| | 1 | 2 | 3 |
|---|---|---|---|
| 10R synt-15 | 1.0 | 1.0 | 1.0 |
| 209 | 4.5 | 3.6 | 4.9 |
| 211 | 4.0 | 4.1 | 5.0 |

TABLE 20

Relative proteolytic activities at 26° C.

| | 1 | 2 | 3 |
|---|---|---|---|
| 10R synt-15 | 1.0 | 1.0 | 1.0 |
| 209 | 6.4 | 4.3 | 4.0 |
| 211 | 3.7 | 4.1 | 4.2 |

Example 14

Synthetic Shuffled 10R-Like Protease Tail-Variants with Signal

Another synthetic tail variant 10R protease encoding gene, denoted G-MAT-22, was constructed with a signal peptide, and the 8 amino acid C-terminal tail of SEQ ID NO: 3, and introduced into a *Bacillus subtilis* host for expression. A surprisingly high yield of protease was achieved (data not shown). The full coding DNA sequence of G-MAT-22 is shown in SEQ ID NO: 44, and the encoded pre-pro-protease is shown in SEQ ID NO: 45. The G-mat-22 protease is an alpha-lytic protease-like enzyme (peptidase family S1E—old notation: S2A). This protease has a higher temperature optimum (at pH 9) than the 10R protease, as shown in FIG. 1.

Example 15

Shuffled Pro-sequences of 10R-Like Proteases

Recombination of protease genes can be made independently of the specific sequence of the parents by synthetic shuffling as described in Ness, J. E. et al 2002 [Nature Biotechnology, Vol. 20 (12). pp. 1251-1255, 2002]. Synthetic oligonucleotides degenerated in their DNA sequence to provide the possibility of all amino acids found in the set of parent proteases are designed and the genes assembled according to the reference. The shuffling can be carried out for the full length sequence or for only part of the sequence and then later combined with the rest of the gene to give a full length sequence.

In this example the amino acid sequence for the Pro-peptide part of the parent proteases given in SEQ ID NO: 28; SEQ ID NO: 33; SEQ ID NO: 37; SEQ ID NO: 41; SEQ ID NO: 43; or SEQ ID NO: 45 is encoded by a set of oligonucleotides and the resulting shuffled gene fragments are combined into the context of the full length protease gene, which then consists of DNA coding for the signal sequence, the (shuffled) Pro-peptide, and in this case the mature protein of 10R protease. Examples of shuffled Pro-peptide sequences are shown in SEQ ID NO: 46 (02.19), SEQ ID NO: 47 (G-2.73), SEQ ID NO: 48 (G-1.43), SEQ ID NO: 49 (G-2.6), SEQ ID NO: 50 (G-2.5), SEQ ID NO: 51 (G-2.3), SEQ ID NO: 52 (G-1.4), and SEQ ID NO: 53 (G-1.2).

The complete protease encoding genes were inserted into the genome of *B. subtilis* by homologous recombination as described above, and the proteases expressed in shake-flasks using a rich media. The fermentation was carried out for 5 days at 30° C. and the supernatant isolated by centrifugation prior to measuring the protease activity. As control a *B. subtilis* clone expressing the wild type protease 10R from *Nocardiopsis* sp. NRRL 18262 from an identical construction protocol was fermented under the same conditions. The protease activity was calculated and is presented in the table below relatively to the activity of the wild type 10R protease. Clearly the heterologous pro-regions provide an advantage over the native pro-region of the 10R protease.

TABLE 21

Relative activity of 10R protease expressed with heterologous shuffled pro-peptides.

| | Rel. acivity |
|---|---|
| 10R | 1.0 |
| G-1.2 | 2.9 |
| G-1.4 | 1.4 |
| G-2.3 | 1.6 |
| G-2.4 | 3.4 |
| G-2.5 | 3.0 |
| G-2.6 | 4.2 |
| G-2.7 | 1.6 |

Example 16

In Vivo Monogastric Performance of Tail-Variant 10R-HV1

This example describes a dose/response study with the four amino acid tail variant HV1 of the 10R protease in the monogastric in vitro model using 10, 25, 50, and 100 mg EP/kg, and using 10R protease as benchmark or control. The tail variant 10R-HV1 was constructed to have 4 amino acids extra in the C-terminus: QSAP (SEQ ID NO: 5) as described above.

In Vitro Conditions:
Substrate: 4 g SBM, 6 g maize (premixed)
pH: 3.0 stomach step/6.8-7.0 intestine step
HCl: 0.105 M for 1.5 hours (i.e., 30 min HCl-substrate premixing)
Pepsin: 3000 U/g diet for 1 hour
Pancreatin: 8 mg/g diet for 4 hours.
Incubation: 40° C.
Replica: 5
Enzymes;
10R protease: FFE-2003-00047; batch PPA21400; 154 mg EP/g product.
Freezedried 10R-HV1 FFE-2003-00077; 370 mg EP/g product
Solution A: 10R, 100 mg EP/kg Diet:
100 mg EP/kg diet ~1 mg EP/flask $\Rightarrow$ 1 mg EP/mL
(1 mg EP/mL*10 mL)/154 mg EP/g product=0.0649 g
Prepare 10 mL: Dissolve 0.0649 g enzyme in 10 mL NaAc buffer.
Solution C: 10R-HV1, 100 mg EP/kg Diet:
100 mg EP/kg diet ~1 mg EP/flask $\Rightarrow$ 1 mg EP/mL
(1 mg EP/mL*20 mL)/370 mg EP/g product=0.05405 g
Prepare 20 mL: Dissolve 0.0541 g enzyme in 20 mL NaAc buffer.
Solution D: 10R-HV1, 50 mg EP/kg Diet:
50 mg EP/kg diet ~0.50 mg EP/flask via 1 ml=0.50 mg EP/ml
Prepare 10 mL: Dilute C 2 times: 5 ml solution C+5 ml 125 mM NaAc-buffer
Solution E: 10R-HV1, 25 mg EP/kg Diet:
25 mg EP/kg diet ~0.25 mg EP/flask via 1 ml=0.25 mg EP/ml
Prepare 12 mL: Dilute C 4 times: 3 ml solution C+9 ml 125 mM NaAc-buffer
Solution F: 10R-HV1, 10 mg EP/kg Diet:
25 mg EP/kg diet ~0.25 mg EP/flask via 1 ml=0.25 mg EP/ml
Prepare 10 mL: Dilute C 10 times: 1 ml solution C+9 ml 125 mM NaAc-buffer
Substrates:
Premix (40% SBM/60% maize), FFS-2002-00121
The 10 g sample contains 6 g maize and 4 g SBM giving a calculated protein content of 23.48% of protein (~2.35 g/flask).
Chemicals:
4.005 M HCl, AT-1-00061/29
4.007 M NaOH, AT-1-00002/36
Pancreatin FFE-2002-00052, 8×USP
Pepsin FFE-2003-00048, 471 U/mg
NaOH 0.39 M:
Prepare 500 mL:
48.97 mL 3.982 M NaOH, fill with milliQ to 500 mL.
HCl1 Solution 0.105 M
Prepare 2000 mL:
52.43 mL of 4.005HCl, fill with milliQ up to 2000 mL
HCL2 (HC/Pepsin) Solution: 0.105 M Containing 30000 U Pepsin/5 mL
Prepare 250 mL,
Take out approx. 150 mL from the HCl-solution, add 3.18 g pepsin and fill up to 250 mL with the HCl solution.
125 mM NaAc-Buffer, pH 6.0:
Prepared from a 2 M NaAc-buffer (KLu 04-07-2003/lab book 14169 p. 104)
$\rightarrow$12.5 mL 2 M NaAc-buffer, fill up to 200 mL with milliQ
Pancreatin Dissolved in 1 M NaHCO$_3$ Containing 8 mg Pancreatin/g Diet:

NaHCO$_3$-pancreatin is pre made, divided into portions and frozen. Made 29-042003 and frozen, it is slowly thawed in refrigerator over night. The stock preparation is described in lab. book 14165 page 068.

Flow Scheme:

In the Premixing phase (t=0), 10 g substrate is mixed with 41 ml HCl1; then in the gastral phase (t=30 min) 5 ml HCl-2 (HCl/pepsin)+1 ml enzyme (or buffer) is added, and later (t=1 h) the pH is measured and 16 ml water is added; and then in the intestinal phase (t=1 h 30 min) 7 ml 0.39 NaOH is added, and later (t=2 h) 5 ml NaHCO$_3$/pancreatin is added and the pH is measured again twice (t=2 h 30 min & t=5 h 30 min); and finally (t=6 h) 30 ml suspension is sampled for centrifugation. Each supernatant is immediately and carefully removed from the centrifuge tube into glass tubes. The supernatants are split in two aliquots for further analysis. Results are shown in table 22.

TABLE 22

Treatment of samples in the monogastric in vitro model.

| Sample | Enzyme Solution | Enzyme | pH | Enzyme dose/ kg diet: | Pepsin U/g diet: | Pancreatin mg/g diet: |
|---|---|---|---|---|---|---|
| 1-5 | 1 ml Buffer | Blank | 3.0 | 0 mg EP | 3000 | 8.0 |
| 6-10 | 1 ml Solution A | 10R (FFE-2003-00047) | 3.0 | 100 mg EP | 3000 | 8.0 |
| 11-15 | 1 ml Solution C | 10R-HV1 (PPA22873) | 3.0 | 100 mg EP | 3000 | 8.0 |
| 16-20 | 1 ml Solution D | 10R-HV1 (PPA22873) | 3.0 | 50 mg EP | 3000 | 8.0 |
| 21-25 | 1 ml Solution E | 10R-HV1 (PPA22873) | 3.0 | 25 mg EP | 3000 | 8.0 |
| 26-30 | 1 ml Solution F | 10R-HV1 (PPA22873) | 3.0 | 10 mg EP | 3000 | 8.0 |

Soluble and Digestible Protein:

The changes in the levels of soluble and digestible crude protein in the soluble phase of the hydrolysates were determined using an ÄKTA HPLC (Superdex 30 peptide column). The results are shown in Table 23.

At a 10R-HV1 dose of 100 mg EP/kg diet, the level of Digestible protein was significantly increased by 9.8%, compared to Blank. The control 10R showed a relative improvement of 7.7%. With the lower enzyme concentrations (50, 25, and 10 mg EP/kg diet) the relative improvements of Digestible protein were 5.7%, 3.3% and 0.7%, respectively.

TABLE 23

HPLC results with 10R-HV1 and 10R showing the percentual changes in digestible CP and soluble CP relative to blank. Different letters on top of the bars indicate significant differences (1-ANOVA, Tukey, 95%).

| MoFi030043, day 2 Enzyme | | Of total protein | | | | Relative to blank | | | |
|---|---|---|---|---|---|---|---|---|---|
| [mg EP/kg] | n | % dig. CP | SD | % sol. CP | SD | % dig. CP | CV % | % sol. CP | CV % |
| Blank | 11 | 54.8 | 1.2 | 83.9 | 1.6 | 100.0$^a$ | 2.3 | 100.0$^a$ | 1.9 |
| 10R HV1 [100] | 5 | 60.2 | 0.8 | 88.3 | 1.1 | 109.8$^e$ | 1.3 | 105.3$^c$ | 1.3 |
| 10R HV1 [50] | 5 | 58.0 | 0.6 | 86.9 | 0.8 | 105.7$^{cd}$ | 1.1 | 103.6$^{bc}$ | 0.9 |
| 10R HV1 [25] | 5 | 56.7 | 0.8 | 86.3 | 1.0 | 103.3$^{bc}$ | 1.4 | 102.9$^{bc}$ | 1.2 |
| 10R HV1 [10] | 5 | 55.2 | 1.3 | 84.3 | 1.9 | 100.7$^{ab}$ | 2.4 | 100.5$^{ab}$ | 2.2 |
| 10R [100] | 5 | 59.1 | 0.8 | 87.1 | 1.9 | 107.7$^{de}$ | 1.4 | 103.9$^{bc}$ | 2.2 |

The original 10R [100 mg EP/kg diet] improved the level of soluble protein by about 4%. The effects of 10R-HV1 was slightly higher (5.3% relative increase) and significant. With a dose of 50 and 25 mg EP/kg diet the relative improvements were 3.6% and 2.9%, respectively and significant. With 10 mg EP/kg diet the relative improvement was 0.5%.

Degree of Hydrolysis:

The degree of hydrolysis (DH) was determined using the OPA method. Results are shown in Table 24.

TABLE 24

Degree of Hydrolysis (DH) determined by the OPA method. Absolute as well as relative values are shown. Different letters indicate significant differences (1-way ANOVA, Tukey 95%).

| Enzyme [mgEP/kg] | n | Of total protein | | Relative to blank | | % CV |
|---|---|---|---|---|---|---|
| | | % DH | SD | % DH | | |
| Blank | 5 | 25.89 $a$ | 0.43 | 100.0 $a$ | | 1.65 |
| 10R (FFE-2003-00047) [100] | 5 | 27.19 $bc$ | 0.67 | 105.0 $bc$ | | 2.46 |
| 10R$_{HV1}$ [100] | 5 | 27.89 $c$ | 0.36 | 107.7 $c$ | | 1.29 |

TABLE 24-continued

Degree of Hydrolysis (DH) determined by the OPA method. Absolute as well as relative values are shown. Different letters indicate significant differences (1-way ANOVA, Tukey 95%).

| Enzyme [mgEP/kg] | n | Of total protein | | Relative to blank | | % CV |
|---|---|---|---|---|---|---|
| | | % DH | SD | % DH | | |
| 10R$_{HV1}$ [50] | 5 | 27.34 $bc$ | 0.57 | 105.6 $bc$ | | 2.08 |
| 10R$_{HV1}$ [25] | 5 | 26.42 $ab$ | 0.57 | 102.0 $ab$ | | 2.16 |
| 10R$_{HV1}$ [10] | 5 | 25.52 $a$ | 0.96 | 98.6 $a$ | | 3.76 |

Tail-variant 10R-HV1 improved DH by 7.7%, compared to Blank. With the lower doses (50 and 25 mg EP/kg diet) of the protease the improvements ranged from 5.6-2.0%, respectively, in line with previous findings. At the lowest dose [10 mg EP/kg diet] no effect was seen. The original 10R [100 mg EP/kg diet] showed improvements of 5% relative to Blank.

The results of the HLPC ÄKTA analysis and the DH determinations clearly show that addition of the four amino acid (SEQ ID NO: 5) long tail to 10R does not affect the performance of the 10R protease to any significant extent.

The invention claimed is:

1. A method for producing a secreted, mature polypeptide, the method comprising:
   (a) cultivating a recombinant host cell comprising a polynucleotide encoding a protein comprising:
      (i) a heterologous pro-region comprising a sequence having at least 90% sequence identity to SEQ ID NO:30 and having activity to enhance expression of the protein,
      (ii) a signal peptide comprising a sequence encoded by a polynucleotide having at least 90% sequence identity to residues 1-81 of SEQ ID NO:2, and
      (iii) an amino acid sequence having at least 92% sequence identity to residues 166-353 of SEQ ID NO:43 and that has protease activity, and
   (b) culturing the host cell so as to produce a culture supernatant comprising the secreted, mature polypeptide, said secreted mature polypeptide lacking the heterologous pro-region and the signal peptide, and comprising the sequence having at least 90% sequence identity to residues 166-353 of SEQ ID NO:43 , wherein said sequence has protease activity, and
   (c) recovering the secreted, mature polypeptide.

2. An isolated polynucleotide encoding a polypeptide comprising;
   (i) a heterologous pro-region comprising a sequence having at least 90% sequence identity to SEQ ID NO:30 and having activity to enhance expression of the protein,
   (ii) a signal peptide comprising a sequence encoded by a polynucleotide having at least 90% sequence identity to residues 1-81 of SEQ ID NO:2, and
   (iii) an amino acid sequence having at least 92% sequence identity to residues 166-353 of SEQ ID NO:43 and that has protease activity.

3. A recombinant expression vector or polynucleotide construct comprising the polynucleotide of claim 2.

4. A recombinant host cell comprising the polynucleotide of claim 2, or the expression vector or polynucleotide construct as defined in claim 3.

5. The recombinant host cell according to claim 4 which is a *Bacillus* cell.

6. A method for producing a secreted mature polypeptide, the method comprising:
   (a) cultivating a recombinant host cell comprising a polynucleotide encoding a protein comprising:
      (i) a heterologous pro-region comprising a sequence having at least 92% sequence identity to SEQ ID NO:30 and having activity to enhance expression of the protein,
      (ii) a signal peptide comprising a sequence encoded by a polynucleotide having at least 90% sequence identity to residues 1-81 of SEQ ID NO:2, and
      (iii) an amino acid sequence having at least 98% sequence identity to resides 166-353 of SEQ ID NO:43 and that has protease activity, and
   (b) culturing the host cell so as to produce a culture supernatant comprising the secreted, mature polypeptide, said secreted mature polypeptide lacking the heterologous pro-region and the signal peptide, and comprising the sequence having at least 98% sequence identity to residues 166-353 of SEQ ID NO:43, wherein said sequence has protease activity.

7. The method of claim 6, wherein the secreted mature polypeptide comprises an amino acid sequence having at least 99% sequence identity to residues 166-353 of SEQ ID NO:43.

* * * * *